United States Patent [19]
Vig et al.

[11] Patent Number: 6,124,307
[45] Date of Patent: Sep. 26, 2000

[54] NONNUCLEOSIDE INHIBITORS OF REVERSE TRANSCRIPTASE, COMPOSITE BINDING POCKET AND METHODS FOR USE THEREOF

[75] Inventors: Rakesh Vig, Little Canada; Chen Mao, St. Paul; Faith A. Uckun, White Bear Lake, all of Minn.

[73] Assignee: Wayne Hughes Institute, Roseville, Minn.

[21] Appl. No.: 09/205,469

[22] Filed: Dec. 4, 1998

Related U.S. Application Data

[62] Division of application No. 09/040,538, Mar. 17, 1998, Pat. No. 5,998,411.

[51] Int. Cl.[7] .................. C07D 239/20; A61K 31/505
[52] U.S. Cl. ................. 514/274; 544/311; 544/312; 544/314
[58] Field of Search .................... 544/311, 312, 544/314; 514/274

[56] References Cited

U.S. PATENT DOCUMENTS 5,112,835  5/1992  Miyasaka et al. ............... 544/302

FOREIGN PATENT DOCUMENTS 449726  10/1991  European Pat. Off. ............ 544/311

OTHER PUBLICATIONS

Ahgren, C., et al., 1995, *Antimicrob. Agents Chemotherapy*, 39, 1329–1335 The PETT Series, a New Class of Potent Nonnucleoside Inhibitors of Human Immunodeficiency Virus Type 1 Reverse Transcriptase.

Baba, M., et al., 1992, *Antiviral Res*, 17, 245–264 Highly potent and selective inhibition of HIV–1 replication by 6–phenylthiouracil derivatives.

Balzarini, J. et al., 1992, *Proc. Natl. Acad. Sci. U S A*, 89, 4392–4396 2',5'–Bis–O–(tert–butyldimethylsilyl)–3'–spiro–5"–(4"–amino–1",2"–oxathiole–2",2"–dioxide)pyrimidine (TSAO) nucleoside analogues: Highly selective inhibitors of human immunodeficiency virus type 1 that are targeted at the viral reverse transcriptase.

Bartlett, P.A. et al., 1989, *Molecular Recognition in Chemical and Biological Problems, Special Pub., Royal Chem. Soc.*, 78, 182–196 Caveat: A Program to Facilitate the Structure–derived Design of Biologically Active Molecules.

Bell, F. W., et al., 1995, *J. Med. Chem.*, 38, 4929–4936 Penethylthiazolethiourea (PETT) Compounds, a New Class of HIV–1 Reverse Transcriptase Inhibitors. 1. Syntheis and Basic Structure–Activity Relationship Studies of PETT Analogs.

Blaney, J.M. and Dixon, J.S., 1993, *Perspectives in Drug Discovery and Design*, 1, 301 A good ligand is hard to find: Automated docking methods.

Bohm, H. J., 1992, *J. Comput. Aided. Mol. Des.*, 6, 593–606 LUDI: rule–based automatic design of new substituents for enzyme inhibitor leads.

Bohm, H.J., 1992, *J. Comp. Aid. Molec. Design*, 6, 61–78 The computer program LUDI: A new mehtod for the de novo design of enzyme inhibitors.

Bohm, H. J., *J. Comput. Aided. Mol. Des.*, 1994, 8, 243–256; 1996 The development of a simple empirical scoring function to estimate the binding constant for a protein–ligand complex of konwn three–dimensional structure.

Bosworth, N., et al., 1989, *Nature*, 341: 167–168 Scintillation proximity assay.

Brooks, B.R. et al., 1983, *J. Comp. Chem.*, 4, 187–217. CHARMM: A Program for Macromolecular Energy, Minimization, and Dynamics Calculations.

Burket, U. and Allinger, N.L., 1982, Molecular Mechanics, *ACS Monograph*, 177, 59–78, American Chemical Society, D.C. Methods for the Computation of Molecular Geometry.

Cantrell, A. S., et al., 1996, *J. Med. Chem.*, 39, 4261–4274 Phenethylthiazolylthiourea (PETT) Compounds as a New Class of HIV–1 Reverse Transcriptase Inhibitors. 2. Synthesis and further Structure–Activity Relationship Studies of PETT Analogs.

Connolly, M. L., 1983, *Science*, 221, 709–713 Solvent–Accessible Surfaces of Proteins and Nucleic Acids.

Danel, K. et al., 1997, *Acta Chemica Scandinavica*, 51, 426–430 Anti–HIV Active Napthyl Analogues of HEPT and DABO.

Danel, K. et al., 1998, *J. Med. Chem.*, 41, 191–198 Synthesis and Anti–HIV–1 Activity of Novel 2,3–Dihydro–7H–thiazolo[3,2–α]pyrimidin–7–ones.

Danel, K., et al., 1996, *J. Med. Chem.*, 39, 2427–2431 Synthesis and Potent Anti–HIV–1 Activity of Novel 6–Benzyluracil Analogues of 1–[2–Hydroxyethoxy)methyl]–6–(phenylthio)thymine.

Das, K. et al., 1996, *J. Mol. Biol.*, 264, 1085–1100 Crystal Structures of 8–C1 and 9–C1 TIBO Complexed with Wild–type HIV–1 RT and 8–C1 TIBO Complexed with the Tyr181Cys HIV–1 RT Drug–resistant Mutant.

De Clercq, E., 1992, *J. Acquired Immune Defic. Syndr. Res. Human. Retrovirus*, 8, 119–134.

(List continued on next page.)

*Primary Examiner*—Zinna Northington Davis
*Attorney, Agent, or Firm*—Merchant & Gould P.C.

[57] ABSTRACT

Novel compounds that are potent inhibitors of HIV reverse transcriptase (RT) are described in the invention. Thes novel compounds also inhibit replication of a retrovirus, such as human immunodeficiency virus-1 (HIV-1). The novel compounds of the invention include analogs and derivatives of phenethylthiazolylthiourea (PETT), of dihydroalkoxybenzyloxopyrimidine (DABO), and of 1-[(2-hydroxyethoxy)methyl]-6-(phenylthio)thymine (HEPT).

The invention additionally provides a composite HIV reverse-transcriptase (RT) nonnucleoside inhibitor (NNI) binding pocket constructed from a composite of multiple NNI-RT complexes The composite RT-NNI binding pocket provides a unique and useful tool for designing and identifying novel, potent inhibitors of reverse transcriptase.

11 Claims, 10 Drawing Sheets

OTHER PUBLICATIONS

Ding, J., 1995, et al., *Nat. Struct. Biol.,* 2, 407–415 Structure of HIV–1 RT/TIBO R 86183 complex reveals similarity in the binding of diverse nonnucleoside inhibitors.

Erice, A. et al., 1993, *Antimicrob. Ag. Chemother.,* 37, 835 Anti–Human Immunodeficiency Virus Type 1 Activity of an Anti–CD4 Immunoconjugate Containing Pokeweed Antiviral Protein.

Goodsell, D.S. and Olson, A.J., 1990, *Proteins: Struct. Funct. Genet.,* 8, 195–202 The Molecular Biology of Human Immunodeficiency Virus Type 1 Infection.

Greene, W. C., 1991, *New England Journal of Medicine,* 324, 308–317 Automated Docking of Substrates to Proteins by Simulated Annealing.

Hopkins, A. L. et al., 1996, *J. Med. Chem.,* 39, 1589–1600 Complexes of HIV–1 Reverse Transcriptase with Inhibitors of the HEPT Series Reveal Conformational Changes Relevant to the Design of Potent Non–Nucleoside Inhibitors.

Jones, T. A. et al., 1991, *Acta Crystallogr. A.,* 47, 110–119 Improved Methods for Building Protein Models in Electron Denisty Maps and the Location of Errors in these Models.

Kohlstaedt, L. A. et al., 1992, *Science,* 256, 1783–1790 Crystal Structure at 3.5 Å Resolution of HIV–1 Reverse Transcriptase Complexed with an Inhibitor.

Kuntz, I.D., et al., 1995, *J. Mol. Biol.,* 1982, 161, 269–288 A Geometric Approach to Macromolecule–Ligand Interactions.

Luty, B. A. et al., 1995, *Comp. Chem.,* 16, 454–464 A Molecular Mechanics/Grid Methods for Evaluation of Ligand–Receptor Interactions.

Mai, A. et al., 1997, *J. Med. Chem.,* 40, 1447–1454 Dihydro(alkylthio)(naphthylmethyl)oxopyrimidines: Novel Non– Nucleoside Reverse Transcriptase Indhibitors of the S–DABO Series.

Marshall, G.R., 1987, *Ann. Ref. Pharmacol. Toxicol.,* 27, 193 Computer–Aided Drug Design.

Martin, Y. C., 1992, *J. Med. Chem.,* 35, 2145–2154 3D Database Searching in Drug Design.

Mitsuya, H. et al., 1990, *Science,* 249, 1533–1544 Molecular Targets for AIDS Therapy.

Nishibata, Y. and Itai, A., 1991, *Tetrahedron,* 47, 8985 Automatic Creation of Drug Candidate Structures Based on Receptor Structure. Starting Point for Artificial Lead Generation.

Pauwels, R. et al., 1990, *Nature,* 343, 470–474 Potent and selective inhibitionof HIV–1 replication in vitro by a novel series of TIBO derivatives.

Pontikis, R. et al., 1997, *J. Med. Chem.,* 40, 1845–1854 Synthesis and Anti–HIV Activity of Novel N–1 Side Chain–Modified Analogs of 1–[(2–Hydroxyethoxy)methyl]–6–(phenylthio)thymine (HEPT).

Remington's Pharmaceutical Sciences, Chapter 43, 14th Ed., Mack Publishing Col, Easton PA 18042, USA Topical Drugs.

Ren, J. et al., 1995, *Structure,* 3, 915–926 The structure of HIV–1 reverse transcriptase complexed with 9–chloro–TIBO: lessons for inhibitor design.

Romero, D. L. et al., 1993, *J. Med. Chem.,* 36, 1505–1508 Bis(heteroaryl)piperazine (BHAP) Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)amino]–pyridinyl]piperazine Monomethanesulfonate (U–90152S), a Second–Generation Clinical Candidate.

Tanaka, H. et al., 1991, *J. Med. Chem.,* 34, 349–357 A New Class of HIV–1–Specific 6–Substituted Acyclouridine Derivatives: Synthesis and Anti–HIV–1 Activity of 5–or 6–Substituted Analogues of 1–[(2–Hydroxyethoxy)methyl]– 6–(phenylthio)thymine (HEPT).

Tantillo, C. et al., 1994, *J Mol Biol,* 243, 369–387 Locations of Anti–AIDS Drug Binding Sites and Resistance Mutations in the Three–dimensional Structure of HIV–1 Reverse Transcriptase.

Uckun, F. M. et al., 1998, *Antimicrobial Agents and Chemotherapy,* 42, 383 TXU (Anti–CD7)–Pokeweed Antiviral Protein as a Potent Inhibitor of Human Immunodeficiency Virus.

Weiner, S.J. et al., 1984, *J. Am. Chem. Soc.,* 106, 765–784 A New Force Field for Molecular Mechanical Simulation of Nucleic Acids and Proteins.

Zarling, J. M. et al., 1990, *Nature,* 347, 92–95 Inhibition of HIV replication by pokeweed antiviral protein targeted to $CD4^+$ cells by monoclonal antibodies.

FIG. IA
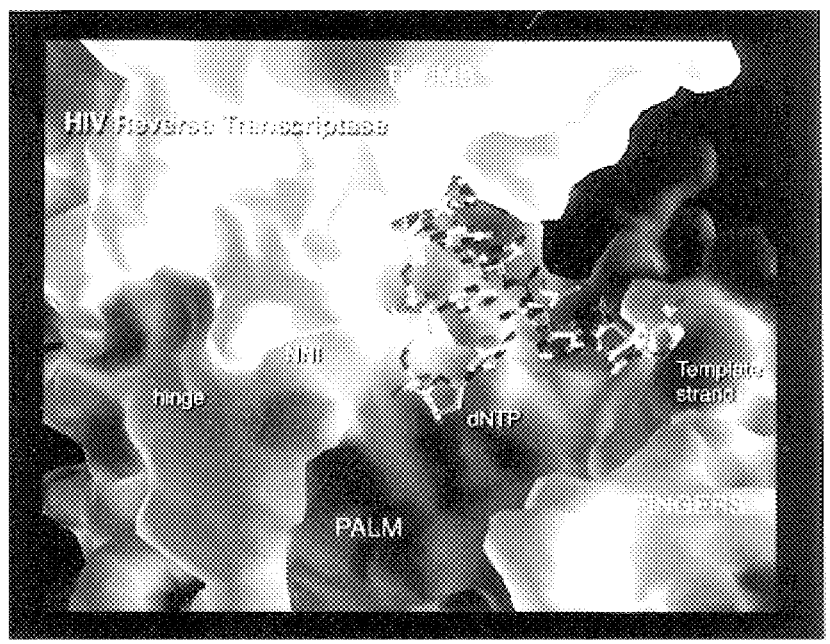
FIG. IB
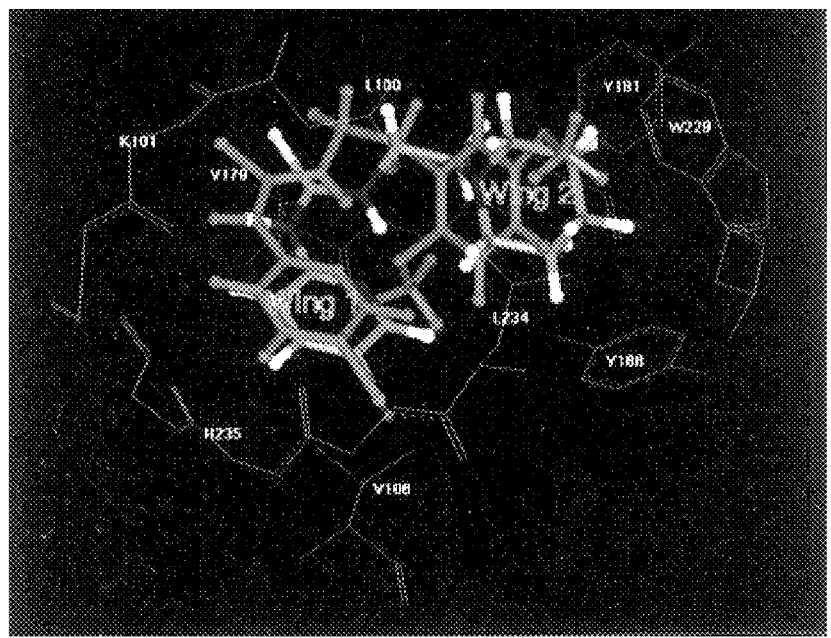

NONNUCLEOSIDE INHIBITORS OF REVERSE TRANSCRIPTASE, COMPOSITE BINDING POCKET AND METHODS FOR USE THEREOF

This application is a Divisional of application Ser No. 09/040,538, filed Mar. 17, 1998, is now U.S. Pat. No. 5,998,411 issued Dec. 7, 1999 which application is incorporated herein by reference.

Throughout this application various publications are referenced. The disclosures of these publications in their entireties are hereby incorporated by reference into this application in order to more fully describe the state of the art to which this invention pertains.

The inventors acknowledge and appreciate the assistance of Dr. Elise Sudbeck.

BACKGROUND OF THE INVENTION

Design of potent inhibitors of human immunodeficiency virus (HIV-1) reverse transcriptase (RT), an enzyme responsible for the reverse transcription of the retroviral RNA to proviral DNA, has been a focal point in translational AIDS research efforts (Greene, W. C., *New England Journal of Medicine*, 1991, 324, 308–317; Mitsuya, H. et al., *Science*, 1990, 249, 1533–1544; De Clercq, E., *J. Acquired Immune Defic. Syndr. Res. Human. Retrovirus*, 1992, 8, 119–134). Promising inhibitors include nonnucleoside inhibitors (NNI), which bind to a specific allosteric site of HIV-1 RT near the polymerase site and interfere with reverse transcription by altering either the conformation or mobility of RT, thereby leading to noncompetitive inhibition of the enzyme (Kohlstaedt, L. A. et al., *Science*, 1992, 256, 1783–1790).

NNI of HIV-1 RT include the following:

(a) 1-[(2-hydroxyethoxy)methyl]-6-(phenylthio)thymines (HEPT; Tanaka, H. et al., *J. Med. Chem.*, 1991, 34, 349–357; Pontikis, R. et al., *J. Med. Chem.*, 1997, 40, 1845–1854; Danel, K., et al., *J. Med. Chem.*, 1996, 39, 2427–2431; Baba, M., et al., *Antiviral Res*, 1992, 17, 245–264);

(b) tetrahydroimidazobenzodiazepinethiones (TIBO; Pauwels, R. et al., *Nature*, 1990, 343, 470–474);

(c) bis(heteroaryl)piperazines (BHAP; Romero, D. L. et al., *J. Med. Chem.*, 1993, 36, 1505–1508);

(d) dihydroalkoxybenzyloxopyrimidine (DABO; Danel, K. et al., *Acta Chemica Scandinavica*, 1997, 51, 426–430; Mai, A. et al., *J. Med. Chem.*, 1997, 40, 1447–1454);

(e) 2'-5'-bis-O-(tertbutyldimethylsilyl)-3'-spiro-5"-(4"-amino-1",2"-oxathiole-2",2"-dioxide) pyrimidines (TSAO; Balzarini, J. et al., *Proc. Natl. Acad. Sci USA*, 1992, 89, 4392–4396); and (f) phenethylthiazolylthiourea (PETT) derivatives (Bell, F. W. et al., *J. Med. Chem.*, 1995, 38, 4929–4936; Cantrell, A. S. et al., *J. Med. Chem.*, 1996, 39, 4261–4274).

Current protein structure-based drug design efforts rely heavily on crystal structure information of the target binding site. A number of crystal structures of RT complexed with NNIs (including α-APA, TIBO, Nevirapine, BHAP and HEPT derivatives) have been reported, and such structural information provides the basis for further derivatization of NNI aimed at maximizing binding affinity to RT. However, the number of available crystal structures of RT NNI complexes is limited, and no structural information has been reported for RT-PETT complexes or RT-DABO complexes. Given the lack of structural information, researchers must rely on other design procedures for preparing active PETT and DABO derivatives. One of the first reported strategies for systematic synthesis of PETT derivatives was the analysis of structure-activity relationships independent of the structural properties of RT and led to the development of some PETT derivatives with significant anti-HIV activity (Bell, F. W. et al., *J. Med. Chem.*, 1995, 38, 4929–4936; Cantrell, A. S. et al., *J. Med. Chem.*, 1996, 39, 4261–4274). The inclusion of structural information in the drug design process should lead to more efficient identification of promising RT inhibitors.

Although the crystal structure of an RT-NNI complex can be used to provide useful information for the design of a different type of NNI, its application is limited. For example, an analysis of the RT-APA (α-anilinophenylacetamide) complex structure would not predict that the chemically dissimilar inhibitor TNK (6-benzyl-1-benzyloxymethyl uracil) could bind in the same region. The RT-APA structure reveals that there would not be enough room in the APA binding site for the 1-benzyloxymethyl group of TNK (Hopkins, A. L. et al., *J. Med. Chem.*, 1996, 39, 1589–1600). Nevertheless TNK is known to bind in this region as evidenced by the crystal structure of RT-TNK which shows that RT residues can adjust to accommodate the 1-benzyloxymethyl group. Conversely, an analysis of the RT-TNK complex would not predict favorable binding of APA in the TNK binding site. The structure does not show how residue E138 can move to accommodate the 2-acetyl group of the A-APA inhibitor.

Thus, any NNI binding pocket model based on an individual RT-NNI crystal structure would have limited potential for predicting the binding of new, chemically distinct inhibitors. To overcome this problem, the invention disclosed herein uses the NNI binding site coordinates of multiple, varied RT-NNI structures to generate a composite molecular surface. A specific embodiment of the invention is a composite molecular surface or binding pocket generated from nine distinct RT-NNI complexes, and reveals a larger than presumed NNI binding pocket not shown or predicted by any of the individual structures alone (FIG. 2A). This novel composite binding pocket, together with a computer docking procedure and a structure-based semi-empirical score function, provides a guide to predict the energetically favorable position of novel PETT, DABO, and HEPT derivatives, as well as other novel compounds, in the NNI binding site of RT.

The invention further provides a number of computational tools which set forth a cogent explanation for the previously unexplained and not understood relative activity differences among NNIs, including PETT, DABO, and HEPT derivatives, and reveals several potential ligand derivatization sites for generating new active derivatives. Disclosed herein is the structure-based design of novel HEPT derivatives and the design and testing of non-cytotoxic PETT and DABO derivatives which abrogate HIV replication in human peripheral blood mononuclear cells at nanomolar concentrations with an unprecedented selectivity index of >$10^5$.

One procedure useful in structure-based rational drug design is docking (reviewed in Blaney, J. M. and Dixon, J. S., *Perspectives in Drug Discovery and Design*, 1993, 1, 301). Docking provides a means for using computational tools and available structural data on macromolecules to obtain new information about binding sites and molecular interactions. Docking is the placement of a putative ligand in an appropriate configuration for interacting with a receptor. Docking can be accomplished by geometric matching of a ligand and its receptor, or by minimizing the energy of interaction. Geometric matching is faster and can be based on descriptors or on fragments.

Structure-based drug design efforts often encounter difficulties in obtaining the crystal structure of the target and predicting the binding modes for new compounds. The difficulties in translating the structural information gained from X-ray crystallography into a useful guide for drug synthesis calls for continued effort in the development of computational tools. While qualitative assessments of RT-inhibitor complexes provide helpful information, systematic quantitative prediction of inhibitory activity of new compounds based on structural information remains a challenge.

There is a need for more complete information on the structure and flexibility of the NNI binding pocket and for an improved model of the binding pocket to serve as a basis for rational drug design. In addition, there is a need for more effective inhibitors of reverse transcriptase, particularly HIV-1 reverse transcriptase.

The invention disclosed herein addresses these needs by providing a model for the three-dimensional structure of the RT-NNI binding pocket based on the available backbone structure of RT-DNA complex and full structure of RT complexed with several NNI compounds. Structural information from multiple RT-NNI complexes was combined to provide a suitable working model. In one embodiment, the NNI binding site coordinates of nine RT-NNI structures is used to generate a composite molecular surface revealing a larger than presumed NNI binding pocket. This pocket, together with docking and a structure-based semi-empirical score function, can be used as a guide for the synthesis and analyses of structure-activity relationships for new NNI of RT, including new derivatives of HEPT, DABO, and PETT, as well as novel compounds having little or no relationship to known NNIs. The practical utility of this novel composite model is illustrated and validated by the observed superior potency of new PETT and S-DABO derivatives as anti-HIV agents, described herein.

SUMMARY OF THE INVENTION

The invention provides novel compounds which inhibit reverse transcriptase (RT) and which inhibit replication of a retrovirus, such as human immunodeficiency virus-1 (HIV-1). In one embodiment, the novel compounds of the invention are analogs or derivatives of phenethylthiazolylthiourea (PETT), dihydroalkoxybenzyloxopyrimidine (DABO) or 1-[(2-hydroxyethoxy)methyl]-6-(phenylthio)thymine (HEPT). Alternatively, the novel compounds of the invention bind the NNI binding pocket, but are not related to any known NNI. Specific compounds of the invention are described more fully in the Detailed Description and in the Examples below.

The invention additionally provides compositions and methods for inhibiting reverse transcriptase activity of a retrovirus, such as HIV-1, by contacting the RT binding site of the retrovirus with a compound of the invention. The methods of the invention are useful for inhibiting replication of a retrovirus, such as HIV-1 and include treating a retroviral infection in a subject, such as an HIV-1 infection, by administering a compound or composition of the invention, for example, in a pharmaceutical composition.

The invention further provides a composite ligand binding pocket constructed by superimposing multiple structures of ligand-binding site complexes. Preferably, the composite binding pocket is constructed by superimposing the structures of at least one each of the following NNI complexed with RT: a compound, analog or derivative of HEPT or MKC; TNK, APA, Nevipapine, and TIBO. In one embodiment, the composite ligand binding pocket is an HIV-1 reverse-transcriptase (RT) nonnucleoside inhibitor (NNI) binding pocket constructed by superimposing nine structures of NNI-RT complexes, preferably having the coordinates set forth in Table 9.

Using the novel composite binding pocket of the invention, compounds that bind to the NNI binding site of reverse transcriptase can be identified and/or screened. For example, a useful inhibitor is identified by analyzing the fit of a candidate compound to the composite binding pocket is analyzed. In one embodiment, the comparing comprises analyzing the molecular surface of the composite binding pocket. The extent of contact between the molecular surface of the compound and the molecular surface of the binding pocket can be visualized, and any gap space between the compound and the composite binding pocket can be determined and quantified. The candidate inhibitory compound can be docked in the composite binding pocket, and its binding characteristics analyzed. For example, an estimate of the inhibition constant for the docked compound can be calculated. The value of the inhibition constant is inversely related to the affinity of the candidate compound for the binding pocket.

Using information provided by the composite binding pocket of the invention, novel inhibitors of reverse transcriptase can be designed and screened. Using molecular modeling techniques, a compound can be docked into an RT-NNI binding pocket, and the complex analyzed for its binding characteristics. Gap space or regions that do not demonstrate optimum close contacts between the compound and the binding pocket are identified, permitting the compound to be modified to better occupy the site. In such a method, novel inhibitors of reverse transcriptase are designed and screened.

Also provided by the invention are inhibitors of reverse transcriptase identified or designed by analyzing the compound's structural fit to the binding pocket. Potent inhibitors designed and confirmed using the composite binding pocket of the invention include analogs and derivatives of known NNI, such as phenethylthiazolylthiourea (PETT) analogs, dihydroalkoxybenzyloxopyrimidine (DABO) analogs, and 1-[(2-hydroxyethoxy)methyl]-6-(phenylthio)thymine (HEPT) analogs.

The compounds of the invention may be combined with carriers and/or agents to enhance delivery to sites of viral infection, such as targeting antibodies, cytokines, or ligands. The compounds may include chemical modifications to enhance entry into cells, or may be encapsulated in various known delivery systems.

BRIEF DESCRIPTION OF THE FIGURES

FIG. 1A is a model of the HIV-1 reverse transcriptase (RT) active site, derived primarily from two crystal structures: HIV-1 RT (PDB access code hni) and HIV-1 RT with DNA fragment (PDB access code hmi). The binding site for non-nucleoside inhibitors is labeled NNI. The site for nucleoside inhibitors is labeled dNTP which includes the 3' terminus of DNA. Features describing the geometry of the binding region include the thumb, palm, fingers, and hinge region of RT.

FIG. 1B shows models of compound I-3 (color coded by atom type) and compound I-4 (in blue) in NNI binding site of HIV reverse transcriptase, positioned by docking procedure. Wing 1 and Wing 2 represent two different regions of the NNI binding site.

DETAILED DESCRIPTION OF THE INVENTION

Definitions

Figure 2A:
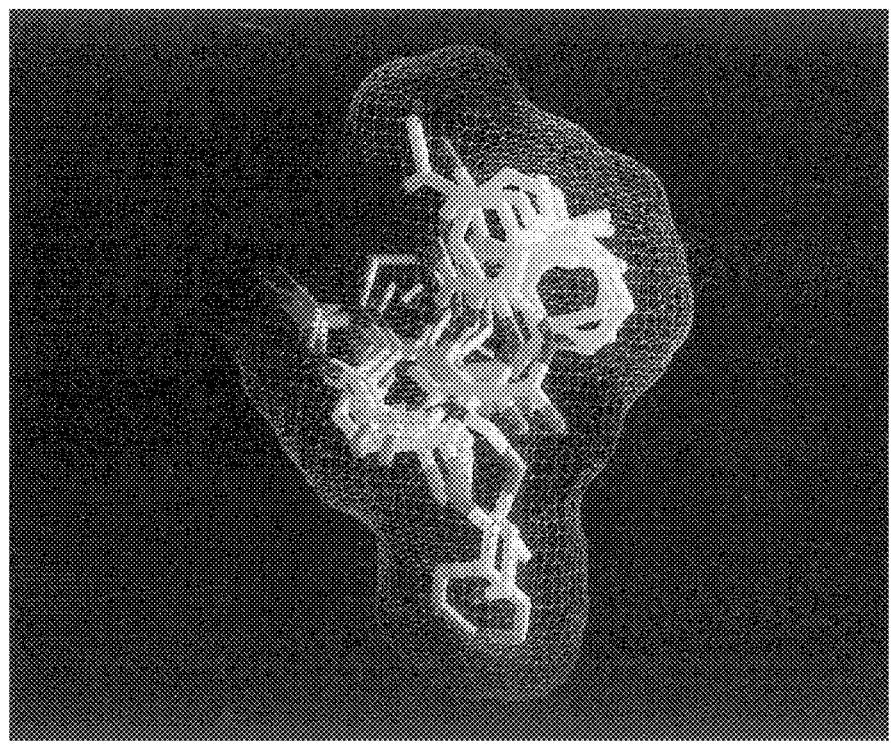
FIG. 2A shows a composite binding pocket of NNI active site of HIV-1 RT. Grid lines represent the collective van der Waals surface of nine different inhibitor crystal structures superimposed in the active site and highlight the available space for binding (inhibitor structures include HEPT, MKC, TNK, APA, Nevirapine, N-ethyl Nevirapine derivative, 8-Cl TIBO, and two 9-Cl TIBO compounds, with PDB access codes rti, rt1, rt2, hni, vrt, rth, hnv, rev and tvr, respectively). The surface is color-coded for hydrogen bonding (red), hydrophobic (gray) and hydrophilic (blue) groups of the superimposed inhibitors. The hydrogen atoms were not included.

All scientific and technical terms used in this application have meanings commonly used in the art unless otherwise specified. As used in this application, the following words or phrases have the meanings specified.

As used herein, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having an NNI binding site similar to that of HIV-1 RT and to which ligands which bind the composite binding pocket of the invention bind.

As used herein, "reverse transcriptase (RT) activity" means the ability to effect reverse transcription of retroviral RNA to proviral DNA. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., *Nature* 1989, 341:167–168.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a "nonnucleoside inhibitor (NNI)" of HIV reverse-transcriptase (HIV-RT) means a compound which binds to an allosteric site of HIV-RT, leading to noncompetitive inhibition of HIV-RT activity. Examples of nonnucleoside inhibitors of HIV-RT include, but are not limited to, tetrahydroimidazobenzodiazepinthiones (TIBO), 1-[(2-hydroxyethoxy)methyl]-6-(phenylthio)thymines (HEPT), bis(heteroaryl)piperazines (BHAP), 2'-5'-bis-O-(tertbutyldimethylsilyl)-3'-spiro-5"-(4"-amino-1",2"-oxathiole-2",2"-dioxide) pyrimidines (TSAO), dihydroalkoxybenzyloxopyrimidine (DABO) and phenethylthiazolylthiourea (PETT) analogs. In one embodiment of the invention, the nonnucleoside inhibitor of HIV-RT is a PETT analog. In another embodiment of the invention, the nonnucleoside inhibitor of HIV-RT is a DABO analog. In another embodiment of the invention, the nonnucleoside inhibitor of HIV-RT is a HEPT analog.

As used herein, a "composite HIV reverse-transcriptase (RT) nonnucleoside inhibitor (NNI) binding pocket" or "composite binding pocket" means a model of the three-dimensional structure of a ligand binding site, such as the nonnucleoside inhibitor binding site of HIV-RT constructed from a composite of multiple ligand-binding site complexes. The composite binding pocket represents a composite molecular surface which reveals regions of flexibility within the binding site. Flexible residues within the NNI binding site include Tyr180, Tyr181, Tyr318, Tyr319, Phe227, Leu234, Trp229, Pro95, and Glu138 (the latter from the p51 subunit of RT). Examples of such a model include, but are not limited to, a composite molecular surface developed with the aid of computer software and based on a composite of coordinates of multiple RT-NNI complexes, as disclosed herein. In one embodiment, the binding pocket has the coordinates set forth in Table 9.

As used herein, a "compound that fits the nonnucleoside inhibitor (NNI) pocket of reverse transcriptase (RT)" means a compound that substantially enters and binds the NNI binding site on RT. In one embodiment, a compound that fits the NNI pocket of RT inhibits RT activity. Generally, compounds which better fit the NNI pocket of RT contact a greater portion of the available molecular surface of the pocket and are more potent inhibitors of RT activity. In one embodiment, the compound that fits the NNI pocket of RT is a PETT analog. In another embodiment, the compound that fits the NNI pocket of RT is a DABO analog. In another embodiment, the compound that fits the NNI pocket of RT is a HEPT analog.

As used herein, "docking" a compound in a binding pocket means positioning a model of a compound in a model of the binding pocket. In one embodiment, the model of the binding pocket can be a composite binding pocket constructed in accordance with the invention. The model of the binding pocket can be, for example, based on coordinates obtained from the crystal structure of RT complexed with a NNI. In one embodiment, the docking is performed with the use of computer software, such as the Affinity program within InsightII (Molecular Simulations Inc., 1996, San Diego, Calif.). Docking permits the identification of positions of the compound within the binding pocket that are favored, for example, due to minimization of energy.

As used herein, "minimization of energy" means achieving an atomic geometry of a molecule or molecular complex via systematic alteration such that any further minor perturbation of the atomic geometry would cause the total energy of the system as measured by a molecular mechanics force-field to increase. Minimization and molecular mechanics force-fields are well understood in computational chemistry (Burkert, U. and Allinger, N. L., Molecular Mechanics, *ACS Monograph*, 1982, 177, 59–78, American Chemical Society, Washington, D.C.).

As used herein, "comparing" includes visualizing or calculating available space encompassed by the molecular surface of the composite binding pocket of the invention, taking into account the flexibility of residues, such as Tyr180, Tyr181, Tyr318, Tyr319, Phe227, Leu234, Trp229, Pro95, and Glu138 of RT (the latter from the p51 subunit of RT). "Comparing" also includes calculating minimal energy conformations.

As used herein, "gap space" means unoccupied space between the van der Waals surface of a compound positioned within the binding pocket and the surface of the binding pocket defined by residues in the binding site. This gap space between atoms represents volume that could be occupied by new functional groups on a modified version of the compound positioned within the binding pocket.

In the present invention, the terms "analog" or "derivative" are used interchangeably to mean a chemical substance that is related structurally and functionally to another substance. An analog or derivative contains a modified structure from the other substance, and maintains the function of the other substance, in this instance, maintaining the ability to interact with an NNI-RT binding site. The analog or derivative need not, but can be synthesized from the other substance. For example, a HEPT analog means a compound structurally related to HEPT, but not necessarily made from HEPT.

As used herein, "alkyl" includes both branched and straight-chain saturated aliphatic hydrocarbon groups having the specified number of carbon atoms.

As used herein, "alkene" includes both branched and straight-chain unsaturated aliphatic hydrocarbon groups having the specified number of carbon atoms.

As used herein, "halogen" includes fluoro, chloro, bromo and iodo.

As used herein "non-hydrogen atom group" includes, but is not limited to, alkyl, alkenyl, alkynyl, halo, hydroxy, alkoxy, thiol, thiolalkyl, amino, substituted amino, phosphino, substituted phosphino, or nitro. In addition, cycloalkyl, aryl, and aralkyl groups may be included if the non-hydrogen atom group contains a sufficient number of non-hydrogen atoms. Often, a number or range of numbers is specified to indicate the number of non-hydrogen (e.g., C, O, N, S, or P) atoms in the functional group.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with a compound of the invention, allows the compound to retain biological activity, such as the ability to inhibit RT activity, and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Col, Easton Pa. 18042, USA).

Composite Binding Pocket of the Invention

As shown in FIG. 1, the NNI binding site of HIV-RT rests between the palm and thumb regions of the RT molecular structure, adjacent to the hinge region. The NNI binding site includes two distinct regions, indicated in FIG. 1B as Wing 1 and Wing 2, forming a butterfly-shaped binding pocket.

In the method of the invention, a composite ligand binding pocket is constructed by superimposing multiple structures of ligand-binding site complexes, preferably using 5 or more distinct structures. In one embodiment, the composite ligand binding pocket is an HIV-1 reverse-transcriptase (RT) nonnucleoside inhibitor (NNI) binding pocket constructed by superimposing multiple structures of NNI-RT complexes. The composite binding pocket is preferably an HIV-1 RT-NNI binding pocket.

A preferred binding pocket of the invention can be made by superimposition of coordinates, obtainable from the Protein Data Bank (PDB) via access codes disclosed herein, corresponding to the three-dimensional structure of an RT-NNI complex. The superimposition of coordinates is preferably based on alignment of the coordinates corresponding to the palm region of the binding pocket due to the greater rigidity of this region.

The superimposing of coordinates can also be accomplished by first using models of the protein backbone and DNA phosphate backbone of the RT-DNA complex structure (with PDB access code hmi) onto a model of an RT mutant complexed with an NNI, such as APA ((2-acetyl-5-methylanilino)(2,6-dibromophyl)acetamide) having PDB access code hni. Next, models of one or more additional RT-NNI complexes are superimposed onto the models superimposed above. In one embodiment, the superimposition is based on alignment of the region of RT from residue 100 to 230, preferably by a least squares procedure. In another embodiment, the superimposition is based on alignment of the region of RT from residues 97 to 213. Preferably, the superimposition is based on alignment of the palm region and part of the NNI binding site. Most preferably, the superimposition is based on alignment of the region corresponding to residues 100 to 230 of RT, or on alignment of 117 C alpha atoms of residues 97 to 213, and preferably using a least squares procedure.

A molecular surface of a binding pocket can then be generated that encompasses all superimposed NNI models. One such composite binding pocket constructed from nine individual NNI-RT complex structures, is shown in FIG. 2A. Grid lines in the figure represent the collective van der Waals surface, and highlight space available for binding.

The molecular surface of the complex can be generated, for example, by reading the overlaid coordinates of the complexed inhibitors into a computer program such as GRASP (A. Nicholls, GRASP, Graphical Representation and Analysis of Surface Properties, 1992, N.Y.). Examples of NNI compounds which can be used in the construction of a binding pocket include, but are not limited to, HEPT, MKC, TNK, APA, Nevirapine, N-ethyl Nevirapine derivative, 8-Cl TIBO, and 9-Cl TIBO (PDB access codes, rti, rt1, rt2, hni, vrt, rth, hnv and rev or tvr, respectively).

Using the composite NNI binding pocket, binding of compounds can be modeled to identify available space within the binding pocket. New and more potent NNI inhibitors of RT can be developed by designing compounds to better fit the binding pocket.

In one embodiment, the composite binding pocket is constructed by superimposing structures of NNI-RT complexes comprising RT complexed with: an HEPT or MKC analog; a TNK analog; an APA analog; a Nevirapine analog; and a TIBO analog. In another embodiment, the composite NNI binding pocket is based on the structure of RT complexed with 9 NNI and on the RT-DNA complex. Examples of NNI compounds which can be used in the construction of a binding pocket include, but are not limited to, HEPT, MKC, TNK, APA, Nevirapine, N-ethyl Nevirapine derivative, 8-Cl TIBO, and 9-Cl TIBO structures (PDB access codes, rti, rt1, rt2, hni, vrt, rth, hnv, and tvr and/or rev, respectively). In one embodiment, the resulting composite binding pocket has the coordinates set forth in Table 9.

Construction and Use of the Binding Pocket

A compound that binds the NNI binding site of reverse transcriptase is identified by comparing a test compound to the composite binding pocket of the invention and determining if the compound fits the binding pocket. As shown in FIGS. 7A and 7B, the test compound may be compared to another inhibitory compound, by superimposing the structures in the binding pocket. The test compound is also compared to the binding pocket by calculating the molecular surface of the compound complexed with the composite binding pocket. The extent of contact between the molecular surface of the compound and the molecular surface of the binding pocket can be visualized, and the gap space between the compound and the binding pocket can be calculated. In FIGS. 4A and 4B, gaps between the molecular surface of the binding pocket and the NNI are presented in red, with each red line being 1 angstrom in distance.

To design a novel inhibitor of reverse transcriptase, a compound is docked in the composite binding pocket of the invention. Gap space is identified between the compound and the binding pocket, for example, using an algorithm based on a series of cubic grids surrounding the docked compound, with a user-defined grid spacing. The compound is then modified to more completely occupy the gap space.

Computerized docking procedures can be used to dock the test compound in the binding pocket and analyze the fit. One docking program, DOCK (Kuntz, I. D., et al., *J. Mol. Biol.,* 1982, 161, 269–288; available from University of California, San Francisco), is based on a description of the negative image of a space-filling representation of the receptor that should be filled by the ligand. DOCK includes a force-field for energy evaluation, limited conformational flexibility and consideration of hydrophobicity in the energy evaluation. CAVEAT (Bartlett, P. A. et al., *Molecular Recognition in Chemical and Biological Problems, Special Pub., Royal Chem. Soc.,* 1989, 78, 182–196; available from University of California, Berkeley) suggests ligands to a particular receptor based on desired bond vectors. HOOK (Molecular Simulations, Burlington, Mass.) proposes docking sites by using multiple copies of functional groups in simultaneous searches. MACCS-3D (Martin, Y. C., *J. Med. Chem.,* 1992, 35, 2145–2154) is a 3D database system available from MDL Information Systems, San Leandro, Calif. Modeling or docking may be followed by energy minimization with standard molecular mechanics forcefields or dynamics with programs such as CHARMM (Brooks, B. R. et al., *J. Comp. Chem.,* 1983, 4, 187–217) or AMBER (Weiner, S. J. et al., *J. Am. Chem. Soc.,* 1984, 106, 765–784).

LUDI (Bohm, H. J., *J. Comp. Aid. Molec. Design,* 1992, 6, 61–78; available from Biosym Technologies, San Diego, Calif.) is a program based on fragments rather than on descriptors. LUDI proposes somewhat larger fragments to match with the interaction sites of a macromolecule and scores its hits based on geometric criteria taken from the Cambridge Structural Database (CSD), the Protein Data Bank (PDB) and on criteria based on binding data. Other software which can be used to propose modifications for constructing novel inhibitors include LEGEND (Nishibata, Y. and Itai, A., *Tetrahedron,* 1991, 47, 8985; available from Molecular Simulations, Burlington, Mass.) and LeapFrog (Tripos Associates, St. Louis, Miss.).

The AUTODOCK program (Goodsell, D. S. and Olson, A. J., *Proteins: Struct. Funct. Genet.,* 1990, 8, 195–202; available from Scripps Research Institute, La Jolla, Calif.) helps in docking ligands to their receptive proteins in a flexible manner using a Monte Carlo simulated annealing approach. The procedure enables a search without bias introduced by the researcher. This bias can influence orientation and conformation of a ligand in the active site. The starting conformation in a rigid docking is normally biased towards an energy minimum conformation of the ligand. However, the binding conformation of the ligand may be of relatively high conformational energy, but offset by the binding energy.

In a preferred embodiment of the invention, docking is performed by using the Affinity program within InsightII (Molecular Simulations Inc., 1996, San Diego, Calif.). As modeling calculations progress during the docking procedure, residues within a defined radius of 5 Å from the NNI molecule are allowed to move in accordance with energy minimization, permitting the identification of promising positions for modification. Initial coordinates of newly designed compounds can be generated using the Sketcher module within InsightII.

In one embodiment, the method further comprises calculating the inhibition constant of the docked compound. Inhibition constants ($K_i$ values) of compounds in the final docking positions can be evaluated using a score function in the program, LUDI (Bohm, H. J., *J. Comput. Aided Mol. Des.*, 1994, 8, 243–256; Bohm, H. J., *J. Comput. Aided Mol. Des.*, 1992, 6, 593–606). Predictions of $K_i$ values can be improved by modifications of the LUDI calculation., for example, those described in Example 1. First, the molecular surface area can be directly calculated from the coordinates of the compounds in docked conformation using the MS program described in Connolly, M. L., 1983 *Science* 221:709–713. Second, because InsightII does not account for structural rigidity imposed by internal hydrogen bonds, the number of rotatable bonds can be re-evaluated. For example, this re-evaluation can be performed by counting the number of rotatable bonds according to the principle introduced by Bohm (supra) and taking out the number of bonds which are not rotatable due to the conformational restraint imposed by the internal hydrogen bond between the thiourea NH and pyridyl N in PETT derivatives. Third, the calculation can be modified by the assumption that the conserved hydrogen bond with RT does not deviate significantly from the ideal geometry. This assumption is supported by the fact that, in known crystal structures of RT complexes, all hydrogen bonds between NNIs and RT are near the ideal geometry. These constraints provide for more predictive $K_i$ values for modeled compounds.

In a preferred embodiment, the compound has a predicted inhibition constant ($K_i$) of less than about 1 $\mu$M, and the compound in the binding has an estimated molecular surface area greater than 276 Å$^2$.

Candidate inhibitors of RT identified or designed by the methods of the invention can be evaluated for their inhibitory activity using conventional techniques which typically involve determining the location and binding proximity of a given moiety, the occupied space of a bound inhibitor, the deformation energy of binding of a given compound and electrostatic interaction energies. Examples of conventional techniques useful in the above evaluations include, but are not limited to, quantum mechanics, molecular dynamics, Monte Carlo sampling, systematic searches and distance geometry methods (Marshall, G. R., *Ann. Ref. Pharmacol. Toxicol.*, 1987, 27, 193). Examples of computer programs for such uses include, but are not limited to, Gaussian 92, revision E2 (Gaussian, Inc. Pittsburgh, Pennsylvania), AMBER version 4.0 (University of California, San Francisco), QUANTA/CHARMM (Molecular Simulations, Inc., Burlington, Mass.), and Insight II/Discover (Biosym Technologies Inc., San Diego, Calif.). These programs may be implemented, for example, using a Silicon Graphics Indigo2 workstation or IBM RISC/6000 workstation model 550. Other hardware systems and software packages will be known and of evident applicability to those skilled in the art.

Inhibitors identified or designed by the methods of the invention can be tested for their anti-HIV or anti-RT activity using one of the standard in vitro assays known in the art, such as the p24 enzyme immunoassay disclosed herein.

The invention further provides novel compounds identified by the above methods, which can be used as inhibitors of RT. Novel inhibitors so identified include analogs or derivatives of known NNI compounds such as HEPT, DABO, and PETT, as well as novel compounds designed to fit the composite binding pocket which are unrelated to any known NNI compound.

Compounds of the Invention

Compounds of the invention are useful as nonnucleoside inhibitors of RT. These include, for example, analogs and derivatives of PETT, DABO, and HEPT compounds, as well as novel compounds unrelated to known NNI but designed to fit the composite binding pocket.

PETT compounds:

Novel compounds of the invention include derivatives and analogs of PETT, having the general formula (I):

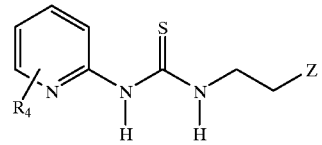

(I)

Z can be phenyl, piperizine, piperidine, or morpholine. Z is preferably substituted with one or more substituents, including alkyl, alkene, halogen, methoxy, alcohol, amino, thio, thioxy, or phosphino. In one embodiment, the compounds of the invention are PETT derivatives or analogs having the following formula (II):

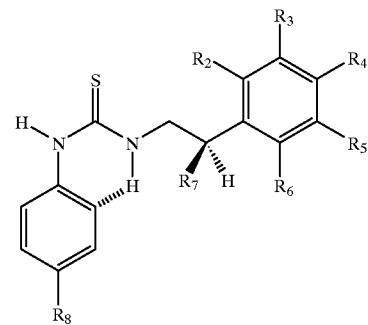

(II)

The R's can be the same or different, and represent points of optional substitution. $R_2$, $R_3$, $R_4$, $R_5$, $R_6$, $R_7$ and $R_8$ can be hydrogen, or can be substituted, with a non-hydrogen atom group such as halo (Br, Cl, F, I), alkyl, alkenyl, hydroxy, alkoxy, thioalkyl, thiol, phosphino, ROH, or $RNH_2$ group, where R is alkyl. Preferably, one or more is alkyl, halo, or alkoxy. Preferred halogens are F, Br, or Cl. One or more of $R_2$, $R_3$, $R_4$, $R_5$, $R_6$, and $R_7$ can be a $C_1$–$C_3$ alkoxy, e.g., methoxy.

$R_8$ can also be aryl, aralkyl, ROH, or $RNH_2$ group, where R is alkyl. Preferably, at least one of $R_2$, $R_3$, $R_4$, $R_5$, and $R_6$ is not hydrogen. $R_4$ is a preferably hydrophobic group such as H, an alkyl or alkene, and can be Me, Et, or i-Pr. $R_6$ and/or $R_7$ are preferably a 3 or 4 (non-hydrogen)-atom group.

$R_6$ and $R_7$ can be a group having 1 to 4 non-hydrogen atoms, whereas $R_2$, $R_3$, and $R_5$ preferably each are a group having 1 to 3 non-hydrogen atoms. Available gap space in the binding pocket near $R_8$, is approximately 8 angstroms by 5 angstroms, by 3.3 angstroms. Thus, a molecule having a volume of up to about 8×6×4 angstroms can be used to fill this space, e.g., accommodating a group of about 7 non-hydrogen atoms, or up to about the size of a phenyl ring. $R_8$ can be halo, alkyl, phenyl, —$CH_2Ph$, or alkoxy. $R_8$ can be X—R, where X is a bridging atom, including, but not limited to, C, S, O, N and P.

In a preferred embodiment, $R_8$ is bromine, and at least one of $R_2$, $R_3$, $R_4$, $R_5$, and $R_6$ is fluoro, chloro, or methoxy.

A compound of the invention preferably conforms to the composite NNI binding pocket of the invention. Most preferably, the compound complexed with an NNI-RT binding pocket, has a predicted $K_i$ of less than about 1 $\mu M$.

Preferred modifications of PETT compounds include ortho-halogen, meta-O-Me, and hydrophobic groups at the para position of the ring. Most preferably, the modifications do not disrupt the intramolecular hydrogen bond. Specific compounds include those having the following formulae (III–VIII) shown below.

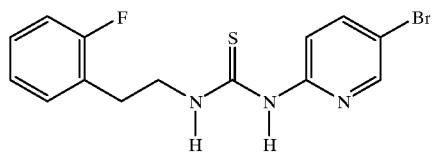

(III)

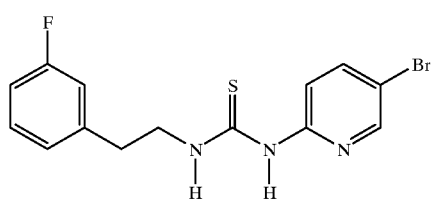

(IV)

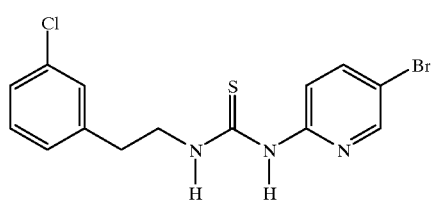

(V)

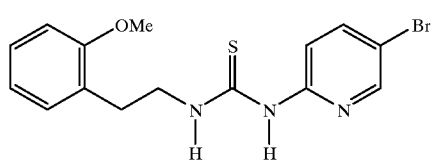

(VI)

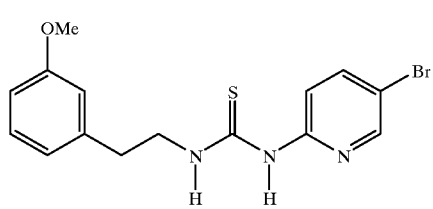

(VII)

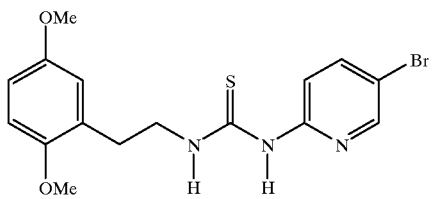

(VIII)

In another embodiment, the PETT derivative comprises the formula (IX):

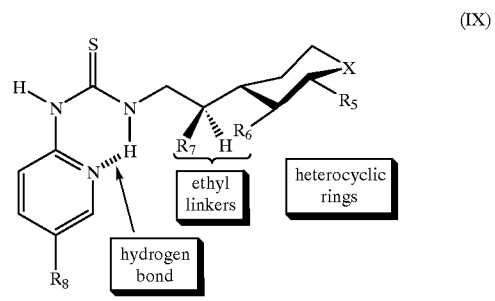

(IX)

The R's can be the same or different, and represent points of optional substitution. $R_5$, $R_6$, and $R_7$ can be hydrogen, or can be substituted, with a non-hydrogen atom group such as halo (Br, Cl, F, I), alkyl, alkenyl, hydroxy, alkoxy, thioalkyl, thiol, phosphino, ROH, or $RNH_2$ group, where R is alkyl. Preferably, one or more is alkyl, halo, or alkoxy. Preferred halogens are F, Br, or Cl. One or more of R, $R_6$, and $R_7$ can be a $C_1$–$C_3$ alkoxy, e.g., methoxy.

$R_6$ and/or $R_7$ are preferably a 3 or 4 (non-hydrogen)-atom group. $R_6$ and $R_7$ can be a group having 1 to 4 non-hydrogen atoms, whereas $R_5$ preferably is a group having 1 to 3 non-hydrogen atoms. $R_8$ can be a group of about 7 non-hydrogen atoms, or up to about the size of a phenyl ring. $R_8$ can be hydrogen, halo, alkyl, alkenyl, hydroxy, alkoxy, thioalkyl, thiol, phosphino, aryl, aralkyl, —$CH_2Ph$, alkoxy, ROH or $RNH_2$, where R is alkyl. $R_8$ can be X—R, where X is a bridging atom, including, but not limited to, C, S, O, N and P.

X can be CR'R", NR'", or O, where R', R", and R'" can be hydrogen, halo, alkyl, alkenyl, hydroxy, alkoxy, thioalkyl, thiol, or phosphino group. In one embodiment, $R_5$, $R_6$, R', R", and R'" are each hydrogen. In an alternative embodiment, X is CR'R" and at least one of R' and R" are fluoro, chloro, bromo, hydroxy, methoxy, or C1–3 alkyl. In a preferred embodiment, $R_8$ is bromine, and at least one of $R_5$, $R_6$, and $R_7$ is fluoro, chloro, or methoxy.

Preferred compounds include a larger functional group near the ethyl linker, for example $R_7$ acetamide or methoxy. Also preferred is a bulkier heterocyclic ring such as a bulky piperidinyl ring or an ortho/meta substituted pyridyl ring.

Specific PETT derivatives of the invention include:
N-[2-(1-piperidinoethyl)]-N'-[2-(5-bromopyridyl)] thiourea,
N-[2-(2,5-dimethoxyphenethyl)]-N'-[2-(5-bromopyridyl)]thiourea,
N-[2-(o-Chlorophenethyl)]-N'-[2-(5-bromopyridyl)] thiourea
N-[2-(o-Fluorophenethyl)]-N'-[2-(5-bromopyridyl)] thiourea, and
N-[2-(m-Fluorophenethyl)]-N'-[2-(5-bromopyridyl)] thiourea.

Other specific compounds of the invention are described in the Examples below.

DABO Compounds:

In another embodiment of the invention, the compounds are derivatives of DABO, and have the following general formula (X):

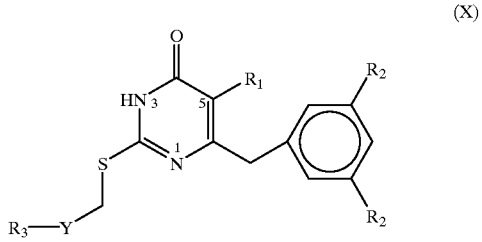

$R_1$ and $R_2$ can be alike or different, and can be hydrogen, halo, alkyl, alkenyl, hydroxy, alkoxy, thioalkyl, thiol, phosphino, ROH, or RNH group, where R is alkyl. Preferably, one or more of $R_1$ and $R_2$ is a $C_{1-3}$ alkyl, such as methyl (Me), ethyl (Et), or isopropyl (i-Pr). Preferably, $R_1$ is alkyl, alkenyl, ROH, or $RNH_2$. $R_2$ is preferably halo, alkyl, or C1–3 alkoxy.

Y can be S or O, and is preferably S. $R_3$ can be alkyl, alkenyl, aryl, aralkyl, ROH, or RNH group, where R is alkyl, and is preferably C1–3 alkyl.

Specific DABO compounds of the invention include:
  5-isopropyl-2-[(methylthiomethyl)thio]-6-(benzyl)-pyrimidin-4-(1H)-one.

Other specific compounds of the invention are described in the Examples below.

HEPT Compounds:

In another embodiment, the compounds of the invention are HEPT derivatives having the formula (XI):

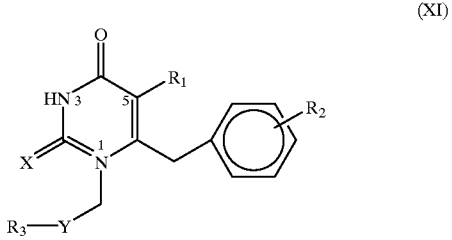

X and Y can be independently S or O. Preferably, at least one of X and Y is S. More preferably, X is S, and in specific embodiments, both X and Y are S.

$R_1$ and $R_2$ can be hydrogen, halo, alkyl, alkenyl, hydroxy, alkoxy, thioalkyl, thiol, phosphino, ROH, or RNH group, where R is alkyl. $R_3$ can be H, alkyl, alkenyl, aryl, aralkyl, ROH, or RNH group, where R is alkyl. Preferably, $R_1$ is alkyl, alkenyl, ROH, or $RNH_2$, and can be, for example, methyl, ethyl, or isopropyl. $R_2$ is preferably halo, alkyl, or $C_{1-3}$ alkoxy, and is preferably in the ortho or meta position. $R_2$ can be Br, F, Cl, or O—Me.

Specific HEPT compounds of the invention include:
  6-benzyl-5-isopropyl-1[(methylthio)methyl]-2-thiouracil.

Other specific compounds of the invention are described in the Examples below.

The compounds of the invention have the ability to inhibit replication of a retrovirus, such as human immunodeficiency virus (HIV), preferably with an $IC_{50}$ of less than 50 $\mu$M, for example, as determined by p24 enzyme immunoassay described in the Examples below. More preferably, the compound of the invention inhibits replication of HIV in the p24 assay with an $IC_{50}$ of 1 to 5 $\mu$M, or less. Most preferably, the compound inhibits replication of HIV in the p24 assay with an $IC_{50}$ of less than 5 nM. In some embodiments, the compound inhibits replication of HIV in the p24 assay with an $IC_{50}$ of less than 1 nM.

The invention provides a composition comprising a compound or inhibitor of the invention, and optionally, an acceptable carrier. The composition can be a pharmaceutical composition. Compositions of the invention are useful for prevention and treatment of retroviral infection, such as HIV infection.

Methods of Using Compounds of the Invention

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

Due to the ability to inhibit replication of retrovirus and to inhibit retroviral RT activity, the invention provides a method for treating or preventing retroviral infection, such as HIV infection, and a method for treating AIDS or AIDS-related complex (ARC). The method comprises administering to a subject an effective inhibitory amount of a compound of the invention or a pharmaceutically acceptable salt of the compound. The compound or inhibitor of the invention is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The compounds of the invention can be administered orally, parentally (including subcutaneous injection, intravenous, intramuscular, intrastemal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquify or dissolve in the rectal cavity to release the drug.

Dosage levels of approximately 0.02 to approximately 10.0 grams of a compound of the invention per day are useful in the treatment or prevention of retroviral infection, such as HIV infection, AIDS or ARC, with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The compound of the invention can be administered in combination with other agents useful in the treatment of HIV infection, AIDS or ARC. For example, the compound of the invention can be administered in combination with effective amounts of an antiviral, immunomodulator, anti-infective, or vaccine. The compound of the invention can be administered prior to, during, or after a period of actual or potential exposure to retrovirus, such as HIV.

Strategies for Design and Synthesis of Inhibitors

It has been proposed that NNI interfere with reverse transcription by altering either the conformation or mobility of RT rather than directly preventing the template-primer binding (Tantillo, C. et al., *J Mol Biol*, 1994, 243, 369–387). Specifically, binding of NNI to the NNI binding site (approximately 10 Å away from the polymerase catalytic site) inhibits RT by interfering with the mobility of the "thumb" and/or position of the "primer grip" (residues 229–231), which interact with the DNA primer strand (FIG. 1A).

Computer programs can be used to identify unoccupied (aqueous) space between the van der Waals surface of a compound and the surface defined by residues in the binding site. These gaps in atom-atom contact represent volume that could be occupied by new functional groups on a modified version of the lead compound. More efficient use of the unoccupied space in the binding site could lead to a stronger binding compound if the overall energy of such a change is favorable. A region of the binding pocket which has unoccupied volume large enough to accommodate the volume of a group equal to or larger than a covalently bonded carbon atom can be identified as a promising position for functional group substitution. Functional group substitution at this region can constitute substituting something other than a carbon atom, such as oxygen. If the volume is large enough to accommodate a group larger than a carbon atom, a different functional group which would have a high likelihood of interacting with protein residues in this region may be chosen. Features which contribute to interaction with protein residues and identification of promising substitutions include hydrophobicity, size, rigidity and polarity. The combination of docking, $K_i$ estimation, and visual representation of sterically allowed room for improvement permits prediction of potent derivatives.

Design of HEPT Derivatives

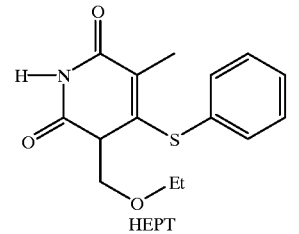

HEPT

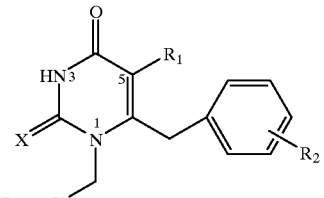

R1 = alkyl, alkene, ROH, or RNH$_2$
R2 = ortho and/or meta alkyl and/or halogen group
R3 = alkyl, alkene, phenyl, ROH, or RNH$_2$
X and Y = O or S
Potential modification sites for HEPT New HEPT derivative designs included compounds with added groups at the N-1 (Y-R$_3$) and C-5 (R$_1$) positions and those having oxygen (X or Y) atoms replaced by sulfur. Substitution of oxygen by sulfur can aid binding by decreasing the desolvation energy involved in binding. The modifications were made such that the HEPT derivative would fit favorably into the butterfly-shaped RT-NNI binding site, (See FIG. 2A) with the benzyl ring residing in one wing and thymine ring in the other. For all designed compounds, the benzyl ring is near Trp229 and the N-1 group is near Pro236, a typical position observed in crystal structures. The modeling calculations, along with the application of the constructed binding pocket, provided a guideline for the synthesis of lead compounds designed to have potent anti-HIV activity. The choice of compounds was also based on synthetic feasibility.

The region of the NNI site of HIV-1 RT located near the thymine ring nitrogen N-1 of the HEPT analogs contains a Pro236 loop region which is large enough to accommodate N-1 substituents. When an inhibitor binds to the NNI site of HIV-1 RT, the presence of a hydrophobic N-1 substituent could influence the Pro loop of this flexible region and provide additional hydrophobic contact leading to stronger binding. Docking results indicated that substitution at N-1 also helps the molecule position itself to achieve the best fit within the pocket.

The LUDI analysis showed a substantial increase in contact (lipo score) between the compound and the pocket and the calculation suggested an increase in hydrophobic contact and stronger binding when the substituent on the N-1 tail (R$_3$) is larger in size than a methyl moiety.

The Tyr183 residue of the HIV-1 RT is located in the catalytic region which has a conserved YMDD motif characteristic of reverse transcriptases. Therefore, the displacement of this tyrosine residue can interfere with catalysis and render the HIV-1 RT protein inactive. It has been suggested that bulky substituents at the 5th position of the thymine ring (RI) could indirectly accomplish this goal by displacing Tyr181 which is near Tyr183. The composite binding pocket shows sufficient room for at least a 3-carbon group in this region. The addition of a methyl, ethyl or isopropyl group on the 5th position of the thymine ring would lead to a higher affinity for the relatively hydrophobic environment.

LUDI analysis showed that the hydrophobic contact increases as hydrophobic groups at the 5th position ($R_1$) get bulkier. As it binds to the site, the ethyl or isopropyl group causes the nearby Tyr181 residue to rotate away from the inhibitor. This change in conformation in turn affects the positions of the neighboring Tyr183 and Tyr188 which can lead to the inactivation of HIV-1 RT.

DABO Derivatives

Figure 7A:
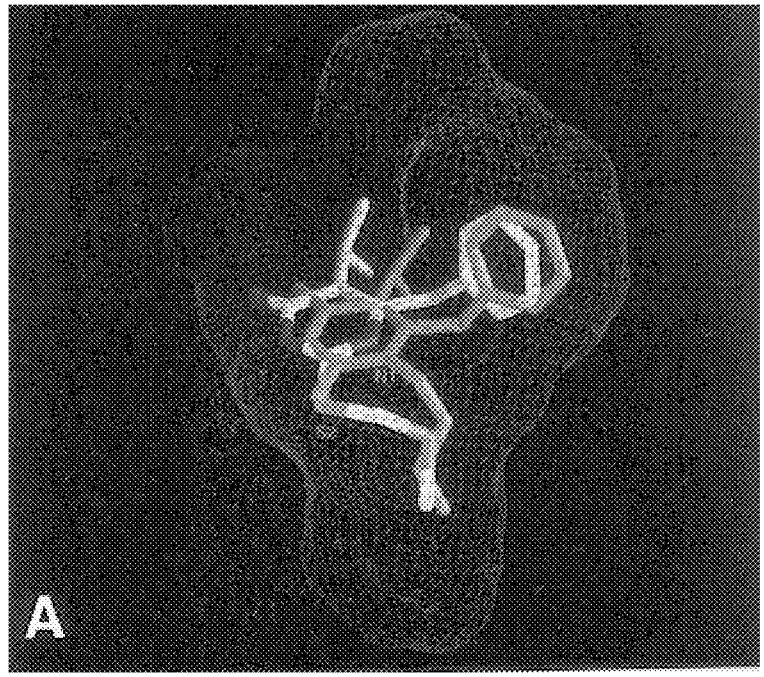
FIG. 7A is a view of the composite binding pocket of the NNI active site of HIV-1 RT. The DABO compound 3c is superimposed in the NNI composite binding site of the crystal structure of the RT/MKC-442 complex (hydrogen atoms not shown). MKC-442 (from crystal structure) is shown in pink, and compound 3c (from docking calculations) in multicolor. Compound 3c was docked into the active site of the RT/MKC complex (PDB access code: rt1) and then superimposed into the NNI composite binding pocket based on the matrix used in the pocket construction. The S2 substituent of the DABO compound 3c occupies the same region of the binding pocket as the N1 substituent of the HEPT derivative MKC-442.

Detailed analysis of HEPT binding revealed that the NI substituents of HEPT derivatives occupy the same region of the binding site as the thio (S2) substituents of DABO compounds (See FIG. 7A). Therefore, new DABO derivatives were designed and their binding into the NNI site of RT modeled using the crystal structure coordinates of the RT/MKC complex (pdb access code: rt1) and a molecular docking procedure. The final coordinates of the docked molecules were then superimposed into the composite binding pocket to evaluate the fit within the RT NNI pocket. Notably, multiple sterically allowed unoccupied spatial gaps in the binding site were identified from the docking studies which could be filled by strategically designed functional groups (See FIG. 7B).

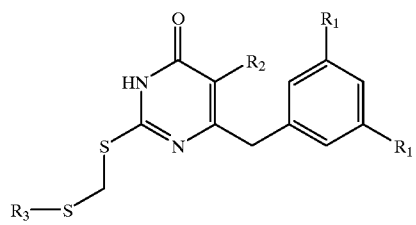

R1 = alkyl, alkene
R2 = alkyl, alkene, alcohol, amine, halogen
R3 = alkyl, alkene, alcohol, amine, phenyl
Potential modification sites of DABO The docked DABO molecule showed significant space surrounding the 6-benzyl ring and the 5th position of the thymine ring, which led to our design and synthesis of new DABO derivatives. Specific DABO compounds are discussed more fully in the Examples, below.

PETT Derivatives

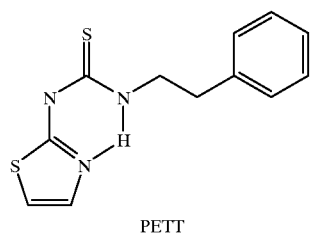

PETT

-continued

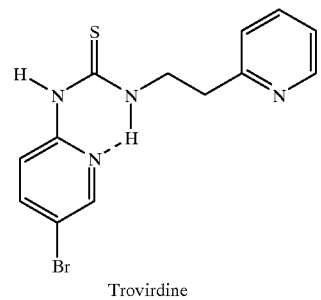

Trovirdine

Each PETT derivative described in the Examples below, can be viewed as two chemical groups linked together by a thiourea group. Upon binding RT, the PETT derivative fits into the butterfly-shaped binding site. (See FIG. 6). One half of the molecule is composed of a pyridyl thiourea group (compounds I-1 to 4, II-1 to 9, and III-1 to 3) or a 2-aminothiazole group (PETT) which forms an intramolecular hydrogen-bonded 6-membered heterocyclic ring (shown below). The other half of the molecule is a piperidinyl ring (II-9), a pyridyl ring (trovirdine), or a phenyl ring separated from the thiocarbonyl group by an ethyl linker.

The positions of the compounds having stronger binding and higher scores (evaluated by LUDI function) all fall into the butterfly-shaped binding region with one part residing in Wing 1 and the other in Wing 2, as illustrated in FIG. 1 B. For these compounds the ring closest to the thiocarbonyl group is near the Lys(K) 101 loop and the other pyridyl ring is near Trp(W)229 derivatives.

Figure 5A:
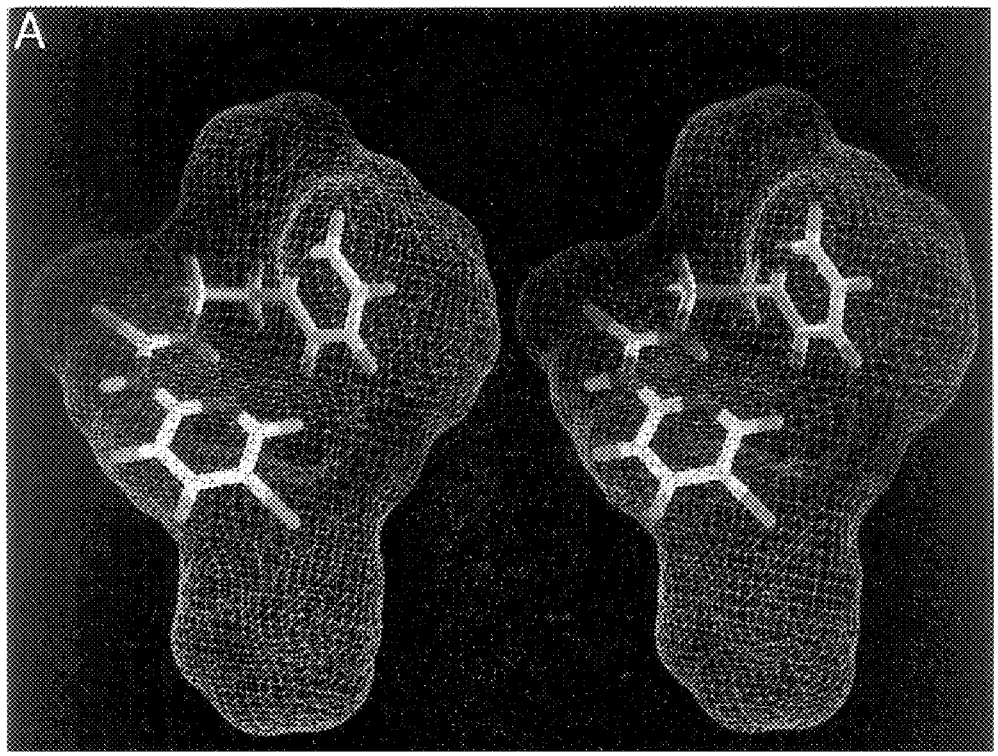
FIG. 5A shows a stereoview of compound trovirdine in the composite binding pocket which was constructed from combined coordinates of RT complexed with nine different NNI compounds.

Analysis of trovirdine, revealed multiple sites which can be used for the incorporation of larger functional groups. In the composite binding pocket, the docked trovirdine molecule showed a lot of usable space surrounding the pyridyl ring, ($R_2$–$R_6$), the ethyl linker ($R_7$) and near the 5-bromo position ($R_8$). (See FIG. 5A)

(II)

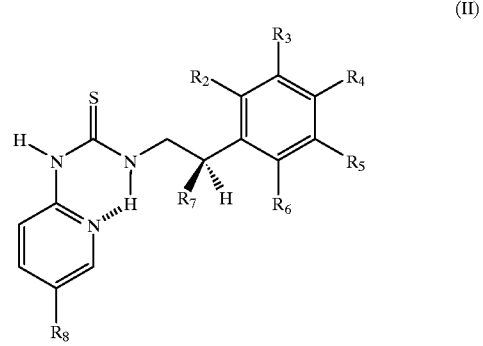

Efficient use of this space by strategically designed functional groups would lead to high affinity binding and ultimately result in better inhibitors. Our modeling studies suggest that designs using the space available in these regions, including (1) substitutions at $R_2$–$R_6$; (2) substituting heterocyclic rings for the pyridyl ring of trovirdine; (3) substitutions at $R_7$; (4) substitutions at $R_8$; and (5) maintaining the intramolecular hydrogen bond. As shown in the Examples below, modifications in these areas lead to potent RT inhibitors.

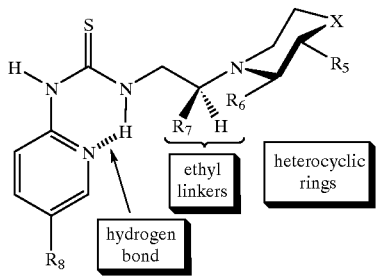

Advantages of the Invention

The invention provides a model for the three-dimensional structure of the RT-DNA complex based on the available backbone structure of RT-DNA complex and full structure of RT complexed with several NNI compounds. This is the first model to combine structural information from several complexes into a single composite and provides a suitable working model for the development of novel inhibitory compounds. The use of multiple NNI binding site coordinates from RT-NNI structures, as disclosed herein, permits the generation of a composite molecular surface. Analysis of the composite NNI binding pocket of the invention reveals that the binding pocket is surprisingly and counter-intuitively larger (instead of smaller) and more flexible (instead of more rigid) than expected. This composite NNI binding pocket serves as a guide for the synthesis and analyses of structure-activity relationships for the identification and design of new and more potent NNI of RT. The composite binding pocket additionally provides a model for the design of derivatives of NNIs for which crystal structure information is not available (e.g., PETT, DABO).

The compounds of the invention are useful for inhibition of RT activity and for inhibition of retroviral replication. The compounds disclosed herein provide more potent NNI of RT than known HEPT, DABO and PETT derivatives. With all strategies combined, a number of sites are identified for developing more potent derivatives of PETT, such as the incorporation of a larger functional group near the ethyl linker of PETT. Hitherto unknown piperidinyl substituted and piperozinyl substituted, as well as morpholinyl substituted PETT derivatives are disclosed which show potent anti-HIV activity at nanomolar concentrations.

In addition, the compounds of the invention provide a higher selectivity index (S.I.>$10^5$) than currently available anti-HIV compounds. This high S.I. permits more effective antiviral activity with a minimum of adverse cytotoxic effects.

EXAMPLES

The following examples are presented to illustrate the present invention and to assist one of ordinary skill in making and using the same. The examples are not intended in any way to otherwise limit the scope of the invention.

Example 1

Modeling Procedure
Construction of the Composite NNI binding pocket

A novel model of the NNI binding pocket of RT was constructed by superimposing nine individual RT-NNI crystal structures and then generating a van der Waals surface which encompassed all of the overlaid ligands. This "composite binding pocket" surprisingly reveals a different and unexpectedly larger NNI binding site than shown in or predictable from any of the individual structures and serves as a probe to more accurately define the potentially usable space in the binding site (FIG. 2A).

Modeling studies were based on the construction of a binding pocket which encompassed the superimposed crystal structure coordinates of all known RT-NNI complexes, including nine different structures of RT complexed with HEPT, MKC, TNK, APA, Nevirapine, N-ethyl Nevirapine derivative, 9-Cl TIBO (Ren, J. et al., Structure, 1995, 3, 915–926); 9-Cl TIBO (Das, K. et al., J. Mo. Biol., 1996, 264, 1085–1100) and 8-Cl-TIBO (PDB access codes rti, rt1, rt2, hni, vrt, rth, rev, tvr, and hnv, respectively).

The "thumb" region of RT complexes are relatively variable compared with the "palm" region. Therefore, a total of 117 C-alpha atoms of the residues from 97 to 213 which cover part of the NNI binding site and the "palm" region were used for a least-squares superimposing procedure within the program O (Jones, T. A. et al., Acta Crystallogr. A., 1991, 47, 110–119). Each coordinate set was superimposed onto the same initial coordinate set (RT/9-Cl TIBO). the distance between the pair was minimized by rotating and translating one coordinate set onto the other, minimizing distances between x, y, and z coordinates, according to the method of the program "O". The root mean square (RMS) values of the coordinates of the atoms being superimposed are shown to be 1.00, 0.98, 0.99, 0.62, 0.80, 0.87, 0.94 and 0.65 Å for HEPT, MKC, TNK, APA, Cyclopropanyl Nevirapine, N-ethyl Nevirapine derivative and two 9-Cl TIBO compounds, respectively. Next, the coordinates of the corresponding inhibitor molecules were then transformed according to the same matrices derived from the superimposition. Lastly, the overlaid coordinates of all inhibitors were read into the program GRASP (Nicholls, A., GRASP 1992, New York), from which an overall molecular surface was generated providing a binding pocket encompassing all inhibitors.

As shown in FIG. 2A, the surface of the binding pocket was color coded to reflect characteristics of the overlaid inhibitors, such as hydrogen bonding, hydrophilic, and hydrophobic regions. The amide nitrogens on the uracil ring of HEPT and TIBO derivatives are colorcoded red for hydrogen bonding atoms. Oxygen or sulfur atoms of carbonyl, thiocarbonyl, and ester groups, nitrogen atoms of amine groups, and halogen atoms are color-coded blue for polar (hydrophilic) groups. Carbon atoms are considered hydrophobic and are colored grey. This pocket, referred to as the composite binding pocket, was used as a basis for the analysis of inhibitor binding.

To generate the coordinates of the composite binding pocket using the InsightII program, each data point of the net defining the surface of the pocket was represented as a water molecule and was saved in Brookhaven Protein Databank (pdb) format. To provide a visual frame of reference, the coordinates have been superimposed on the pdb coordinates of an existing crystal structure having pdb access code hnv (HIV-1 RT/8-Cl TIBO complex). The coordinates of a composite binding pocket for HIV-1 RT generated by superimposing nine different NNI-RT complexes, are set forth in Table 9.

Docking and $K_i$ prediction

A computer simulation of the binding of PETT, DABO, and HEPT compounds into the NNI binding site of RT was accomplished using a molecular docking procedure. Docking of the compounds into the NNI binding site required the use of X-ray coordinates of an RT-NNI complex (RT/9-Cl-TIBO complex was used for modeling PETT, and the RT/MKC-442 complex was used for modeling DABO and HEPT). Upon binding to RT, the compound can fit into a butterfly-shaped NNI binding site (described by Ding et. al), Ding, J. et al., *Nat. Struct. Biol.*, 1995, 2, 407–415 (FIGS. 1B and 2A). Once the final docked position of the molecule in the NNI site was determined, the molecule was assigned a score (LUDD, from which an estimation of the inhibition constant ($K_i$ value) was determined.

After docking and $K_i$ estimation was completed for the inhibitors, evaluation of the docked compounds in the active site of RT involved placing each compound into the composite binding pocket using the same orientation matrix utilized in construction of the pocket. The potentially flexible regions in the binding site were then readily identified as were atom sites for future derivatization of the compounds. Fixed docking in the Affinity program within InsightII (InsightII, Molecular Simulations Inc., 1996, San Diego, Calif.), was used for docking small molecules to the NNI binding site which was taken from a crystal structure (PDB code rev, RT/9-Cl-TIBO complex). The program has the ability to define a radius of residues within a 5 Å distance from the NNI molecule. As the modeling calculations progressed, the residues within the radius were allowed to move in accordance with the energy minimization. Ten final docking positions were initially chosen for each inhibitor modeling calculation but failed to reveal more than two promising positions. Later, only two calculated positions were set for the search target.

Calculations were carried out on a Silicon Graphics INIDIGO$^2$ using the CVFF force field in the Discover program and a Monte Carlo search strategy in Affinity (Luty, B. A. et al., *J. Comp. Chem.*, 1995, 16, 454–464). No solvation procedures were used. Since the total number of movable atoms exceeds 200, Conjugated Gradient minimization was used instead of the Newton minimization method. The initial coordinates of the compounds were generated using the Sketcher module within InsightII. Each final docking position was then evaluated by a score function in LUDI. The top scoring model was then compared with the composite binding pocket and the known crystal structure of similar compounds and used for further analyses. The inhibitory constants ($K_i$ values) of the positioned NNI compounds were evaluated using the LUDI score function (Bohm, H. J., *J. Comput. Aided Mol. Des.*, 1994, 8, 243–256; Bohm, H. J., *J. Comput. Aided. Mol. Des.*, 1992, 6, 593–606).

Several modifications were imposed during the calculation of inhibitory constants ($K_i$ values) of the positioned compounds using the LUDI score function (Bohm, H. J. 1994 supra; Bohm, H. J. 1992 supra). First, the molecular surface areas (MS) were directly calculated from the coordinates of the compounds in docked conformations using the MS program. Second, the number of rotatable bonds (NR), which was assessed inaccurately by INSIGHTII (rigidity imposed by hydrogen bonding was not accounted for in the program), was re-evaluated. Third, it was assumed that the conserved hydrogen bond with RT was assumed to not deviate significantly from the ideal geometry. This assumption was supported by the fact that in the known crystal structures of RT complexes, all hydrogen bonds between NNIs and RT are near the ideal geometry. Last, for the trovirdine compounds, an additional penalty was imposed for a charged group or halogen atoms when positioned near the ring plane of a protein residue such as tryptophan 229 because the interaction was not adequately accounted for in the LUDI score. The working modification of the LUDI scoring function for the PETT compounds included subtracting a score of P from the total LUDI score when the ring plane of the Trp229 was within 5 Å from a para substituent (R):

LUDI Score=$MS*BS*2.93+85$ ($H$-bond)$-NR*24.2-100-P$;

where

P=200, when R=a hydrophilic group, e.g. —OH or —NO2;

P=100, when R=a para-halogen atom, e.g. —F, —Cl or —Br;

P=50, when R=a para-methoxy, e.g. —OMe;

P=0, when R=a hydrophobic group, e.g. H, CH3;

Consequently, the $K_i$ values for the modeled compounds were more predictable than they would be without such modification (Bohm, H. J. 1994 supra; Bohm, H. J. 1992 supra).

Contact Surface and Gap Analysis

Independent of the composite binding pocket and as a follow-up to the docking procedure, computer programs were used to analyze the surface complementarity between the compounds and the binding site residues. This analysis provided another useful way to examine binding interactions, based solely upon the structure that was used for docking (RT/9-Cl TIBO for PETT and RT/MKC-442 for DABO and HEPT) (Das, K. et al., *J. Mol. Biol.*, 1996, 264, 1085–1100).

A number of computer programs were written to analyze the surface of the compounds in the NNI binding site of RT and to better visualize any spatial gaps between the compounds and nearby residues of the RT protein. The algorithm used in these programs was based on a series of cubic grids surrounding the compound, with a user-defined grid spacing. All cubes were coded based on the distance and the nature of the interaction with the protein residues and/or compound atoms. The cubes that overlap both protein and compound within the contact radius are displayed as spheres and were selected to represent the buried surface (user-defined contact radius was the van der Waals radius plus an uncertainty factor, dependent on the reliability of source coordinates). All other cubes that did not interact with protein residues and were within a certain distance from the compound were selected to represent the gap space (space unoccupied by compound or protein) and are displayed as rods.

Figure 3A:
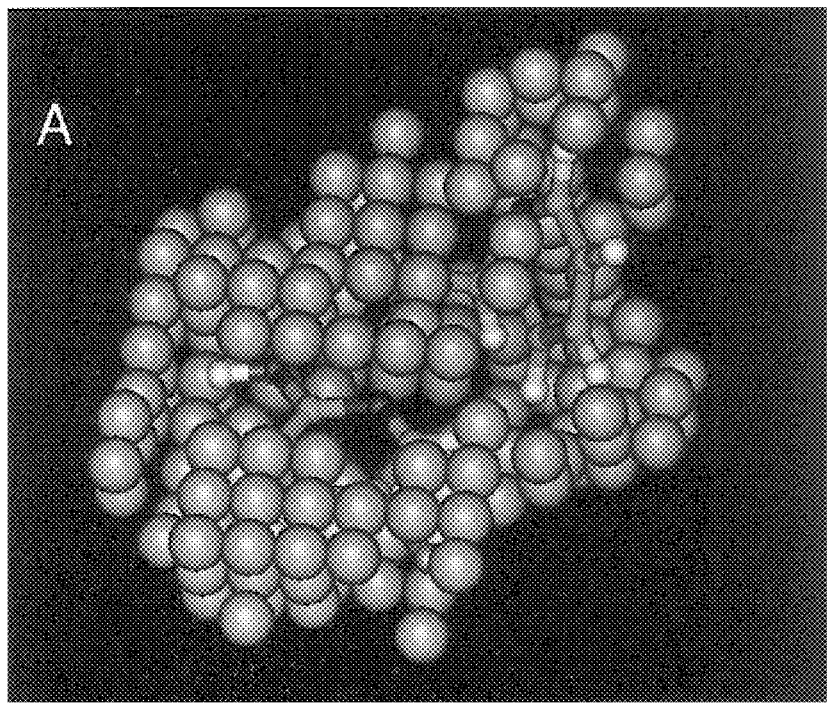
FIG. 3A shows a model of compound trouvirdine docked in the NNI binding site and color-coded by atom type. Spheres represent the sites of the molecular surface which are in contact with protein residues and are unavailable for future modification.

A graphic interface was then used to examine whether the "gap" spheres could be connected with the compounds without intersecting the "contact" spheres. If the criterion was met, the points that stemmed from the surface of the compound were defined as an expandable region (eligible for synthetic modification). The spheres generated by the programs (shown in FIG. 3) represent the sites buried by protein residues, indicating regions of the compound which are probably not available for derivatization.

Figure 4A:
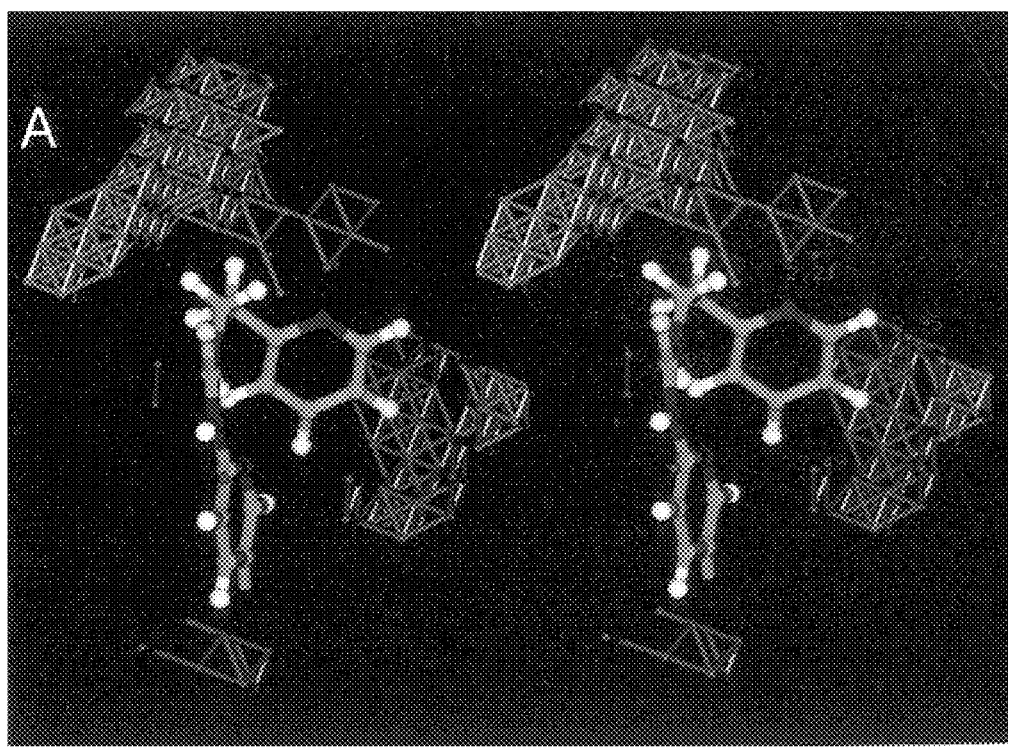
FIG. 4A shows a stereo model of compound I-2 and grid shown in red which represents gaps between the compound and protein residues (each red line=1 Å distance). Dashed lines show the nearest distance between an atom in the compound and the gap net which does not intersect the spheres shown in FIG. 3A.
Figure 4:
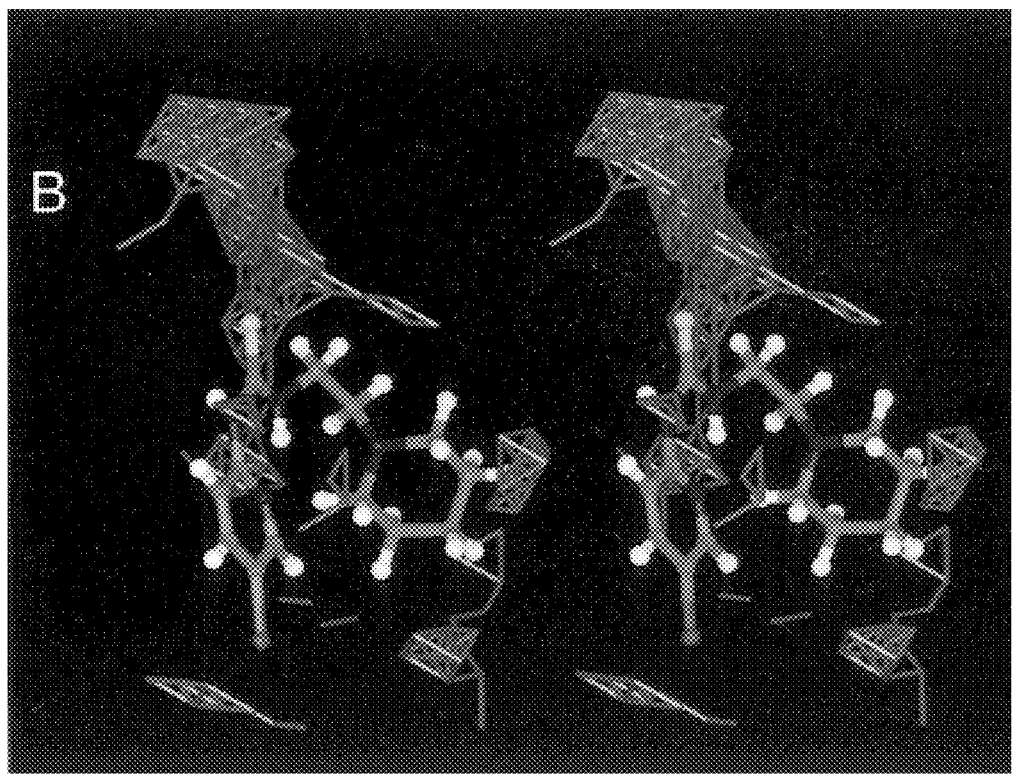
FIG. 4B shows a stereo model of PETT compound I-3 and grid shown in red which represents gaps between the compound and protein residues (each red line=1 Å distance). Dashed lines show the nearest distance between an atom in the compound and the gap net which does not intersect the spheres shown in FIG. 3B.

FIG. 4 shows the binding pocket embellished with a grid of red rods which represent unoccupied space between the compound and active site residues, providing a complementary view to that shown by the spheres. The grid illustrates the candidate sites for derivatization of the compound and, when used as a distance scale (the length of one rod represents 1 Å), also indicates the volume available for new functional groups.

One example of a useful program is the "SeeGap" program, whose code is listed below in Example 11, together with instructions for its use.

Composite NNI Binding Pocket of RT Reveals Protein Flexibility And Future Inhibitor Modification Sites The integrated structural information surprisingly revealed a much larger binding site than any shown in individual structures and served as a probe to define the potentially usable space in the binding site (FIG. 1). The three-dimensional binding site can be used as a reference point for the analysis of compounds which have been positioned by a docking procedure.

Upon inspection of the pocket it was apparent that although there are no large-scale conformational changes within the NNI binding site, a number of RT protein residues in contact with the inhibitors are relatively flexible and vary from structure to structure. These residues include Tyr180, Tyr181, Tyr318, Try319, Phe227, Leu234, Trp229, Pro95, and Glu138 (the latter from p51 subunit of RT).

Figure 2B:
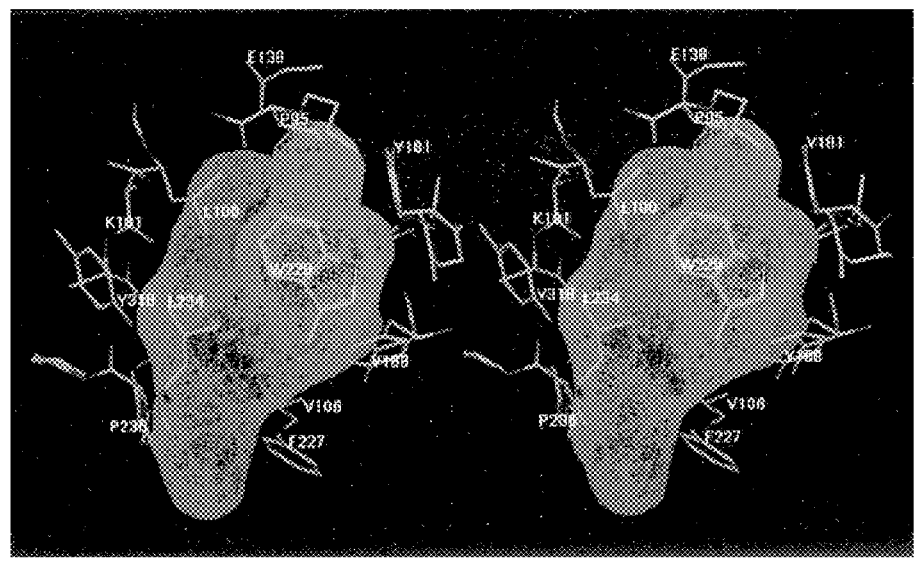
FIG. 2B shows a composite binding pocket (purple) superimposed on the active site residues of RT taken from the crystal structure coordinates of RT complexed with 8-Cl-TIBO (pdb access code: hnv). In the composite binding pocket, there are a number of regions which are larger than those defined by residues in individual crystal structures. Residues shown here which extend past the purple surface and toward the center of the binding site represent regions which are considered flexible and could be displaced by an appropriate inhibitor.

As shown in FIG. 2B, the surface of the composite binding pocket which is overlaid with the RT-TIBO binding site is a short distance (<1.5 Å) away from or even extends past RT residues 234–236, Y188, F227, and the backbone of K101. This indicates that these residues are flexible and can be displaced by the right substituent on an inhibitor.

The composite binding pocket of the invention, unlike a single crystal structure, is able to integrate the nature and extent of the flexibility of the active site residues in the NNI binding site of RT. This uniquely permits prediction of potential modification sites on PETT, DABO, and HEPT derivatives after positioning the compounds in the NNI active site of RT. The method for designing new NNI compounds was particularly useful given the fact that no known crystal structures exist for RT-PETT and RT-DABO complexes, a fact which in this case would prevent the successful application of traditional structure-based drug design methods. Importantly, the model was validated by experimentally demonstrating the superior potency of newly designed agents, predicted to have strong RT inhibitory activity, based upon the low $K_i$ values estimated.

Example 2

Predicted Efficacy of HEPT Derivatives

Compounds listed in Table 1 have been modeled into the NNI binding site of RT (RT/MKC 422 complex) using the docking procedure. The modeled positions were compared with the composite binding pocket of the invention, having the coordinates set forth in Table 9. Modeling was followed by analysis with the LUDI score function.

All of the positions of the compounds with top scores fall into the butterfly-shaped binding site, with the benzyl ring residing in wing 1 and the thymine ring in the wing 2 (FIG. 2). For all compounds tested, the benzyl ring is near Trp229 and the N-1 group is near Pro236, a typical position observed in crystal structures (FIG. 1B). The trend of calculated values listed in Table 1 shows that the $K_i$ value decreases as a result of three factors: para substituents (R2) removed from the benzyl ring, larger alkyl groups added to the thymine ring ($R_1$), and sulfur atoms substituted for oxygen (at X and/or Y). The modeling calculations, along with the application of the composite NNI binding pocket, provided a guideline for the synthesis of lead compounds designed to have potent anti-HIV activity. The choice of compounds was also based on synthetic feasibility.

TABLE 1

Results of modeling calculations for HEPT derivatives

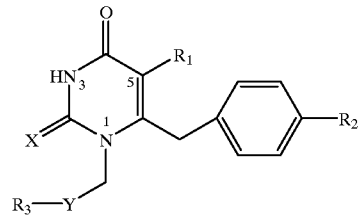

| X | Y | $R_1$ | $R_2$ | $R_3$ | NR[a] | Accessible Surface (Å$^2$) | Molecular surface (Å$^2$) | Buried Surface (%) | LUDI Score (Lipo) | LUDI Score[d] (Sum) | KI[d] (μM) |
|---|---|---|---|---|---|---|---|---|---|---|---|
| O | O | Et | F | Et | 6 | 549 | 296 | n.d. | n.d. | n.d. | n.d. |
| O | O | Et | Br | Et | 6 | 576 | 311 | n.d. | n.d. | n.d. | n.d. |
| S | O | Me | OMe | Et | 6 | 558 | 303 | n.d. | n.d | n.d. | n.d. |
| O | O | Me | H | Et | 5 | 505 | 269 | 85 | 599 | 463 | 23 |
| O | O | Et | H | Et | 6 | 528 | 284 | 87 | 661 | 501 | 9.8 |
| O | O | i-Pr | H | Et | 6 | 541 | 294 | 88 | 688 | 528 | 5.2 |
| S | O | Me | H | Et | 5 | 512 | 275 | 87 | 703 | 567 | 2.1 |
| S | O | Et | H | Et | 6 | 536 | 290 | 90 | 732 | 572 | 1.9 |
| S | O | i-Pr | H | Et | 6 | 550 | 300 | 89 | 741 | 580 | 1.5 |
| S | S | Me | H | Et | 5 | 521 | 283 | 86 | 706 | 570 | 2.0 |
| S | S | Et | H | Et | 6 | 545 | 297 | 90 | 756 | 595 | 1.1 |
| S | S | i-Pr | H | Et | 6 | 557 | 308 | 90 | 777 | 617 | 0.68 |
| S | S | Me | H | Me | 4 | 491 | 266 | 84 | 661 | 549 | 3.2 |

TABLE 1-continued

Results of modeling calculations for HEPT derivatives

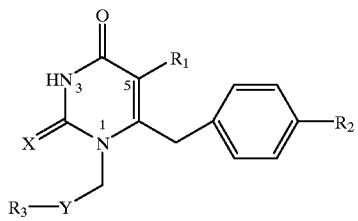

| X | Y | R₁ | R₂ | R₃ | NR$^a$ | Accessible Surface (Å$^2$) | Molecular surface$^b$ (Å$^2$) | Buried Surface$^c$ (%) | LUDI Score (Lipo) | LUDI Score$^d$ (Sum) | KI$^d$ ($\mu$M) |
|---|---|---|---|---|---|---|---|---|---|---|---|
| S | S | Et | H | Me | 5 | 514 | 280 | 88 | 703 | 567 | 2.1 |
| S | S | i-Pr | H | Me | 5 | 527 | 290 | 90 | 738 | 602 | 0.95 |

Me = methyl, Et = ethyl, i-Pr = isopropyl
n.d. (not determined) means high K$_i$ values resulting from energetically unfavorable rotation of Trp229 which sterically hinders binding in cases of the para substitution, as revealed by modeling.
$^a$NR = number of rotatable bonds in the compound. Used in the LUDI calculation to reflect the loss of binding energy due to freezing of internal degrees of freedom.
$^b$Molecular surface area calculated using the program GRASP, and defined as the boundary of the volume within any probe sphere (meant to represent a water molecule) of given radius sharing no volume with the hard sphere atoms which make up the molecule. The values are slightly smaller than the ones approximated by LUDI program. The accessible surface can be defined as the locus of the centers of all possible such probes in contact with the hard sphere atoms. Alternatively it can be defined as the hard sphere surface if each atomic radius is increased by the probe radius (1.4 Å radius).
$^c$Buried surface represents the percentage of molecular surface in contact with the protein calculated by LUDI based on the docked positions. Based on published crystal structures of RT complexes, the calculation shows that these values could be as low as 77% (in RT/HEPT complex) and can be as high as 90% (in RT/APA complex) but most of them including RT/MKC average around 84%. Therefore, the calculated values may be in the worst case slightly overestimated.
$^d$Ideal hydrogen bond distances and angles between the compounds and the protein are assumed in all cases for K$_i$ and Score (sum) calculation. In published crystal structures of RT complexes, hydrogen bond geometry's are indeed close to ideal; the amide carbonyl of residue A101 on a loop demonstrates a substantial flexibility which can accommodate the best geometry for hydrogen bonding.

Synthesis of HEPT Derivatives

The compounds listed in Table 1 above can be synthesized by reaction of substituted aryl acetonitriles and appropriately functionalized 2-bromo ethyl esters, for example in the presence of zinc in refluxing tetrahydrofuran. Products of the reaction are purified by gel chromatography. Generated 3-oxo esters are next converted into 5-alkyl-6-(arylmethyl)-2-thiouracils with chloroacetic acid, e.g., overnight to yield 5-alkyl-6-(arylmethyl)uracils. The final step in the synthesis is reaction of the uracil with hexamethyldisilazane (HMDS) in the presence of ammonium sulfate. Subsequent treatment with acetals and trimethyl silyl triflate in acetonitrile leads to the formation of N-'substituted uracil and thiouracil derivatives.

These and other known methods can be used to synthesize the compounds of the invention.

Example 3

DABO Derivatives

Chemical Synthesis

All chemicals were used as received from Aldrich Chemical Company (Milwaukee, Wisconsin). All reactions were carried out under nitrogen. Column chromatography was performed using EM Science silica gel 60 and one of the following solvents: ethyl acetate, methanol, chloroform, hexane, or methylene chloride. Nuclear magnetic resonance (NMR) spectra were recorded on a Varian (Palo Alto, Calif.) 300 MHz instrument (Mercury 2000 model) and chemical shifts ($\delta$) are reported in parts per million (ppm) relative to tetramethylsilane as an internal standard at 0 ppm. $^{13}$C NMR spectra were recorded at 75 MHz in CDCl$_3$ on the same instrument using a proton decoupling technique. The chemical shifts reported for $^{13}$C NMR are referenced to the chloroform triplet at 77 ppm. Melting points were measured using a Mel-Temp 3.0 (Laboratory Devices Inc., Holliston, Mass.) melting apparatus and are uncorrected. UV spectra were recorded from a Beckmann (Fullerton, Calif.) model DU 7400 UV/Vis spectrometer using a cell path length of 1 cm and methanol solvent. Fourier Transform Infrared spectra were recorded using an FT-Nicolet (Madison, Wis.) model Protege 460 instrument. Mass spectrum analysis was performed using a Hewlett-Packard (Palo Alto, Calif.) Matrix Assisted Laser Description time-of-flight (MALDI-TOF) spectrometer (model G2025A) in the molecular ion detection mode (matrix used was cyanohydroxycinnamic acid). Some samples were analyzed using a Finnigan (Madison, Wis.) MAT 95 instrument. Elemental analysis was performed by Atlantic Microlabs (Norcross, Ga.).

General Procedure for the synthesis of DABO compounds 3a–d:

The 5-alkyl-2-[(methylthiomethyl)thio]-6-(benzyl)-pyrimidin-4-(1H)-one derivatives 3a–d were prepared as shown in Scheme 1.

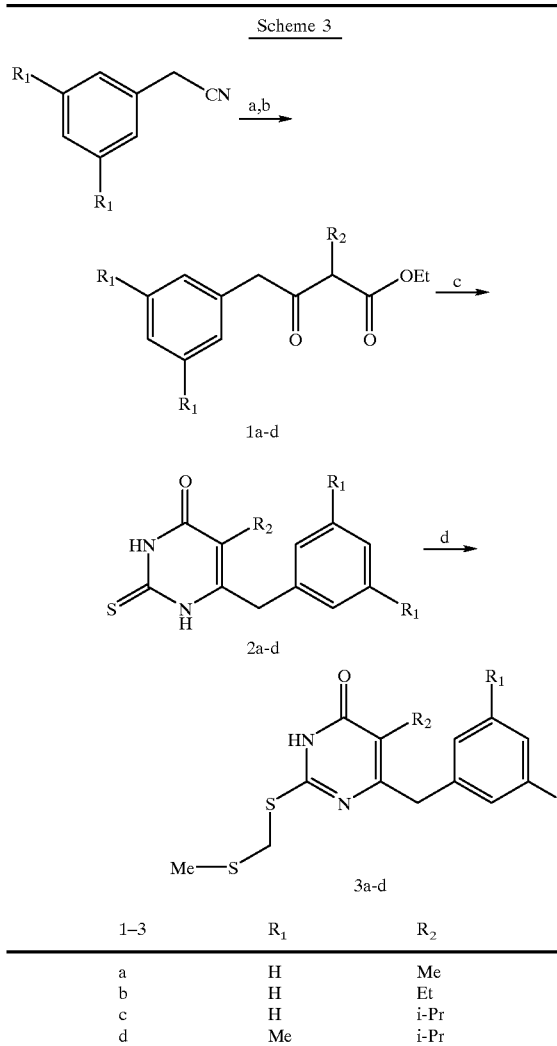

Reagents and conditions:
a R₂CHBrCOOEt/Zn/THF, b HCl(aq), c (H₂N)₂CS/Na/EtOH, d DMF, K₂CO₃, Chloromethyl methyl sulfide, 15 h.

Ethyl-2-alkyl-4-(phenyl)-3-oxobutyrates 1a–d were obtained from commercially available phenyl acetonitrile. The β-ketoesters were condensed with thiourea in the presence of sodium ethoxide to furnish the corresponding thiouracils 2a–d. Compounds (1a–d and 2a–d) were produced by a methods previously described (Danel, K. et al., *Acta Chemica Scandinavica*, 1997, 51, 426–430; Mai, A. et al., *J. Med. Chem.*, 1997, 40, 1447–1454; Danel, K. et al., *J. Med. Chem.*, 1998, 41, 191–198).

Subsequent reaction of thiouracil with methylchloromethyl sulfide in N,N-dimethylformamide (DMF) in the presence of potassium carbonate afforded compounds 3a–d in moderate yields A mixture of thiouracil compound 2 (1 mmol), methylchloromethyl sulfide (1 mmol), and potassium carbonate (1 mmol) in anhydrous DMF (5 ml) was stirred overnight at room temperature. After treatment with water (50 ml), the solution was extracted with ethyl acetate (3×50 ml). The combined extracts were washed with saturated NaCl (2×50 ml), dried (MgSO₄), filtered and concentrated in vacuo to give the crude products 3a–d which were purified by column chromatography (hexane:ethyl acetate eluent).

X-ray Crystallography

Yellow rectangular plates of compound 3b were grown from tetrahydrofuran by slow evaporation at room temperature. X-ray diffraction data for a 0.5×0.2×0.08 mm plate crystal of compound 3b was collected at room temperature using a SMART CCD X-ray detector (Bruker Analytical X-ray Systems, Madison, Wis.). Structure solution and refinement was performed using the SHELXTL suite of programs (Bruker Analytical X-ray Systems, Madison, Wis.). All nonhydrogen atoms were refined using anisotropic displacement parameters. Hydrogen atoms were placed at ideal positions and refined as riding atoms with relative isotropic displacement parameters.

Figure 8:
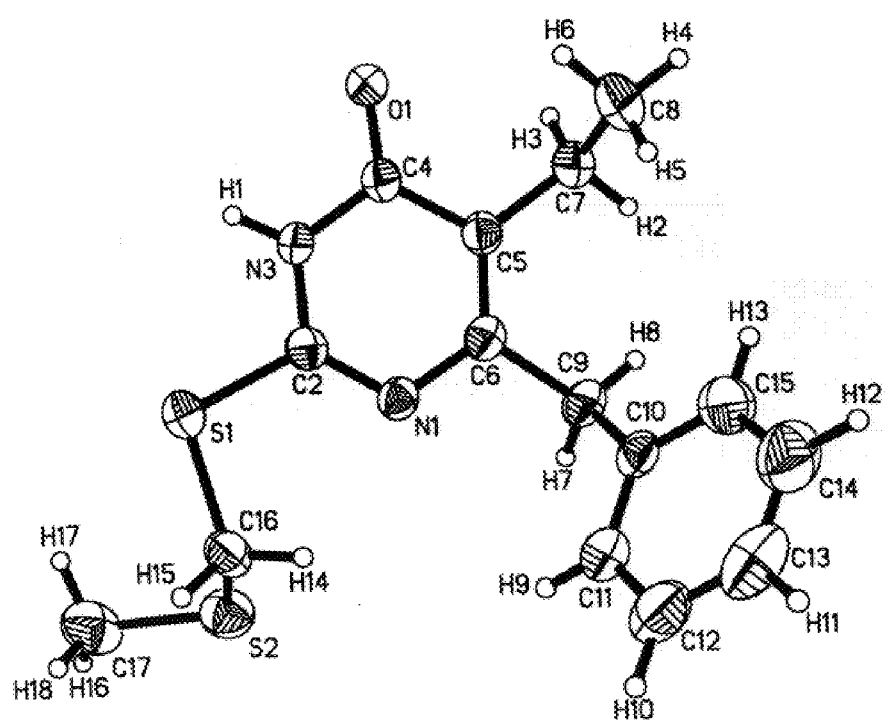
FIG. 8 is an ORTEP drawing of the room temperature X-ray crystal structure of DABO compound 3b (30% ellipsoids).

The refined small molecule X-ray crystal structure of compound 3b is shown as an Oak Ridge Thermal Ellipsoid Program (ORTEP) drawing in FIG. 8. Table 2 lists the crystal data and structure refinement statistics for compound 3b. Data was collected at room temperature ($\lambda=0.71073$ Å), refined using full-matrix least-squares refinement on $F^2$, and corrected for absorption using semi-empirical psi-scans.

TABLE 2

| | |
|---|---|
| Unit Cell | a = 4.7893(4)Å |
| | b = 10.8709(10)Å |
| | c = 30.040(3)Å |
| | α = 90° |
| | β = 92.474(2)° |
| | γ = 90° |
| Space Group | P2₁/n |
| Unit Cell Volume | 1562.5(2)Å³ |
| Z | 4 |
| θ range for data collection | 1.36 to 28.27° |
| Limiting indices | –6≤h≤6 |
| | –8≤k≤14 |
| | –39≤l≤37 |
| Reflections collected | 8744 |
| Independent reflections | 3507 (R$_{int}$ = 0.0486) |
| Data/restraints/parameters | 3507/0/183 |
| Goodness-of-fit on F² | 1.095 |
| Final R indices [I > 2σ(I)] | R1 = 0.0666, wR2 = 0.1384 |
| R indices (all data) | R1 = 0.1114, wR2 = 0.1569 |
| Absorption coefficient | 0.338 mm⁻¹ |
| Max. and min. transmission | 0.8356 and 0.6542 |
| Extinction coefficient | 0.0004(11) |
| Largest difference peaks | 0.279 and –0.211 eÅ⁻³ |

$R_{int} = \Sigma|F_o^2 - <F_o^2>|/\Sigma|F_o^2|, R1 = \Sigma||F_o| - |F_c||/\Sigma|F_o|$
$wR2 = \{\Sigma[w(F_o^2 - F_c^2)^2]/\Sigma[w(F_o^2)^2]\}^{1/2}$
$GooF = S = \{\Sigma[w(F_o^2 - F_c^2)^2]/(n - p)\}^{1/2}$, where n = reflections, p = parameters Physical Data Of Synthesized Compounds:
5-methyl-2-[(methylthiomethyl)thiol-6-benzyl-pyrimidin-4-1H-one (3a)

Yield 62%; mp 148–149° C.; ¹H NMR(CDCl₃):δ 2.10 (s, 3H), 2.14 (s, 3H), 3.91 (s, 2H), 4.29 (s, 2H), 7.29–7.26 (m, 5H), 12.20 (s, 1H); ¹³C NMR(CDCl₃):δ 10.7 (CH₃), 15.5 (SCH₃), 36.6 (CH₂Ph), 41.0 (SCH₂), 116.7 (C-5), 137.6–126.4 (Ph), 155.2 (C-6), 162.0 (C-4), 165.1 (C-2); CI-MS: 293.1 (M+1).

5-ethyl-2-[(methylthiomethyl)thio]-6-benzyl-pyrimidin-4-1H-one (3b)

Yield 65%; mp 124–126° C.; ¹H NMR(CDCl₃):δ 1.08 (t, 3H), 2.12 (s, 3H), 2.58 (q, 2H), 3.91 (s, 2H), 4.26 (s, 2H), 7.28–7.26 (m, 5H), 12.30 (s, 1H); ¹³C NMR(CDCl₃):δ 13.1 (CH₃), 15.4 (SCH₃), 18.7 (CH₂), 36.4 (CH₂Ph), 40.3 (SCH₂), 122.4 (C-5), 138.0–126.3 (Ph), 155.4 (C-6), 161.5 (C-4), 165.2 (C-2); Cl-MS: 307.1 (M+1).

5-isopropyl-2-[(methylthiomethyl)thio]-6-benzyl-pyrimidin-4–1H-one (3c)

Yield 57%; mp 116–117 C; ¹H NMR(CDCl₃):δ 1.22 (d, 6H), 2.07 (s, 3H), 3.03 (q, 1H), 3.88 (s, 2H), 4.21 (s, 2H), 7.24–7.13 (m, 5H), 12.43 (s, 1H); ¹³C NMR(CDCl₃):δ 15.4

(SCH$_3$), 19.6 (CH$_3$), 28.0 (CH), 36.3 (CH$_2$Ph), 40.9 (SCH$_2$), 125.3 (C-5), 138.3–126.3 (Ph), 155.5 (C-6), 161.1 (C-4), 164.5 (C-2); CI-MS 321.1 (M+1).

5-isopropyl-2-[(methylthiomethyl)thio]-6-(3,5-dimethylbenzyl)-pyrimidin-4-1H-one (3d)

Yield 67%; mp 116–120° C.; $^1$H NMR(CDCl$_3$):δ 1.28 (d, 6H), 2.15 (s, 3H), 2.27 (s, 6H), 3.10 (q, 1H), 3.88 (s, 2H), 4.31 (s, 2H), 6.84 (s, 3H), 12.42 (s, 1H); $^{13}$C NMR(CDCl$_3$):δ 15.3 (SCH$_3$), 19.6 (CH$_3$), 21.2 (CH$_3$), 28.0 (CH), 36.3 (CH$_2$Ph), 40.8 (SCH$_2$), 125.2 (C-5), 138.0–126.5 (Ph), 155.4 (C-6), 161.3 (C-4), 164.7 (C-2); CI-MS: 349.2 (M+1).

Figure 7B:
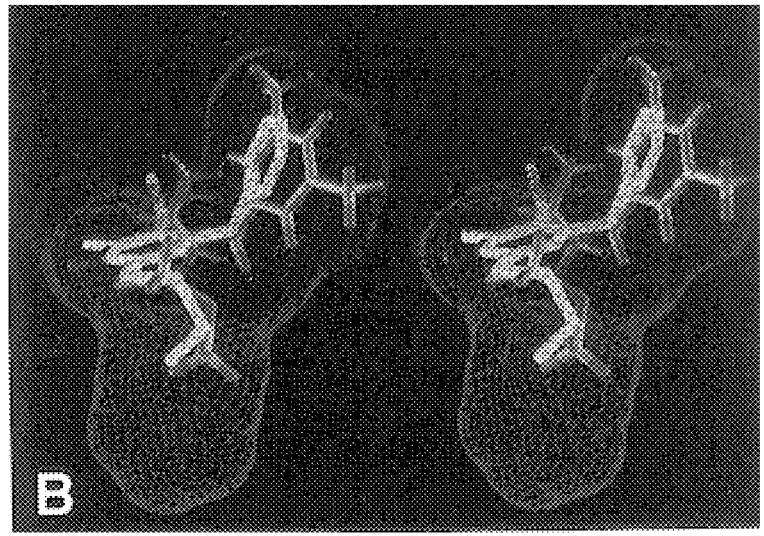
FIG. 7B is a view of the composite binding pocket of the NNI active site of HIV-1 RT. An X-ray crystal structure of DABO compound 3b is superimposed on the docked model of DABO compound 3d in the NNI composite binding pocket of RT, demonstrating their remarkably similar conformations.

Modeling and Design of DABO Compounds:

The calculated molecular coordinates of DABO compounds which were energy-minimized and docked into the NNI binding site adopted a conformation remarkably similar to that of the crystal structure of compound 3b. FIG. 7B shows the modeled coordinates superimposed on the crystal structure coordinates of 3b and illustrates their conformational similarity, suggesting that the final docked positions of the DABO compounds in the NNI pocket were energetically favorable and quite suitable for these studies. Multiple sterically allowed unoccupied spatial gaps in the binding site were identified from the docking studies which could be filled by strategically designed functional groups (FIG. 7B).

The docked DABO molecule (compound 3a) unexpectedly showed significant space surrounding the benzyl ring and the 5th position of the thymine ring, which led to design of compounds 3b, 3c and 3d. The inhibition constants of the docked molecules were calculated based on a LUDI score function and are listed in Table 3. The calculated $K_i$ values suggested that compounds 3c and 3d would be particularly active inhibitors of RT.

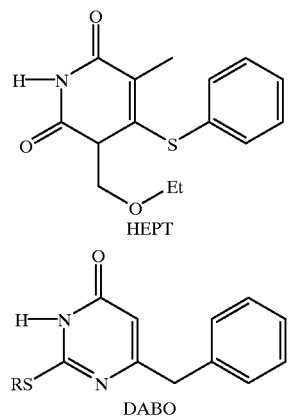

HEPT

DABO

Compound 3d, which differs from compound 3c by the addition of two methyl groups to the benzyl ring, provides more hydrophobic contact with the NNI binding pocket and was predicted to be more potent than compound 3c, based on the modeling studies. Calculations indicate that compounds 3a–3d have progressively larger molecular surface areas but still maintain approximately the same percentage of the molecular surface area in contact with the protein residues. Consequently, the calculated contact surface area between the protein and the compound increases in the following order: compound 3a, 3b, 3c, and 3d. This increased surface area in turn dictates a decrease in calculated $K_i$ values, with 3a having the worst value and 3d the best.

The Tyr183 residue of the HIV RT is located in the catalytic region which has a conserved YMDD motif characteristic of reverse transcriptases. Therefore, the displacement of this tyrosine residue can interfere with catalysis and render the HIV-1 RT protein inactive.

Bulky substituents at the 5th position of the thymine ring could indirectly accomplish such inactivation by displacing Tyr181 which is near Tyr183 (Ding, J. et al., Nat. Struct. Biol., 1995, 2, 407–415). The composite binding pocket shows sufficient room for at least a 3-carbon group at the 5th position. The addition of a methyl, ethyl or isopropyl group at the 5th position of the thymine ring is expected to lead to higher affinity for the relatively hydrophobic environment at this location of the binding pocket. The favorable hydrophobic contact increases as the hydrophobic group at the 5th position gets bulkier. As the DABO derivative binds to the site, the ethyl or isopropyl group can also cause the nearby Tyr181 residue to rotate away from the inhibitor.

Modeling studies showed that this change in conformation in turn affects the positions of neighboring Tyr183 and Tyr188 which may contribute to the inactivation of HIV-1 RT. The benzyl ring of compounds 3a–3d is located near a region surrounded by the hydrophobic ring planes of residues Trp229, Pro95, Y188 and Y181. The analysis of compounds 3a–3c in the composite binding pocket suggests that the benzyl ring would be located on the boundary of the pocket, near residue Y 188. A para substituent of the ring is situated perpendicular to the ring plane of nearby Trp229, within van der Waals contact, and leaves a lot of space unfilled between the compound and Pro95. With a slight conformational rotation of the benzyl ring, compound 3d, with the addition of two methyl groups, was found to better fill the composite binding pocket (FIG. 7B). Such observations indicate that further modifications to the benzyl ring could lead to even more potent inhibitors.

TABLE 3

Dabo Compounds

| Compound Number | R$_1$ | R$_2$ | M.S.[b] (Å$^2$) | B.S.[c] (%) | Lipo Score | Ludi[a] K$_i$ ($\mu$M) |
|---|---|---|---|---|---|---|
| 3a | H | Me | 275 | 88 | 709 | 3.3 |
| 3b | H | Et | 283 | 88 | 730 | 2.0 |
| 3c | H | i-Pr | 301 | 89 | 785 | 0.56 |
| 3d | Me | i-Pr | 329 | 89 | 875 | 0.05 |

[a]Ludi K$_i$ values were calculated based on the empirical score function in Ludi program (Bohm, H. J., J. Comput. Aided. Mol. Des., 1994, 8, 243–256; 1996). Ideal hydrogen bond distances and angles between compounds and protein are assumed in all cases for Ludi K$_i$ and Ludi Score calculation. In published crystal structures of RT complexes, hydrogen bond geometries are indeed close to ideal; the amide carbonyl of residue A101 on a loop demonstrates substantial flexibility which can accommodate the best geometry for hydrogen bonding. The number of rotatable bonds (= 2) is used in the Ludi calculation to reflect the loss of binding energy due to freezing of internal degrees of freedom.
[b]MS, molecular surface area calculated using Connolly's MS program (Connolly, M. L., Science, 1983, 221, 709–713). Defined as boundary of volume within any probe sphere (meant to represent a water molecule) of given radius sharing no volume with hard sphere atoms which make up the molecule. Values are slightly smaller than those approximated by Ludi program.

TABLE 3-continued

Dabo Compounds

| Compound Number | $R_1$ | $R_2$ | M.S.[b] ($Å^2$) | B.S.[c] (%) | Lipo Score | Ludi[a] $K_i$ ($\mu M$) |
|---|---|---|---|---|---|---|

[c]BS, buried surface: percentage of molecular surface in contact with protein calculated by Ludi relative to docked positions. Based on published crystal structures of RT complexes, the calculation shows that these values could be as low as 77% (in RT-HEPT complex) and can be as high as 90% (in RT-APA complex) but most of them including RT-MKC average around 84%.

Predictable Activities

The trend of the calculated $K_i$ values based on the modeling and on the use of the composite binding pocket, with surprising accuracy, predicted the trend of the experimentally determined $IC_{50}$ values from HIV replication assays. Compounds 3a–3d were tested for RT inhibitory activity in cell-free assays using purified recombinant HIV RT (listed as $IC_{50}$[rRT] in Table 4), as well as by in vitro assays of anti-HIV activity in HTLV$_{IIIB}$-infected peripheral blood mononuclear cells ($IC_{50}$[p24] in Table 4) (Zarling, J. M. et al., Nature, 1990, 347, 92–95; Erice, A. et al., Antimicrob. Ag. Chemother., 1993, 37, 835; Uckun, F. M. et al., Antimicrobial Agents and Chemotherapy, 1998, 42, 383).

Larger compounds which better fill the composite binding pocket and have lower calculated $K_i$ values showed better $IC_{50}$[rRT] values. This is reflected by the enhancement of the inhibitory activity with the addition of progressively larger groups such as methyl (3a), ethyl (3b), and isopropyl (3c) at the C-5 position of the thymine ring (see Table 4). The same trend was also observed for $IC_{50}$[p24] values.

The lead DABO derivative, 5-isopropyl-2-[(methylthiomethyl)thio]-6-(benzyl)pyrimidin-4-(1H)-one (compound 3c), elicited potent anti-HIV activity with an $IC_{50}$ value less than 1 nM for inhibition of HIV replication (measured by p24 production in HIV-infected human peripheral blood mononuclear cells) and showed no detectable cytotoxicity (inhibition of cellular proliferation was >100 $\mu$M as measured by MTA) (Table 4). In contrast to all previously published data for DABO and S-DABO derivatives which were less active than AZT and MKC-442 (Danel, K. et al., Acta Chemica Scandinavica, 1997, 51, 426–430; Mai, A. et al., J. Med. Chem., 1997, 40, 1447–1454; Danel, K. et al., J. Med. Chem., 1998, 41, 191–198) and showed selectivity indices of <1,000, the novel compound 3c was more than 4-fold more active than AZT and MKC-442, and abrogated HIV replication in peripheral blood mononuclear cells at nanomolar concentrations with an unprecedented selectivity index ($=IC_{50}$ [MTA]/$IC_{50}$[p24] ) of >100,000.

The X-ray crystal structure of 3b was determined to compare its conformation to that of the compound after docking into the NNI binding site. The refined small molecule X-ray crystal structure of compound 3b is represented as an ORTEP drawing in FIG. 8. The calculated molecular coordinates of DABO compounds which were energy-minimized and docked into the NNI binding site adopted a conformation remarkably similar to that of the crystal structure of compound 3b. FIG. 7B shows the modeled coordinates superimposed on the crystal structure coordinates of 3b and illustrates their conformational similarity, suggesting that the final docked positions of the DABO compounds in the NNI pocket were energetically favorable.

TABLE 4

Inhibitory Activity of DABO Compounds:

| Compound Number | $R_1$ | $R_2$ | $IC_{50}$ [rRT] ($\mu$M) | $IC_{50}$ [p24] ($\mu$M) | $CC_{50}$ [MTA] ($\mu$M) | S.I.[d] |
|---|---|---|---|---|---|---|
| 3a | H | Me | 18.8 | 4.5 | >100 | >22 |
| 3b | H | Et | 9.7 | 0.8 | >100 | >125 |
| 3c | H | i-Pr | 6.1 | <0.001 | >100 | >100,000 |
| 3d | Me | i-Pr | 4.8 | n.d | n.d. | n.d. |
| AZT | | | >100 | 0.04 | 50 | 1250 |
| MKC-442 | | | | 0.004 | >100 | >25,000 |

[d]Selectivity Index is equal to the ratio of fifty percent cytotoxic concentration to $IC_{50}$.
n.d. = not determined

Example 4

Synthesis of PETT Derivatives

Chemical Synthesis

All chemicals were used as received from Aldrich Chemical Company (Milwaukee, Wis.). All reactions were carried out under nitrogen. Column chromatography was performed using EM Science silica gel 60 and one of the following solvents: ethyl acetate, methanol, chloroform, hexane, or methylene chloride. Nuclear magnetic resonance (NMR) spectra were recorded on a Varian (Palo Alto, Calif.) 300 MHz instrument (Mercury 2000 model) and chemical shifts (δ) are reported in parts per million (ppm) relative to tetramethylsilane as an internal standard at 0 ppm. $^{13}$C NMR spectra were recorded at 75 MHz in $CDCl_3$ on the same instrument using a proton decoupling technique. The chemical shifts reported for $^{13}$C NMR are referenced to the chloroform triplet at 77 ppm. Melting points were measured using a Mel-Temp 3.0 (Laboratory Devices Inc., Holliston, Mass.) melting apparatus and are uncorrected. UV spectra were recorded from a Beckmann (Fullerton, Calif.) model DU 7400 UV/Vis spectrometer using a cell path length of 1 cm and methanol solvent. Fourier Transform Infrared spectra were recorded using an FT-Nicolet (Madison, Wis.) model Protege 460 instrument. Mass spectrum analysis was performed using a Hewlett-Packard (Palo Alto, Calif.) Matrix Assisted Laser Desorption time-of-flight (MALDI-TOF) spectrometer (model G2025A) in the molecular ion detection mode (matrix used was cyanohydroxycinnamic acid). Some samples were analyzed using a Finnigan (Madison, Wis.) MAT 95 instrument. Elemental analysis was performed by Atlantic Microlabs (Norcross, Ga.).

General Procedure for Synthesis of PETT Derivatives

Compounds I-1, I-3, and I-4 were synthesized as described in Scheme 3. Trovirdine (I-2) was synthesized according to the literature procedure (Bell, F. W., et al., *J. Med. Chem.*, 1995, 38,4929–4936).

Scheme 3

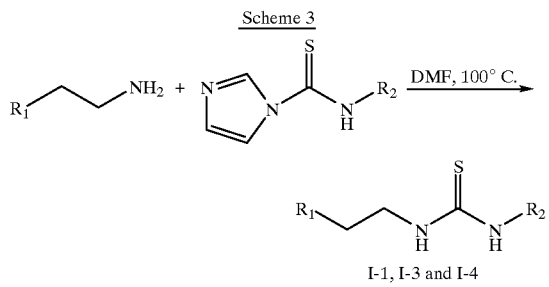

I-1, I-3 and I-4

Physical Data Of Synthesized Compounds:
N-[2-(2-pyridylethyl)]-N'-[2-(pyridyl)]-thiourea (I-1)

white solid (Ig, 49%); mp 98–100° C.; UV(MeOH)λmax: 293, 265, 247 and 209 nm; IR(KBr Disc)ν 3415, 3222, 3050, 2360, 1600, 1533, 1479, 1436, 1315, 1240, 1151 and 775 cm$^{-1}$; $^1$H NMR (CDCl$_3$)δ 11.90 (s, 1H), 8.8 (s, 1H), 8.60–8.58 (d, 1H), 8.03–8.01 (d, 1H), 7.65–7.56 (m, 2H), 7.27–7.14 (m, 2H), 6.93–6.89 (d, 1H), 6.80–6.77 (d, 1H) 4.23–4.15 (q, 2H) and 3.41–3.20 (t, 2H); $^{13}$C NMR(CDCl$_3$)δ 179.2, 158.9, 153.0, 149.2, 145.5, 138.5, 136.4, 123.5, 121.4, 117.7, 111.8, 44.9, and 36.9; MALDI-TOF mass found, 257.1(M-1), calculated, 258.3; Anal. (C$_{13}$H$_{14}$N$_4$S) C, H, N, S.

N-[2-(1-piperidinoethyl)]-N'-[2-(5-bromopyridyl)]-thiourea (I-3)

white solid (2 g, 74%); mp 150–152° C.; UV (MeOH) λmax: 306, 275 and 205 nm; IR(KBr Disc)ν 3155, 3077, 2935, 2850, 2360, 1591, 1525, 1465, 1319, 1226, 1095, 827 and 756 cm$^{-1}$; $^1$H NMR (CDCl$_3$)δ 11.53 (br s, 1H), 9.72 (br s, 1H), 8.22 (d, 1H), 7.72–7.68 (dd, 1H), 6.95–6.92 (d, 1H), 3.84–3.78 (q, 2H), 2.61–2.57 (t, 2H), 2.45 (br s, 4H), 1.64–1.48 (m, 6H); $^{13}$C NMR(CDCl$_3$)δ 178.1, 151.8, 146.3, 140.8, 113.5, 112.6, 56.1, 54.0, 43.0, 26.3, and 24.3, MALDI-TOF mass found, 343.5, calculated, 343.3; Anal. (C$_{13}$H$_{19}$BrN$_4$S) C, H, N, S, Br.

N-[2-(2,5-dimethoxyphenylethyl)]-N'-[2-(5-bromopyridyl)]-thiourea (I-4)

white solid (2 g, 67%); mp 133–138° C.; UV (MeOH) λmax: 202, 205, 231, 276 and 300 nm; IR(KBr Disc)ν 3209, 3152, 3078, 3028, 2951, 2831, 1595, 1533, 1468, 1306, 1227, 1095, 1059, 1022, 862, 825, 796, 707 cm$^{-1}$; $^1$H NMR(CDCl$_3$)δ 11.24 (br s, 1H), 9.30 (br s, 1H), 8.10–8.09 (d, 1H), 7.65 (dd, 1H), 6.82–6.76 (m, 4H), 4.03–3.97 (q, 2H), 3.77 (s, 3H), 3.76 (s, 3H), 3.00–2.96 (t, 2H); $^{13}$C NMR(CDCl$_3$)δ 178.7,153.1,151.8, 151.7,146.5,140.9, 128.1,117.7,113.3, 112.6, 111.2, 110.9, 55.7, 55.5, 45.6, and 29.9; MALDI-TOF mass found, 394.0 (M-1), 396.0 (M+1), calculated, 395.0; Anal. (C$_{16}$H$_{18}$BrN$_3$O$_2$S) C, H, N, S, Br.

Chemical Synthesis II

Compounds II-1–9 were synthesized according to Scheme 4. In brief, 2-amino-5-bromopyridine was condensed with 1,1-thiocarbonyl diimidazole to furnish the precursor thiocarbonyl derivative (A). Further reaction with appropriately substituted phenylethyl amine gave the target PETT derivatives in good yields.

General procedure for synthesis

Thiocarbonyldiimidazole (8.90 g, 50 mmol) and 2-amino-5-bromo pyridine (8.92 g, 50 mmol) were added to 50 mL of dry acetonitrile at room temperature. The reaction mixture was stirred for 12 h and the precipitate filtered, washed with cold acetonitrile (2×25 mL), and dried under vacuum to afford (11.40 g, 80% ) of compound A. To a suspension of compound A (0.55 eqv) in dimethyl formamide (15 mL) an appropriate amine (0.50 eqv) was added. The reaction mixture was heated to 100° C. and stirred for 15 hours. The reaction mixture was poured into ice-cold water and the suspension was stirred for 30 minutes. The product was filtered, washed with water, dried, and further purified by column chromatography to furnish the target compounds I-9 in good yields.

Scheme 4

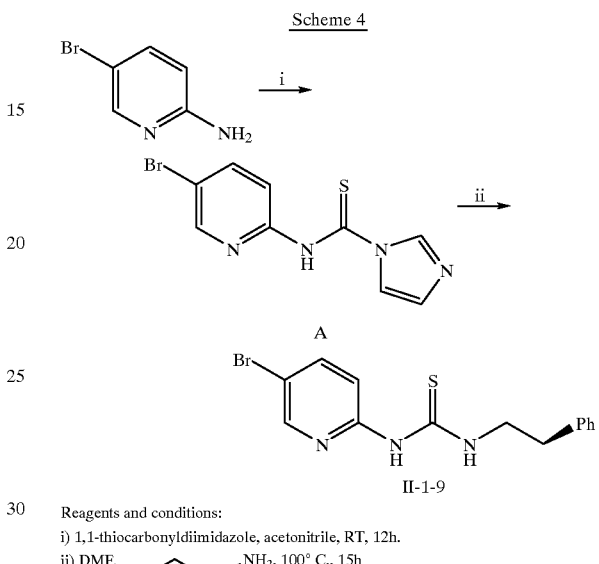

Reagents and conditions:
i) 1,1-thiocarbonyldiimidazole, acetonitrile, RT, 12h.
ii) DMF, Ph⌒⌒NH$_2$, 100° C., 15h Physical data of synthesized compounds:
N-12-(2-methoxyphenethyl)]-N'-[2-(5-bromopyridyl)]-thiourea (II-1)

yield: 65%; mp 143–145° C.; UV (MeOH)λmax: 202, 205, 275 and 306 nm; IR(KBr)ν 3211, 3153, 3036, 2956, 2835, 1593, 1533, 1462, 1242, 1186, 1036, 1007, 862, 812, 756, 708 cm$^{-1}$; $^1$H NMR (CDCl$_3$)δ 11.22 (br s, 1H), 9.37 (br s, 1H), 8.02–8.01 (d, 1H), 7.69–7.65 (dd, 1H), 7.28–7.18 (m, 2H), 6.94–6.80 (m, 3H), 4.04–3.98 (q, 2H), 3.81 (s, 3H), 3.04–2.99 (t, 2H); $^{13}$C NMR(CDCl$_3$)δ 178.7, 157.6, 151.7, 146.3, 141.0, 130.7, 127.9, 126.8, 120.3, 113.5, 112.5, 110.3, 55.2, 45.6, 29.8; Maldi Tof found: 366.0 (M+1), calculated: 365.0; Anal. (C$_{15}$H$_{16}$BrN$_3$OS) C,H,N,S.

N-[2-(2-fluorophenethyl)]-N'-[2-(5-bromopyridyl)]-thiourea (II-2)

yield: 71%; mp 156–157° C.; UV (MeOH)λmax: 209, 256, 274 and 305 nm; IR(KBr)ν 3446, 3234, 3163, 3055, 2935, 1672, 1595, 1560, 1531, 1466, 1390, 1362, 1311, 1265,1227,1169,1136,1089,1003, 864,825, 756 cm$^{-1}$; $^1$H NMR (CDCl$_3$)δ 11.36 (br s, 1H), 9.47 (br s, 1H), 8.05–8.04 (d, 1H), 7.72–7.68(dd, 1H), 7.30–7.03 (m, 4H), 6.87–6.84 (d, 1H), 4.06–3.99 (q, 2H), 3.10–3.05 (t, 2H); $^{13}$C NMR (CDCl$_3$)δ 179.1, 163.1, 151.7, 146.2, 141.1, 131.2, 131.1, 128.5, 128.4, 124.1, 115.5, 115.2, 113.6, 112.2, 45.8 and 28.2; $^{19}$F NMR(CDCl$_3$) 6–42.58 & -42.55 (d); Maldi Tof found: 355.0 (M+1), calculated: 354.0; Anal. (C$_{14}$H$_{13}$BrFN$_3$S) C, H, N, S.

N-[2-(2-chlorophenethyl)]-N'-[2-(5-bromopyridyl)]-thiourea (II-3)

yield: 72%; mp 137–139° C.; UV (MeOH)λmax: 208, 213, 256, 275 and 305 nm; IR(KBr)ν 3433, 3221, 3157, 3089, 3037, 2922, 2866, 1668, 1597, 1535, 1466, 1338, 1263, 1209, 1188, 1130, 1095, 1053, 1001, 864, 823, 750 cm⁻¹; ¹H NMR (CDCl₃)δ 11.41 (br s, 1H), 9.54 (br s, 1H), 8.17–8.16 (d, 1H), 7.83–7.79 (dd, 1H), 7.50–7.30 (m, 4H), 6.97–6.94 (d, 1H), 4.19–4.13 (q, 2H), 3.30–3.26 (t, 2H); ¹³C NMR(CDCl₃)δ 179.2, 151.7, 146.3, 141.2, 136.3, 134.2, 131.1, 129.6, 128.1, 126.8, 113.6, 112.7, 45.2, and 32.5; Maldi Tof found: 371.8 (M+1), calculated: 371.0; Anal. (C₁₄H₁₃BrClN₃S) C, H, N, S, Br.

N-[2-(3-methoxyphenethyl)]-N'-[2-(5-bromopyridyl)]-thiourea (II-4)

yield: 68%; mp 155–156° C.; UV (MeOH)λmax: 208, 274 and 306 nm; IR(KBr)ν 3454, 3236, 3147,3030,2951, 2869, 2827, 1591, 1545, 1525, 1466, 1304, 1265, 1229, 1188,1151, 1095,1051, 1024, 980, 860, 825, 789, 698 cm⁻¹; ¹H NMR (CDCl₃)δ 11.30 (br s, 1H), 9.25 (br s, 1H), 8.05–8.04 (d, 1H), 7.71–7.67 (dd, 1H), 7.29–7.24 (t, 1H), 6.89–6.78 (m, 4H), 4.05–3.99 (q, 2H), 3.81 (s, 3H), 3.00–2.96 (t, 2H); ¹³C NMR(CDCl₃)δ 178.9, 159.7, 151.6, 146.4, 141.1, 140.3, 129.6, 121.2, 115.0, 113.4, 112.7, 111.6, 55.1, 47.1 and 34.8; Maldi Tof found: 367.0 (M+2), calculated: 365.0; Anal. (C₁₅H₁₆BrN₃OS) C, H, N, S.

N-[2-(3-fluorophenethyl)]-N'-[2-(5-bromopyridyl)]-thiourea (II-5)

yield: 73%; mp 171–172° C.; UV (MeOH)λmax: 202, 208, 258, 275 and 306 nm; IR(KBr)ν 3213, 3155, 3084, 3028, 2866, 1595, 1533, 1477, 1336, 1308, 1229, 1211, 1173, 1136, 1092, 1026, 935, 870, 827, 791, 740 cm⁻¹; ¹H NMR (CDCl₃) δ11.33 (br s, 1H), 9.46 (br s, 1H), 8.05–8.04 (d, 1H), 7.73–7.69 (dd, 1H), 7.31–7.26 (m, 1H), 7.08–6.97 (m, 3H), 6.87–6.83 (d, 1H), 4.06–3.99 (q, 2H), 3.05–3.00 (t, 2H); ¹³C NMR (CDCl₃) δ 179.1, 163.1, 151.7, 146.2, 141.2, 130.1,129.9,124.5, 115.9, 115.6, 113.7, 113.5, 113.4, 112.8, 46.7 and 34.6; ¹⁹F NMR(CDCl₃)δ –37.30&–37.33 (d); Maldi Tof found: 354.0 (M⁺), calculated: 354.0; Anal. (C₁₄H₁₃BrFN₃S) C, H, N, S.

N-[2-(3-chlorophenethyl)]-N'-[2-(5-bromopyridyl)]-thiourea (II-6)

yield: 72%; mp 163–165° C.; UV (MeOH)λmax: 202, 213, 258, 276 and 305 nm; IR(KBr)ν 3242, 3161, 3043, 2929, 1593, 1579, 1547, 1527, 1466, 1313, 1227, 1167, 1095, 997, 889, 827, 812, 785, 700 cm⁻¹; ¹H NMR (CDCl₃)δ 11.33 (br s, 1H), 9.37 (br s, 1H), 8.09–8.08 (d, 1H), 7.73–7.69 (dd, 1H), 7.28–7.15 (m, 4H), 6.85–6.82 (d, 1H), 4.04–3.98 (q, 2H), 3.02–2.97 (t, 2H), ¹³C NMR (CDCl₃)δ 179.1,151.6, 146.3, 141.2, 140.7, 134.2,129.8, 129.0, 127.0, 126.8, 113.4,112.8, 46.7 and 34.5; Maldi Tof found: 371.8 (M+1), calculated: 371.0; Anal. (C₁₄H₁₃BrClN₃S) C, H, N, S.

N-[2-(4-methoxyphenethyl)]-N'-[2-(5-bromopyridyl)]-thiourea (II-7)

yield: 85%; mp 178–179° C.; UV (MeOH)λmax: 205, 226, 275 and 305 nm; IR(KBr)ν 3221, 3159, 3042, 2931, 2827, 1587, 1510, 1464, 1311, 1225, 1165, 1088, 1034, 820, 773, 708 cm⁻¹; ¹H NMR (CDCl₃)δ 11.30 (br s, 1H), 9.87 (br s, 1H), 8.00–7.99 (d, 1H), 7.67–7.63 (dd, 1H), 7.21–7.18 (d, 2H), 6.95–6.85 (m, 3H), 4.00–3.93 (q, 2H), 3.81 (s, 3H), 2.96–2.92 (t, 2H); ¹³C NMR (CDCl₃)δ 179.1, 158.0,151.9, 145.8,140.7,130.6, 129.6,113.8,113.7, 112.1, 55.1,46.9 and 33.8; Maldi Tof found: 366.0 (M+1), calculated: 365.0; Anal. (C₁₅H₁₆BrN₃OS) C, H, N, S.

N-[2-(4-fluorophenethyl)]-N'-[2-(5-bromopyridyl)]-thiourea (II-8)

yield: 69%; mp 177–178° C.; UV (MeOH)λmax: 208, 211, 274 and 306 mn; IR(KBr)ν 3456, 3213, 3155, 3086, 3028, 2868, 1595, 1560, 1533, 1477, 1336, 1308, 1238, 1211, 1173, 1136, 1092, 1026, 933, 869, 827, 791, 741, 694 cm⁻¹; ¹H NMR (CDCl₃)δ 11.29 (br s, 1H), 9.27 (br s, 1H), 8.04–8.03 (d, 1H), 7.73–7.69 (dd, 1H), 7.27–7.22 (m, 2H), 7.04–6.99 (m, 2H), 6.83–6.79 (d, 1H), 4.03–3.96 (q, 2H), 3.02–2.97 (t, 2H); ¹³C NMR(CDCl₃)δ 179.1, 163.2, 151.6, 146.3, 141.2, 134.3, 130.3, 130.2, 115.4, 115.2, 113.5, 112, 47.0, and 34.1; ¹⁹F NMR (CDCl₃) δ –40.55 (m); Maldi Tof found: 354.8 (M+1), calculated: 354.0; Anal. (C₁₄H₁₃BrFN₃S) C, H, N, S.

N-[2-(4-chlorophenethyl)]-N'-[2-(5-bromopyridyl)]-thiourea (II-9)

yield: 71%; mp 180–183° C.; UV (MeOH)λmax: 206, 209, 219, 256, 275 and 305 nm; IR(KBr)ν 3221, 3153, 3086, 3022, 2931, 1674, 1593, 1562, 1533, 1473, 1406, 1340, 1304, 1265, 1227, 1169, 1138, 1092, 1016, 820, 752, 714 cm⁻¹; ¹H NMR (CDCl₃)δ 11.40 (br s, 1H), 9.34 (br s, 1H), 8.15–8.14 (d, 1H), 7.84–7.80 (dd, 1H), 7.46–7.30 (m, 4H), 6.92–6.89 (d, 1H), 4.10–4.07 (q, 2H), 3.13–3.08 (t, 2H); ¹³C NMR (CDCl₃)δ 179.2, 151.6, 146.3, 141.3, 137.1, 130.2, 128.6, 113.5, 112.8, 46.8 and 34.2; Maldi Tof found: 372.0 (M+1), calculated: 371.0; Anal. (C₁₄H₁₃BrClN₃S) C, H, N, S.

Chemical Synthesis m

Compounds III-1–3 were prepared as illustrated in Scheme 5. The synthesis involved condensing 2-amino-5-bromopyridine with 1,-thiocarbonyl diimidazole to furnish the required thiocarbonyl derivative. Further reaction of this thiocarbonyl derivative with an appropirate amine gave 1–3 in good yields.

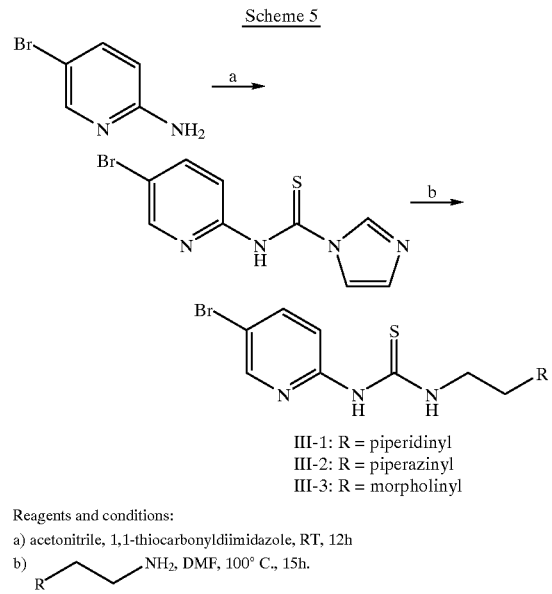

Scheme 5

III-1: R = piperidinyl
III-2: R = piperazinyl
III-3: R = morpholinyl

Reagents and conditions:
a) acetonitrile, 1,1-thiocarbonyldiimidazole, RT, 12h
b) R⌒⌒NH₂, DMF, 100° C., 15h.

Physical data of synthesized compounds:

N-[2-(1-piperidinylethyl)]-N'-[2-(5-bromopyridyl)]-thiourea (III-1)

Yield: 74%; mp 150–152°; ¹H NMR (CDCl₃)δ 11.53 (br s, 1H), 9.72 (br s, 1H), 8.22 (d, 1H), 7.72–7.68 (dd, 1H), 6.95–6.92 (d, 1H), 3.84–3.78 (q, 2H), 2.61–2.57 (t, 2H), 2.45 (br s, 4H), 1.64–1.48 (m, 6H); ¹³C NMR(CDCl₃)δ 178.1, 151.8, 146.3, 140.8, 113.5, 112.6, 56.1, 54.0, 43.0, 26.3, and 24.3.

N-[2-(1-piperizinylethyl)]-N'-[2-(5-bromopyridyl)]-thiourea (III-2)

Yield: 75%; mp 178–180° C.; ¹H NMR (CDCl₃)δ 11.50 (br s, 1H), 9.77 (br s, 1H), 8.19–8.18 (d, 1H), 7.75–7.71 (dd, 1H), 6.97–6.95 (d, 1H), 3.87–3.86 (m, 2H), 3.63–3.60 (t, 2H), 3.45–3.42 (m, 3H), 2.74–2.69 (t, 2H), 2.59–2.52 (m, 4H); ¹³C NMR(CDCl₃)δ 178.7, 151.8, 146.1, 141.0, 113.7, 112.7, 55.2, 52.0, 51.9 and 45.8.

N-[2-(1-morpholinylethyl)]-N'-[2-(5-bromopyridyl)]-thiourea (III-3)

Yield: 65%; 124–126° C.; $^1$H NMR (CDCl$_3$)δ 11.51 (br s, 1H), 9.23 (br s, 1H), 8.25–8.24 (d, 1H), 7.75–7.71 (dd, 1H), 6.85–6.82 (d, 1H), 3.87–3.74 (m, 6H), 2.68–2.54 (m, 6H); $^{13}$C NMR(CDCl$_3$)δ 178.5, 151.7, 146.4, 141.0, 113.5, 112.7, 67.2, 55.4, 53.1, 42.5.

| Compound | R | Compound | R |
|---|---|---|---|
| I-1 | pyridyl | II-1 | piperidinyl |
| I-3 | piperidinyl | III-2 | piperozinyl |
| I-4 | 2,5-dimethoxy phenyl | III-3 | morpholinyl |
| II-1 | o-methoxy phenyl | II-6 | m-chlorophenyl |
| II-2 | o-fluorophenyl | II-7 | p-methoxy phenyl |
| II-3 | o-chlorophenyl | II-8 | p-flurophenyl |
| II-4 | m-methoxy phenyl | II-9 | p-chlorophenyl |
| II-5 | m-fluorophenyl | | |

Example 5

Structure-based Design and Docking of Novel PETT Derivatives into Composite NNI Binding Pocket I A novel model of the NNI binding pocket of RT was constructed by carefully superimposing the coordinates of 9 individual RT-NNI crystal structures and then generating a van der Waals surface which encompassed all of the overlaid ligands. The integrated structural information of this "composite binding pocket" revealed an unexpectedly different and much larger NNI binding site than shown in or predictable from any of the individual structures and served as a probe to more accurately define the potentially usable space in the binding site (FIG. 2a). A number of protein residues in contact with the inhibitors are relatively flexible and vary from structure to structure. These residues include Tyr180, Tyr181, Tyr318, Try319, Phe227, Leu234, Trp229, Pro95, and Glu138 (from p51 subunit of RT). As shown in FIG. 2b, the surface of the composite binding pocket is a short distance away from (<1.5 Å) or even extends past RT residues 234–236, Y188, F227, and the backbone of K101. This indicates that these residues are flexible and can be displaced by the right inhibitor. The composite binding pocket, unlike an individual crystal structure, is able to summarize the nature and extent of the flexibility of the active site residues. This allowed prediction of potential modification sites on the PETT derivatives I after positioning the compounds in the RT active site (see Methods).

A computer simulation of the binding of PETT compounds into the NNI binding site of RT was accomplished using a molecular docking procedure. Docking of PETT and trovirdine into the NNI binding site required the use of X-ray coordinates of an RT/NNI complex (in this case the RT/9-Cl-TIBO complex).

Upon binding to RT, the compound can fit into a butterfly-shaped NNI binding site (described by Ding, J., et al., Nat. Struct. Biol., 1995, 2, 407–415) (FIGS. 1B and 2). PETT and its derivatives such as compounds I-1–4 could be viewed as two chemical groups linked together by a thiourea group (Table 5). One half of the molecule is composed of a 2-aminothiazole group (PETT) or a pyridylthiourea group (compounds I-1–4) which forms an intramolecular hydrogen-bonded heterocyclic ring. The other half of the molecule is a phenyl or heterocyclic ring separated from the thiocarbonyl group by an ethyl linker.

Once the final docked position of the molecule in the NNI site was determined, the molecule was assigned a score, from which an estimation of the inhibition constant ($K_i$ value) was determined (Table 5). When trovirdine was docked into the NNI binding site of RT it had a higher binding score than PETT and fit into the butterfly-shaped binding region with one part residing in Wing 1 and the other in Wing 2 (FIG. 1B). The ring closest to the thiocarbonyl group resided near the Lys(K)101 loop and the other pyridyl ring was near Trp(W)229.

After docking and $K_i$ estimation was completed for the PETT inhibitors, evaluation of the docked compounds in the active site of RT involved placing each compound into the composite binding pocket using the same orientation matrix utilized in its construction. The potentially flexible regions in the binding site were then readily identified as were atom sites for future derivatization of the compounds. The area within Wing 2 and the residues near the thiourea group seemed to be the most forgiving regions in the binding site of RT. This observation was also supported by the analysis of gaps in atom-to-atom contact between the protein and the inhibitor.

TABLE 5

Interaction scores, calculated $K_i$ values, and measured IC$_{50}$ data for PETT derivatives I.

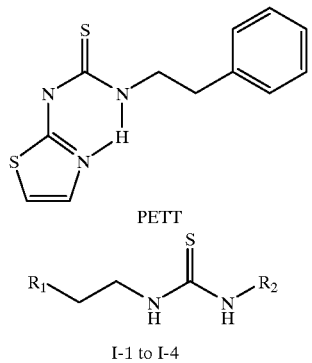

|  | R₁ | R₂ | M.S.ᵃ (Å²) | B.S.ᵇ (%) | Lipo Score | Ludiᶜ Score | Ludiᶜ K$_i$ (μM) | IC₅₀ p24 (μM) | S.I.ᵈ |
|---|---|---|---|---|---|---|---|---|---|
| PETT | phenyl | 2-thiazolyl | 254 | 84 | 625 | 562 | 2.4 | n.d. | n.d. |
| I-1 | 2-pyridyl | 2-pyridyl | 260 | 84 | 640 | 577 | 1.7 | 0.230 | >435 |
| I-2 Trovirdine | 2-pyridyl | 2-(5-bromo)pyridyl | 276 | 84 | 679 | 616 | 0.7 | 0.007 | |
| I-3 | 1-piperidinyl | 2-(5-bromo)pyridyl | 278 | 84 | 684 | 621 | 0.6 | <0.001 | >10⁴ |
| I-4 | 2,5-dimethoxyphenyl | 2-(5-bromo)pyridyl | 317 | 84 | 779 | 716 | 0.2 | <0.001 | >10⁵ |
| AZT | | | | | | | | 0.008 | 6250 |

ᵃMS, molecular surface area calculated using Connolly's MS program. (Connolly, M. L., Science, 1983, 221, 709–713) Defined as boundary of volume within any probe sphere (meant to represent a water molecule) of given radius sharing no volume with hard sphere atoms which make up the molecule. Values are slightly smaller than those approximated by Ludi program.
ᵇBS, buried surface: percentage of molecular surface in contact with protein calculated by Ludi based on docked positions. Based on published crystal structures of RT complexes, our calculation shows that these values could be as low as 77% (in RT-HEPT complex) and can be as high as 90% (in RT-APA complex) but most of them including RT-MKC average around 84%.
ᶜLudi Ki values were calculated based on the empirical score function in Ludi program. (Bohm, H. J., J. Comput. Aided. Mol. Des., 1994, 8, 243–256; 1996,) Ideal hydrogen bond distances and angles between compounds and protein are assumed in all cases for Ludi K$_i$ and Ludi Score calculation. In published crystal structures of RT complexes, hydrogen bond geometries are indeed close to ideal; the amide carbonyl of residue A101 on a loop demonstrates substantialflexibility which can accommodate the best geometry for hydrogen bonding. The number of rotatable bonds (= 2) is used in the Ludi calculation to reflect the loss of binding energy due to freezing of internal degrees of freedom.
ᵈSelectivity Index is equal to the ratio of fifty percent cytotoxic concentration to IC₅₀.
n.d., not determined.

Figure 3B:
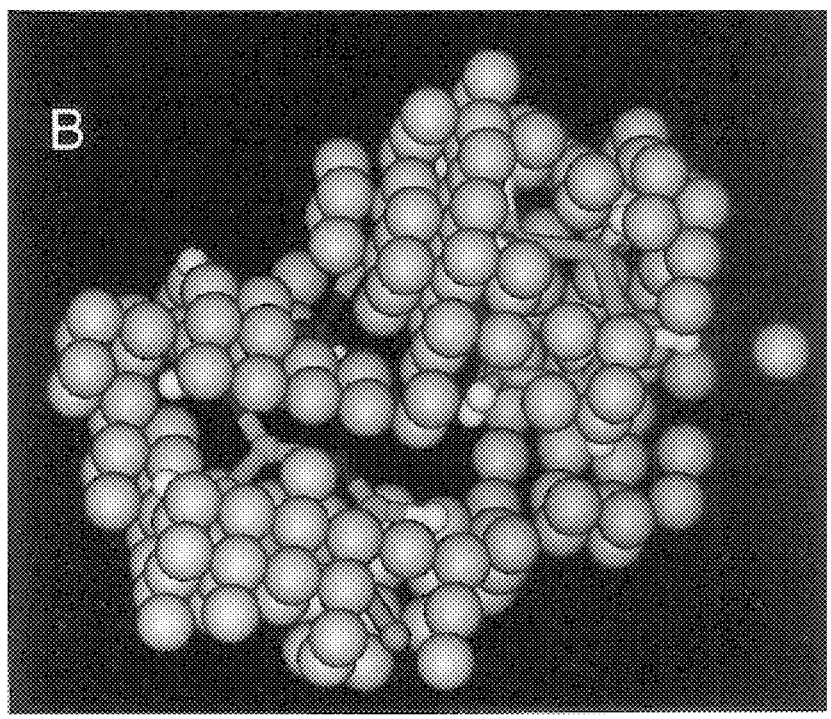
FIG. 3B shows a model of PETT compound I-3 docked in the NNI binding site and color-coded by atom type. Spheres represent the sites of the molecular surface which are in contact with protein residues and are unavailable for future modification.

Analysis of the molecular surface of the compounds in the NNI binding site of RT included visualization of spatial gaps between the compounds and nearby residues of the RT protein, as described above for Example 1. The spheres generated are shown in FIG. 3, and indicate regions of the compound which are probably not available for derivatization. FIG. 4 shows the binding pocket embellished with a grid of red rods which represent unoccupied space between the compound and active site residues, providing a complementary view to that shown by the spheres in FIG. 3. The grid illustrates the candidate sites for derivatization of the compound and, when used as a distance scale (the length of one rod represents 1 Å), also indicates the volume available for new functional groups. After the docked PETT compounds were subjected to the grid (gap) analysis, a number of gaps in the binding site were identified (FIGS. 3–4), some of which could be filled by strategically designed functional groups on new PETT derivatives. It was postulated that a more efficient use of such sterically allowed unoccupied spatial gaps in the binding site could be achieved by replacing the 2-pyridyl ring of trovirdine with a 1-piperidinyl (compound I-3) or 2,5-dimethoxyphenyl moiety (compound I-4) and yield potentially more active PETT compounds with larger molecular surface areas, higher Ludi scores, and lower Ki values (Table 5).

Compounds I-1, I-3 and I-4 were subjected to the same docking procedure and K$_i$ calculation used to analyze the parent compounds PETT and trovirdine (compound I-2). The molecular surface area of the compounds calculated after docking increased in the following order: PETT, compound I-1, I-2 (trovirdine), I-3, and I-4. At docked positions, the atom surface area in contact with the protein residues constituted an average of 84% of the entire molecular surface (FIG. 3). We used this average value in the calculation of the inhibitory constant (K$_i$) based on the Ludi score function. Calculated Ki values for I-3 and I-4 predicted that these compounds would have potency superior to that of trovirdine. The calculated K$_i$ values of our compound I-3 (0.6 μM), and compound I-4 (0.2 μM) were better than those of known compounds PETT (2.4 μM), compound I-1 (1.7 μM) and trovirdine (0.7 μM).

Example 6

In Vitro Assays of Anti-HIV Activity Using PETT Derivatives I

The HIV-1 strain HTLV$_{IIIB}$ (kindly provided by Dr. Neal T. Wetherall, VIROMED Laboratories, Inc.), was propagated in CCRF-CEM cells, and used in in vitro assays of the anti-HIV-1 activity of the synthesized novel derivatives. Cell-free supernatants of HTLV$_{IIIB}$-infected CCRF-CEM cells were harvested, dispensed into 1 ml aliquots, and frozen at −70° C. Periodic titration of stock virus was performed by examining its cytopathic effects in MT-2 cells following the procedures described in (Erice, et al., *Antimicrob. Ag. Chemother.*, 1993, 37, 835).

Normal human peripheral blood mononuclear cells (PBMNC) from HIV-negative donors were cultured 72 hours in RPMI 1640 supplemented with 20%(v/v) heat-inactivated fetal bovine serum (FBS), 3% interleukin-2, 2 mM L-glutamine, 25 mM HEPES, 2 g/L NaHCO₃, 50 μg/ml gentamicin, and 4 μg/ml phytohemagglutinin prior to exposure to HIV-l. The incubated cells were then exposed to HIV-1 at a multiplicity of infection (MOI) of 0.1 during a one-hour adsorption period at 37° C. in a humidified 5% CO₂ atmosphere. Subsequently, infected cells were cultured in 96-well microtiter plates (100 μl/well; 2×10⁶ cells/ml) in the presence of test compounds, including AZT as a control. Aliquots of culture supernatants were removed from the wells on the 7th day after infection for p24 antigen assays. The methods used in the P24 assay were as previously described in Uckun, et al., *Antimicrobial Agents and*

Chemotherapy, 1998, 42, 383; Zarling, et al., Nature, 1990, 347, 92–95; Erice, et al., Antimicrob. Ag. Chemother., 1993, 37, 835.

The applied p24 enzyme immunoassay (EIA) was the unmodified kinetic assay commercially available from Coulter Corporation/Immunotech, Inc. (Westbrooke, Me.). In the assay, a murine monoclonal antibody against HIV core protein is coated onto microwell strips. Antigen (HIV core protein) present in the test culture supernatant samples binds the antibody and the bound antibody-antigen complex is quantitated. Percent viral inhibition was calculated by comparing the p24 values from the test substance-treated infected cells with p24 values from untreated infected cells (i.e., virus controls).

In addition, the activity of the test compounds to inhibit recombinant HIV-1 reverse transcriptase (rRT) activity was determined using the Quan-T-RT assay system (Amersham, Arlington Heights, Ill.), which utilizes the scintillation proximity assay principle. The assay method is described in Bosworth, N., et al., Nature, 1989, 341, 167–168. Data for both bioassays is reported as $IC_{50}$ values.

In parallel with the bioactivity assays, the effects of the test compounds on cell viability was also examined, using the Microculture Tetrazolium Assay (MTA) described in Darling, et al., Nature, 1990, 347, 92–95; Erice, et al., Antimicrob. Ag. Chemother., 1993, 37, 835. In brief, non-infected PBMNC were treated with test compounds or controls for 7 days under identical experimental conditions and 2,3-bis(2-methoxy-4-nitro-5-sulfophenyl)-5-[(phenylamino)carbonyl]-2H-tetrazolium hydroxide (XTT), was added to quantitative cellular proliferation.

An energy-minimized model of compound I-4 in the RT binding site had the largest molecular surface area in contact with the protein and thus achieved the highest lipophilicity score. The docking studies indicated that the 2-methoxy group of compound I-4 is situated beneath the ethyl linker and fits favorably into a cavity of the binding pocket, providing contact with protein residues that cannot be achieved by trovirdine. Likewise, the 5-methoxy group of compound I-4 provides close contact with residues Pro95 and Trp229. The trend of the calculated $K_i$ values accurately predicted the trend of the experimentally determined $IC_{50}$ values from HIV replication assays, as shown in Table 5, thereby providing conclusive evidence of the practical utility of the composite model.

The lead compound, I-4 with the lowest calculated $K_i$ values of the series, was 8-times more potent than trovirdine against purified recombinant HIV-RT using the cell-free Quan-T-RT system (IC50[rRT] was 0.1 $\mu$M for I-4 versus 0.8 $\mu$M for trovirdine). Compound I-4 also elicited potent anti-HIV activity with $IC_{50}$ values of less than 0.001 $\mu$M in 3 of 3 independent experiments which was consistently lower than the $IC_{50}$ values for trovirdine (0.007 $\mu$M) and AZT (0.008 $\mu$M). None of the PETT derivatives were cytotoxic at concentrations as high as 100 $\mu$M. Therefore, the calculated selectivity index ($IC_{50}$[MTA]/$IC_{50}$[p24]) of compounds I-3 and I-4 were greater than $10^5$.

All active PETT compounds listed in Table 5 are able to form an intramolecular hydrogen bond between the nitrogen atom of pyridine or thiazole and an amide hydrogen of the thiourea group, as shown in Wing 1 of FIG. 1B. The intramolecular hydrogen bond was also observed in our small molecule crystal structure of compound I-3 (data not shown). The energy gained by the formation of such a hydrogen bond has been estimated to be about 5 kcal/mol (Bell, et al., J. Med Chem., 1995, 38, 4929–4936). Our docking results showed that the internal hydrogen bond keeps the pyridyl thiourea (or thiazolylthiourea) in a more rigid conformation and allows the molecule to adopt the appropriate geometry to occupy Wing 1 of the binding site, and at the same time maintain a hydrogen bond with a backbone carbonyl of residue Lys101 (FIG. 1B).

Figure 5B:
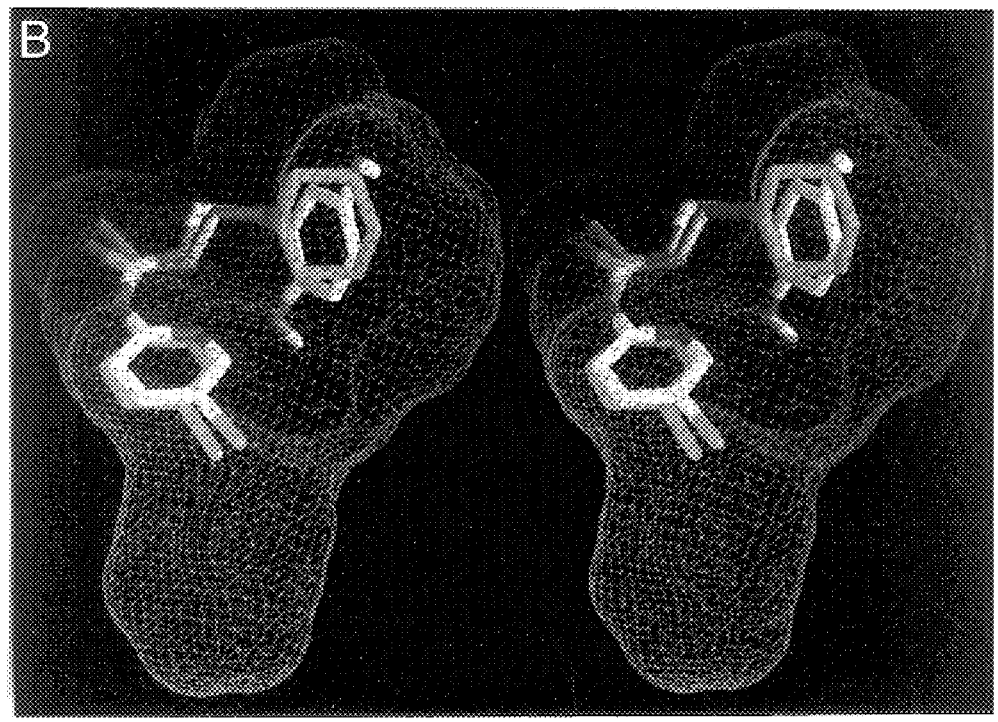
FIG. 5B shows a stereoview of PETT compounds I-3 (in magenta) and I-4 (multicolor) in the composite binding pocket which was constructed from combined coordinates of RT complexed with nine different NNI compounds.

Compounds I-3 and I-4 differ from trovirdine at the proposed Wing 2 binding region of the molecule. Compound I-3 has a heterocyclic ring which replaces the pyridyl ring and compound 4 has two methoxy groups added at meta and ortho positions of the phenyl ring. The molecular surface areas of compounds I-3 and I-4 are larger than that of trovirdine, as calculated from the coordinates of the predicted active conformation obtained from docking. This larger surface area results in a better lipophilic score and lower calculated $K_i$ value (Table 5). Both pyridylethyl and piperidinylethyl groups occupy the same region of Wing 2 near Tyr229 (FIG. 2 and 5). Our composite binding pocket shows a space large enough to accommodate a group larger than the pyridyl ring of trovirdine. Docking results and analyses of gaps indicate that the pyridyl ring of trovirdine has multiple sites which can be used for incorporation of larger groups. As shown in FIG. 5, there is sufficient space surrounding the pyridylethyl ring for the addition of a two- to four-atom substituent at any of the ring positions. Both sides of the pyridylethyl ring plane of trovirdine are relatively exposed in the pocket (FIG. 3A) and can accommodate additional substituents (FIG. 4A). This prediction was confirmed by the potency of compound I-4 (which contains ortho, meta-dimethoxy substituents), in inhibitng HIV replication.

The piperidinyl group of I-3 is puckered and therefore occupies a larger overall volume than the planar pyridyl ring of trovirdine and is in close contact with residues Leu234 and Leu100, the latter of which can mutate to isoleucine, frequently found in a drug-resistant RT mutant strain. In contrast to previously reported extensive attempts at expanding within the pyridyl ring plane (Bell, et al., J. Med. Chem., 1995, 38, 4929–4936; Cantrell, A. S., et al., J. Med Chem., 1996, 39, 4261–4274; Ahgren, C., et al., Antimicrob. Agents Chemotherapy, 1995, 39, 1329–1335), the success of our efforts at modification perpendicular to the ring plane introduces new possibilities to develop more potent inhibitors which combine both modifications. The piperidinyl ring is conformationally more flexible than an aromatic ring has the advantage of fitting an uncompromising binding pocket more effectively, despite the expense paid for loss of entropy upon binding. The analysis shown in FIGS. 3, 4, and 5 provides new insights for modifications which are different from those of trovirdine derivatives. Various combinations of double substitutions at axial or equatorial positions of the piperidinyl ring generate derivatives with a broader range of curvatures than trovirdine derivatives and better fit Wing 2 which itself contains some curvature.

In summary, a composite binding pocket was constructed which integrated all available crystal structure information about the NNI binding site of RT. This novel computer-generated model was an unexpectedly effective tool that helped to much better comprehend the flexible nature of the binding pocket and to identify specific areas for structural improvements of the inhibitors. Nine lead NNI compounds from published crystal structures were analyzed. With all strategies combined, a number of previously unknown candidate sites for developing more potent derivatives of PETT were identified, such as substituting a bulkier piperidinyl group or an ortho/meta substituted phenyl group in place of an unsubstituted ring which resulted in enhanced inhibitory activity. The presented experimental results demonstrate that two novel PETT derivatives which resulted from our structure-based design efforts using the composite binding pocket are remarkably potent and noncytotoxic anti-HIV agents with unprecedented selectivity indices of >$10^5$. The superior activity of these designed PETT compounds would not have been predictable from existing information about trovirdine alone, or from any single crystal structure of RT complexed with an NNI.

Example 7

Structure-based Design and Docking of PETT Derivatives into Composite NNI Binding Pocket II The PETT derivatives II, synthesized as described above for Example 4, were analyzed for fit into the NNI binding pocket. Target compounds were also analyzed for anti-viral activity in p24 enzyme immunoassays and also for the ability to inhibit HIV reverse transcriptase activity, using rRT. Methods for these biological assays are described above for Example 6.

PETT

Trovirdine $R_{2,3,5}$ = 2 or 3-atom (non-H) group
$R_4$ = hydrophobic group
$R_{6,7}$ = 3 or 4-atom (non-H) group
$R_8$ = large alkyl group (such as phenyl)
X = undefined atom Potential Modification Sites for PETT Derivatives A computer simulation of the binding of the target PETT derivatives into the NNI binding site of RT was accomplished using a molecular docking procedure. Docking of the compounds into the NNI binding site required the use of X-ray coordinates of an RT/NNI complex (in this case the RT/9-Cl-TIBO complex).

Trovirdine derivatives could be viewed as two chemical groups linked together by a thiourea group (Table 6). One half of the molecule is composed of a pyridylthiourea group (compounds II-1–9) which forms an intramolecular hydrogen-bonded heterocyclic ring (shown in trovirdine structure). The other half of the molecule is a pyridyl ring separated from the thiocarbonyl group by an ethyl linker.

When trovirdine was docked into the NNI binding site of RT, it fit into the butterfly-shaped binding region (described by Ding, et al., *Nat. Struct. Biol.,* 1995, 2, 407–415) with one part of the molecule residing in Wing 1 and the other in Wing 2. The ring closest to the thiocarbonyl group resided near the Lys(K)101 loop and the other pyridyl ring was near Trp(W)229.

Figure 6:
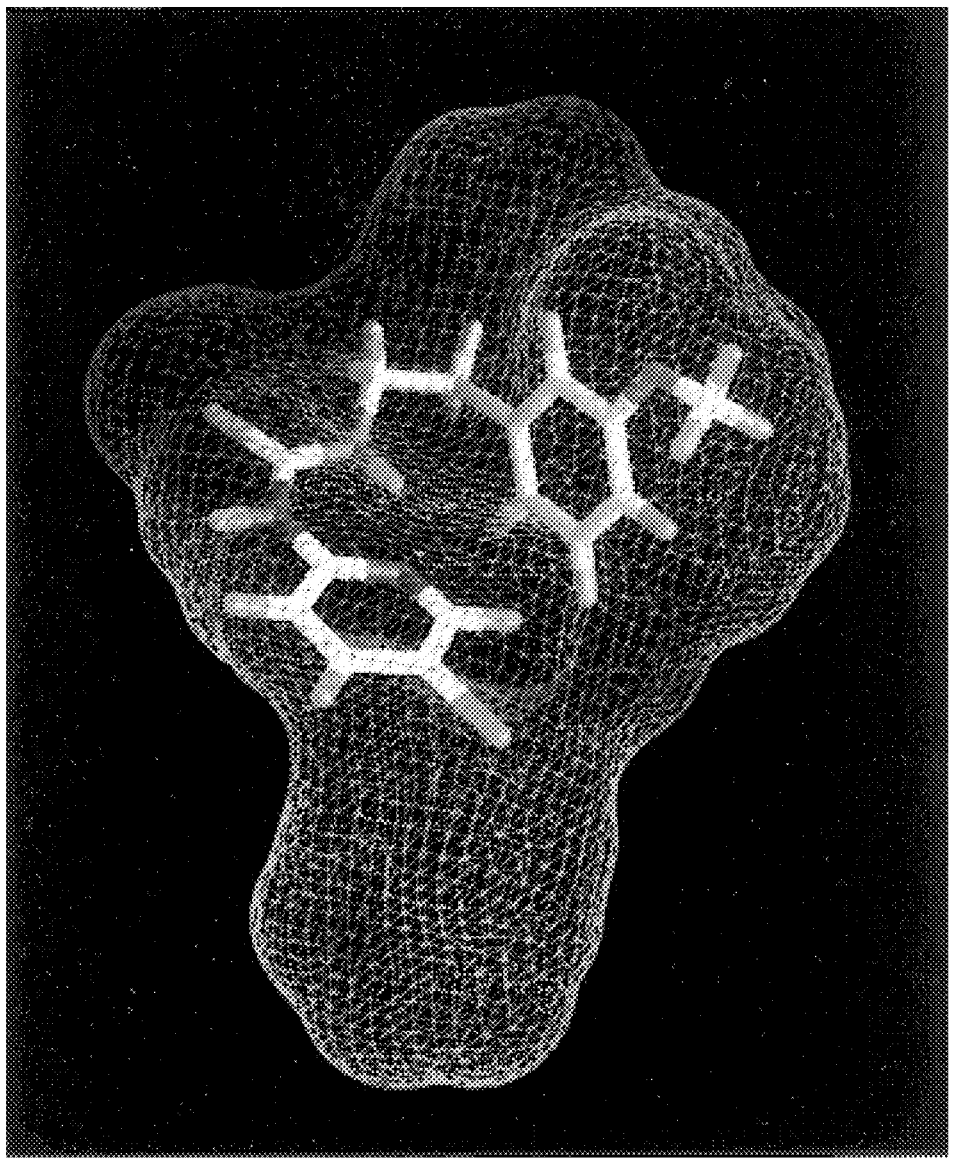
FIG. 6 shows a model of PETT compound I-4 docked in the NNI binding site and color-coded by atom type, as described above for FIG. 3A. The surface of the composite binding pocket is color-coded for hydrogen bonding (red), hydrophobic (gray) and hydrophilic (blue) groups of the superimposed inhibitors.

Compounds II-1–9 were positioned according to this binding mode into the RT/9-Cl-TIBO active site by a docking procedure described above for Example 1. The results are shown in FIG. 6. One of the NH groups of the thiourea part of these compounds consistently formed a hydrogen bond with the backbone of K101.

Once the final, energetically favored docked position of the molecule in the NNI site was determined, a LUDI score was assigned, from which an estimation of the inhibition constant ($K_i$ value) was determined (Table 6). The calculated $K_i$ values, ranging from 0.4 µM to 0.8 µM suggested that compounds II-2–7 would be active inhibitors of RT. The modeling data, shown below in Table 6, predicted that compounds II-2 to II-7 would be as potent as or more potent than trovirdine for inhibiting RT. The data for the bioassay of RT inhibition follows this prediction.

TABLE 6

Interaction scores, $K_i$ values, and measured $IC_{50}$ data for a series of PETT derivatives.

II-1 to II-9

| Compound | X | $MS^a$ (Å$^2$) | $BS^b$ (%) | LIPO Score | $K_i$ (calc) (µM)$^c$ | $IC_{50}$ rRT* (µM) | $IC_{50}$ p24 (µM) | $SI^d$ |
|---|---|---|---|---|---|---|---|---|
| II-1 | o-OMe | 282 | 82% | 678 | 1.2 | 1.0 | 0.01 | >1 × $10^4$ |
| II-2 | o-F | 281 | 82% | 674 | 0.8 | 0.6 | <0.001 | >1 × $10^5$ |
| II-3 | o-Cl | 285 | 83% | 694 | 0.5 | 0.7 | <0.001 | >1 × $10^5$ |
| II-4 | m-OMe | 296 | 84% | 729 | 0.4 | 0.4 | 0.003 | >3 × $10^4$ |
| II-5 | m-F | 282 | 83% | 687 | 0.6 | 0.7 | <0.001 | >1 × $10^5$ |
| II-6 | m-Cl | 283 | 81% | 672 | 0.8 | 3.1 | N.D. | N.D. |
| II-7 | p-OMe | 302 | 83% | 734 | 0.6 | 0.9 | 0.015 | >6 × $10^3$ |
| II-8 | p-F | 284 | 81% | 674 | 7.8 | 6.4 | N.D. | N.D. |
| II-9 | p-Cl | 293 | 81% | 696 | 4.7 | 2.5 | N.D. | N.D. |
| trovirdine | N.A. | 276 | 84% | 679 | 0.7 | 0.8 | 0.007 | >1 × $10^4$ |
| AZT | N.A. | N.A. | N.A. | N.A. | N.A. | >100 | 0.004 | 7 × $10^3$ |

TABLE 6-continued

Interaction scores, $K_i$ values, and measured $IC_{50}$ data for a series of PETT derivatives.

[Chemical structure: PETT derivative with thiourea group, ethyl linker to substituted phenyl ring (X), and 5-bromopyridine moiety. Labeled II-1 to II-9]

| Compound | X | MS[a] (Å[2]) | BS[b] (%) | LIPO Score | $K_i$ (calc) ($\mu$M)[c] | $IC_{50}$ rRT* ($\mu$M) | $IC_{50}$ p24 ($\mu$M) | SI[d] |
|---|---|---|---|---|---|---|---|---|

*rRT, recombinant HIV reverse transcriptase assay
[a]MS, molecular surface area calculated using Connolly's MS program. (Connolly, Science, 1983, 221, 709–713) Defined as boundary of volume within any probe sphere (meant to represent a water molecule) of given radius sharing no volume with hard sphere atoms which make up the molecule. Values are slightly smaller than those approximated by Ludi program.
[b]BS, buried surface: percentage of molecular surface in contact with protein calculated by Ludi based on docked positions. Based on published crystal structures of RT complexes, our calculation shows that these values could be as low as 77% (in RT-HEPT complex) and can be as high as 90% (in RT-APA complex) but most of them average around 84%.
[c]Ludi $K_i$ values were calculated based on modified empirical score function in the Ludi program as described for Example 1. (Bohm, J. Comput. Aided. Mol. Des., 1994, 8, 243–256; 1996,) Ideal hydrogen bond distances and angles between compounds and protein are assumed in all cases for Ludi Score and $K_i$ calculation. In published crystal structures of RT complexes, hydrogen bond geometries are indeed close to ideal; the amide carbonyl of residue A101 on a loop demonstrates substantial flexibility which can accommodate the best geometry for hydrogen bonding. The number of rotatable bonds (2, or 2 + n for n methoxy groups) is used in the Ludi calculation to reflect loss of binding energy due to freezing of internal degrees of freedom.
[d]SI (selectivity index) = $IC_{50}$[MTA]/$IC_{50}$[p24]). $IC_{50}$[MTA] values were >100 $\mu$M for compounds II-1-9, as well as trovirdine. $IC_{50}$[MTA] for AZT was 50 $\mu$M.
N.D., not determined, for compounds with $IC_{50}$[rRT] greater than 1.0 $\mu$M.
N.A., not applicable.

Example 8

In Vitro Assays of PETT Derivatives II

Methoxy Substitutions

The estimated $K_i$ values accurately predicted the trend of the measured $IC_{50}$[rRT] values for the inhibition of recombinant HIV RT. Compound II-4 had the lowest $K_i$ value. The docking results showed that the meta-methoxy group of II-4 is situated near Pro95 and Trp229 in the binding site, providing contact with these protein residues which cannot be achieved by trovirdine (FIG. 5). Based on the $IC_{50}$ [rRT] values of all methoxy compounds, the meta-methoxy substituted compound II-4, which had a $K_i$ value of 0.4 $\mu$M, showed greater inhibitory activity against recombinant HIV RT and it was approximately 2-fold more potent than trovirdine ($IC_{50}$[rRT] was 0.4 $\mu$M for compound II-4 versus 0.8 $\mu$M for trovirdine). Compound II-4 abrogated HIV replication in human peripheral blood mononuclear cells at nanomolar concentrations with an $IC_{50}$ value of 3 nM and a selectivity index (SI) of >$3\times10^4$ (Table 6).

Fluorine Substitutions

Among the fluorine (F) substituted compounds II-2, II-5, and II-8, both meta and ortho fluoro compounds were at least 7-fold more active than trovirdine ($IC_{50}$[p24]<1 nM) (Table 6). Based on the $IC_{50}$[rRT] values, compounds with F substitutions at the meta and ortho positions had nearly the same inhibitory activity against recombinant HIV RT but the para-F substituted compound was 10-fold less active. The color-coded composite binding pocket (FIG. 5) also shows that Wing 2 is mostly hydrophobic except for the region near the ortho positions on both sides of the phenyl ring where polar groups such as halogen atoms would be compatible. Trovirdine, however, lacks such ring substitutents which could provide favorable interactions with these regions of the binding site based on our modeling. Substitutions at the meta position could be on the polar region or the hydrophobic region depending on the chemical group and its consequent conformational change (FIG. 5). The m-F substituent of compound II-5 is probably exposed to the polar (blue) region and therefore is as active as the o-F group which would also be exposed to the polar region according to our modeling. The trend in $IC_{50}$[rRT] values observed for F-substituted compounds may reflect such a preference. The p-F atom, which is small in size but electronegative, may not be compatible with the location of the ring plane of nearby hydrophobic Trp229 and could contribute to the lower activity. We postulate that this same incompatibility should be observed for any other highly hydrophilic group at the para position, and that an additional binding penalty be imposed to better quantitate such features when undertaking modeling studies.

Chlorine Substitutions

Chlorine (Cl) substituted compounds II-3, II-6, and II-9 show a trend of observed biological activities which differs from that of both the fluorine and methoxy compounds. Like the p-F substituted compound which was less active than other F-substituted compounds, the p-Cl compound was less active than the o-Cl compound based on the $IC_{50}$[rRT] values. Unlike the m-F substituted compound which was as active as the o-F substituted compound, the m-Cl compound was not as active as the o-Cl substituted compound. According to our modeling, o-Cl is the most likely substituent to be situated near a limited polar region at Wing 2, an interaction which would be favorable. The o-Cl compound, like the o-F compound discussed above, was in fact more active than trovirdine, as was predicted by the modeling procedure and by the use of the composite binding pocket.

Hydrophobic Group Preferred At The Para Position

When $IC_{50}$[rRT]values of all compounds with para substitutions are compared (II-7–9), a distinct trend is evident: the p-methoxy (OMe) compound (7) is favored over the p-halogen group compounds (II-8 and II-9) (Table 6). Only the p-OMe substituted PETT derivative, compound II-7, is comparable to trovirdine in its inhibitory activity against recombinant HIV RT. Compound II-7 inhibited HIV replication in peripheral blood mononuclear cells with an $IC_{50}$ value of 15 nM (Table 6). This p-OMe preference is consistent with the understanding of the color-coded composite binding pocket at Wing 2, where the binding pocket residues near the para position are relatively hydrophobic. One can reasonably assume, based on chemical intuition and the available inhibition data which is consistent with the modeling, that para substituted hydrophobic groups positioned near a hydrophobic region of the pocket are most preferred, followed by halogens, and finally hydrophilic groups.

Conclusions

In summary, the data revealed the following structure-activity relationships affecting the potency of PETT derivatives with substitutions on various positions of the phenyl ring:

1) methoxy substitution is more favorable at the meta position than at the ortho or para positions;
2) fluorine substitution is favorable at ortho and meta positions but not at the para position;
3) chlorine substitution is favorable only at the ortho position;
4) a hydrophobic group is more desirable than a polar group or hydrophilic group at the para position. These results were generally consistent with predictions made during modeling.

The use of the composite NNI binding pocket allowed the identification and structure-based design of at least 3 promising PETT derivatives with ortho-F (II-2), ortho-Cl (II-3), and meta-F (II-5) substituents on the phenyl ring. These novel PETT derivatives were more active than trovirdine (as predicted) or AZT and showed potent anti-HIV activity with $IC_{50}[p24]$ values <1 nM and selectivity indices (SI) of >100,000 (Table 6).

Example 9

Design of Heterocyclic PETT Derivatives III

In the course of the search for potent NNIs, a computer model has been developed in which a composite binding pocket was constructed from nine individual crystal structures of RT-NNI complexes. Modeling studies lead to the identification of a number of NNIs with $IC_{50}$ values beyond 1 nM for the inhibition of HIV replication (measured by p24 production in HIV-infected human peripheral blood mononuclear cells) and showed no detectable cytotoxicity against human T-lymphocytes (inhibition of cellular proliferation was >100 μM as measured by MTA).

The detailed analysis of trovirdine, a potent PETT derivative, revealed multiple sites which can be used for the incorporation of larger functional groups. In the composite binding pocket, the docked trovirdine molecule showed a lot of usable space surrounding the pyridyl ring, the ethyl linker and near the 5-bromo position (shown in structure of PETT derivative). It was proposed that efficient use of this space by strategically designed functional groups would lead to high affinity binding and ultimately result in better inhibitors.

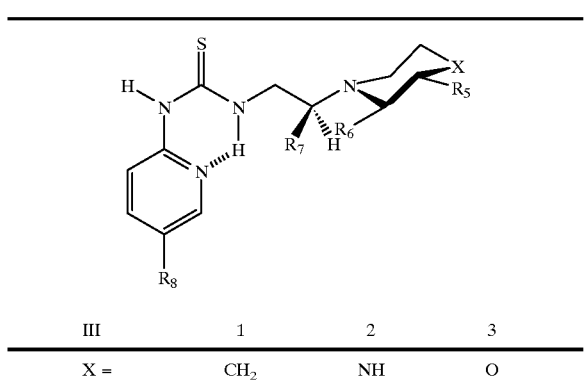

| III | 1 | 2 | 3 |
|---|---|---|---|
| X = | $CH_2$ | NH | O |

The effect of systematic substitutions of the phenyl ring of trovirdine with various heterocyclic rings was studied. This provides an alternative strategy to fit the compound into the relatively flexible and spacious Wing 2 region (as illustrated by the composite binding pocket). In the subsequent modeling studies these heterocyclic rings, which have a larger volume than the pyridyl ring of trovirdine, were shown to better fill the Wing 2 region of the composite binding pocket.

The piperidinyl, piperzinyl and morpholinyl rings of compounds III-1–3 are puckered and therefore occupy a larger overall volume than the planar pyridyl ring of trovirdine and are in close contact with residues Leu234 and Leu100, the latter of which can mutate to isoleucine, frequently found in a drug-resistant RT mutant strain. The encouraging results from efforts to make modifications perpendicular to the ring plane introduces new possibilities to develop more potent inhibitors of RT.

The heterocyclic rings which are conformationally more flexible than an aromatic ring may have the advantage of fitting an uncompromising binding pocket more effectively, despite the expense paid for loss of entropy upon binding. Various combinations of double substitutions at axial or equatorial positions of these heterocyclic rings would generate derivatives with a broader range of curvatures than trovirdine derivatives and would serve to better fit Wing 2 which itself contains some curvature.

Example 10

In Vitro Assays of Anti-HIV-1 Activity Using PETT Derivatives III

Compounds III-1 to III-3 were tested for anti-HIV activity in $HTLV_{IIIB}$-infected peripheral blood mononuclear cells. Anti-HIV activity was tested using the p24 immunoassay described above for Example 6. Cytotoxicity was also analyzed using a Microculture tetrazolium Assay (MTA), as described above for Example 6.

The data below in Table 7 show the inhibitory effects of PETT derivatives (compounds III-1–3) on p24 production in HIV-infected peripheral blood mononuclear cells and on viability of peripheral blood mononuclear cells. $IC_{50}$ values represent the concentration required to inhibit by 50% the activity of HIV replication as measured by assays of p24 production ($IC_{50}$ [p24]) or the concentration required to decrease cellular proliferation by 50% as measured by MTA ($IC_{50}$ [MTA]) (Uckun, et al., Antimicrobial Agents and Chemotherapy, 1998, 42, 383; Zarling, et al., Nature, 1990, 347, 92–95; Erice, et al., Antimicrob. Ag Chemother., 1993, 37, 835).

All three compounds III-1–3 were more potent than trovirdine for inhibitition of HIV. Our lead heterocyclic PETT derivatives, N-[2-(1-piperidinylethyl)]-N'-[2-(5-bromopyridyl)]-thiourea (compound III-1) and N-[2-(1-morpholinylethyl)]-N'-[2-(5-bromopyridyl)]-thiourea (compound 3) elicited potent anti-HIV activity with $IC_{50}$ values less than 1 nM for the inhibition of HIV replication (measured by p24 production in HIV-infected human peripheral blood mononuclear cells) and showed no detectable cytotoxicity (inhibition of cellular proliferation was >100 μM as measured by MTA) (Table 7).

TABLE 7

| Compound | R | $IC_{50}[p24]$ (μM) | $IC_{50}[MTA]$ (μM) | SI |
|---|---|---|---|---|
| III-1 | piperdinyl | <0.001 | >100 | >1 × 10^5 |
| III-2 | piperazinyl | 0.002 | >100 | >5 × 10^4 |

TABLE 7-continued

[Structure: Br-pyridyl-NH-C(=S)-NH-CH2CH2-R]

| Compound | R | IC$_{50}$[p24] ($\mu$M) | IC$_{50}$[MTA] ($\mu$M) | SI |
|---|---|---|---|---|
| III-3 | morpholinyl | <0.001 | >100 | >1 × 10$^5$ |
| Trovirdine | pyridyl | 0.007 | >100 | >1 × 10$^4$ |
| AZT | — | 0.004 | 50 | 7 × 10$^3$ |

Example 11

"SeeGap" Program for Analysis of Gap Space

To analyze the gap space between the binding pocket and complexed NNI, the "SeeGap" program was developed. The following instructions are for use of the program, whose code is listed below in Table 8:

Preparation:
1. Extract the source codes at the lines indicated. The first program is a C-shell command file and should be named as "SeeGap"; the second program should be named as "pdbmax.f"; the third "gridbox.f" and fourth "chgcolor.f".
2. Compile the source codes: for the first, chmod+x SeeGap; the second, third, and fourth by "f77–o file file.f".
3. You should now have the executive versions of the programs named as "SeeGap", "pdbmax", "gridbox" and "chgcolor". The preparation is ready.

Use the program:
1. Open "insightII" window, and read in the coordinates of the protein and the coordinates of the ligand. Next, assign the potential to both coordinates by builder module within "insightII" (see insight II manual).
2. Position the ligand in the binding site by a docking procedure, if the position of the ligand is unknown.
3. Using subset/interface command, determine the coordinates of the protein that immediately surround the ligand by a defined distance, e.g., 7 angstroms. Write out the coordinates and name it as "bind.pdb"; write out the coordinates of the ligand and name it as "ligand.pdb".
4. Adjust the input parameters in the command file "See-Gap" as appropriate.
5. Run the program by typing "SeeGap ligand.pdb bind.pdb>out&".
6. The results should be in three files: contact.pdb, which represents the grid points on the surface of the ligand and in contact with the protein residues; gap.pdb, which represents the grid points available for modification; and lig.pdb, which represents the grid points covering the ligand.
7. Use a molecular graphics software to display these coordinates.

TABLE 8A

C-shell command file "SeeGap"

```
#######C-shell command file "SeeGap",
cut below
#!/bin/csh
# chen mao, Nov. 8, 1997
grep "ATOM " $1 >fort.1
```

TABLE 8A-continued

C-shell command file "SeeGap"

```
grep "ATOM " $2 >fort.2
# modify expansion value (5.0 A) for the ligand
/usr2/mao/local/bin/pdbmax <<eof
5.0
eof
∩ modify the grid (1.0 A), too-small-grids may waste time
/usr2/mao/local/bin/gridbox <<eof
1.0
eof
# modify the distance cutoff considered to be close
/usr2/mao/local/bin/chgcolor <<eof
2.0
eof
grep " H " fort.30>contact.pdb
grep "END " fort.30>>contact.pdb
grep " N " fort.20>lig.pdb
grep "END " fort.30>>lig.pdb
grep " OH2" fort.30>gap.pdb
grep "END " fort.30>>gap.pdb
/bin/rm fort.1 fort.2 fort.30 fort.20
```

TABLE 8B

Program "pdbmax.f" to Determine Boundaries

```
PROGRAM "pdbmax.f" TO DETERMINED THE BOUNDARY OF
###THE COORDINATES, cut below #
     xmin = 9999.0
     xmax = -9999.0
       ymin = 9999.0
     ymax = -9999.0
       zmin = 9999.0
     zmax = -9999.0
     open(unit = 99, file = "boundary.out", status = "unknown")
     read (*,*)add
20     read(1,'(30x,3f8.3) ',end = 999)x,y,z
     if (x.lt.xmin) xmin = x
     if (y.lt.ymin) ymin = y
     if (z.lt.zmin) zmin = z
     if (x.gt.xmax) xmax = x
     if (y.gt.ymax) ymax = y
     if (z.gt.zmax) zmax = z
     go to 20
1000 format(a4,i7,2x,a1,a2,1x,a3,2x,i4,4x,3f8.3,2f6.2)
999  continue
     write(*,'("the extreme of the coordinates are")')
     write(*,'(6(3x,f6.1))')xmin,xmax,ymin,ymax,zmin,zmax
     xmin = xmin - add
     ymin = ymin - add
     zmin = zmin - add
     xmax = xmax + add
     ymax = ymax + add
     zmax = zmax + add
     write(99,'(6(3x,f6.1))')xmin,xmax,ymin,ymax,zmin,zmax
     stop
       end
```

TABLE 8C

Program "gridbox.f" to Generate Grids

```
# PROGRAM "gridbox.f" TO GENERATE GRIDS FOR THE
#BINDING SITE, cut below
         CHARACTER*1 ATOM1
         character*2 ATOM2
         CHARACTER*4 CHN
         character*4 RES
       integer xs, ys, zs
       parameter q = 1.0, w = 0.0
       write(*,'("step size in A")')
       open(unit = 99, file = "boundary.out", status = "old",readonly)
         read(*,*)step
```

TABLE 8C-continued

Program "gridbox.f" to Generate Grids

```
         CHN = 'ATOM'
         RES = 'TIP3'
         ATOM1 = 'O'
         ATOM2 = 'H2'
         ICNTS = 0
C        read the boundary of the box to generate grid
         write(*,'("six min max values ")')
         read (99,*)xmin, xmax, ymin, ymax, zmin, zmax
         s = (xmax − xmin)/step
         xs = s
         s = (ymax − ymin)/step
         ys = s
         s = (zmax − zmin)/step
         zs = s
         if (xs.lt.0.0.or.ys.lt.0.0.or.zs.lt.0.0) then
         write(*,'("nonsense input")')
         go to 999
         end if
         write (*,*)xs,ys,zs
         inum = xs*ys*zs
         write(*,*)inum
         if (inum.gt.25000) then
         write(*,'("too many grids")')
         go to 999
         end if
         do 100 n = 1, zs
         do 100 m = 1, ys
         do 100 l = 1, xs
         x1 = xmin + float(l) *step
         y1 = ymin + float(m) *step
         z1 = zmin + float(n) *step
         icnts = icnts + 1
100      write (10,1000) CHN,ICNTS,ATOM1,ATOM2,RES,
         1      icnts, x1,y1,z1,Q,W
1000         format(A4,I7,2X,A1,A2,1X,A4,I6,3X,3F8.3,2F6.2)
C        write (10,'("END ")')
999      stop
         end
```

TABLE 8D

Program "chgcolor.f" to Determine Contact Area and GAP

```
PROGRAM "chgcolor.f" TO DETERMINE THE CONTACT
AREA AND GAP, cut below #
         character*1 atom1, zatom1
         character*2 atom2, zatom2
         CHARACTER*4 chn, zchn
         character*4 res, zres
         integer iatom, izatom, ires, izres
         real u, v, w, q, zq, windex, zw
C set for delta distance value, please revise
C        parameter da=1.5
         write(*,'("distance cutoff")')
C da1 is for hydrogen, da2 for other kinds
         read (*,*)da
C        read (*,*)da1, da2
100      read (10,1000, end=199) chn,iatom,atom1,atom2,res,
         1      ires, u,v,w,q,windex
         rewind 1
130      read(1, 1000, end=198) zchn,izatom,zatom1,zatom2,zres,
         1      izres,x,y,z,zq,zw
C        if (zatom1.eq."H") then
C        da=da1
C        go to 133
C        end if
C        da=da2
133      delx=abs(u−x)
         dely=abs(v−y)
         delz=abs(w−z)
         if(delx.lt.da.and.dely.lt.da.and.delz.lt.da ) then
         dist=sqrt(delx*delx+dely*dely+delz*delz)
         if(dist.lt.da) then
         windex=windex+1.0
```

TABLE 8D-continued

Program "chgcolor.f" to Determine Contact Area and GAP

```
         atom1="N"
         atom2="  "
         go to 198
         end if
         end if
         go to 130
198      write (20,1000)chn,iatom,atom1,atom2,res,
         1      ires, u,v,w,q,windex
         go to 100
199      continue
         rewind 20
200      read (20,1000, end=299) chn,iatom,atom1,atom2,res,
         1      ires, u,v,w,q,windex
         rewind 2
230      read(2, 1000, end=298)
         zchn,izatom,zatom1,zatom2,zres,
         1      izres,x,y,z,zq,zw
C        if (zatom1.eq."H") then
C        da=da1
C        go to 233
C        end if
C        da=da2
233      delx=abs(u−x)
         dely=abs(v−y)
         delz=abs(w−z)
         if(delx.lt.da.and.dely.lt.da.and.delz.lt.da ) then
         dist=sqrt(delx*delx+dely*dely+delz*delz)
         if(dist.lt.da) then
         windex=windex+1.0
         atom1="C"
         atom2="  "
         go to 298
         end if
         end if
         go to 230
298      continue
         if (windex.eq.2.0) then
         atom1="H"
         atom2="  "
         end if
         write (30,1000)chn,iatom,atom1,atom2,res,
         1      ires, u,v,w,q,windex
         go to 200
299      continue
         write(30,'("END ")')
         stop
1000         format(A4,I7,2X,A1,A2,1X,A4,1x,I5,3X,3F8.3,2F6.2)
         end
###############
```

TABLE 9

Coordinates of Composite Binding Pocket

These coordinates can be entered into a molecular graphics program to generate a molecular surface representation of the composite binding pocket, which then can be used to design and evaluate inhibitors of RT.

| ATOM | 1 | O | H2O | 1 | 144.048 | −24.778 | 68.464 | inf | inf |
|---|---|---|---|---|---|---|---|---|---|
| ATOM | 2 | O | H2O | 2 | 144.416 | −24.592 | 68.433 | inf | inf |
| ATOM | 3 | O | H2O | 3 | 144.416 | −24.225 | 68.423 | inf | inf |
| ATOM | 4 | O | H2O | 4 | 143.694 | −25.486 | 68.876 | inf | inf |
| ATOM | 5 | O | H2O | 5 | 144.048 | −25.306 | 68.683 | inf | inf |
| ATOM | 6 | O | H2O | 6 | 144.749 | −25.257 | 68.756 | inf | |
| ATOM | 7 | O | H2O | 7 | 143.349 | −24.944 | 68.703 | inf | inf |
| ATOM | 8 | O | H2O | 8 | 144.790 | −24.969 | 68.630 | inf | inf |
| ATOM | 9 | O | H2O | 9 | 143.080 | −24.603 | 68.775 | inf | inf |
| ATOM | 10 | O | H2O | 10 | 145.130 | −24.581 | 68.682 | inf | inf |
| ATOM | 11 | O | H2O | 11 | 143.639 | −24.225 | 68.487 | inf | inf |
| ATOM | 12 | O | H2O | 12 | 145.513 | −24.404 | 68.846 | inf | inf |
| ATOM | 13 | O | H2O | 13 | 143.655 | −23.832 | 68.549 | inf | inf |
| ATOM | 14 | O | H2O | 14 | 145.157 | −23.856 | 68.637 | inf | inf |
| ATOM | 15 | O | H2O | 15 | 143.471 | −23.455 | 68.774 | inf | inf |
| ATOM | 16 | O | H2O | 16 | 144.786 | −23.480 | 68.619 | inf | inf |
| ATOM | 17 | O | H2O | 17 | 143.670 | −23.285 | 68.803 | inf | inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| ATOM | 18 | O | H2O | 18 | 144.785 | −23.149 | 68.737 | inf | inf |
|---|---|---|---|---|---|---|---|---|---|
| ATOM | 19 | O | H2O | 19 | 144.417 | −22.949 | 68.853 | inf | inf |
| ATOM | 20 | O | H2O | 20 | 143.693 | −25.667 | 69.048 | inf | inf |
| ATOM | 21 | O | H2O | 21 | 144.417 | −25.702 | 69.012 | inf | inf |
| ATOM | 22 | O | H2O | 22 | 143.280 | −25.554 | 69.161 | inf | inf |
| ATOM | 23 | O | H2O | 23 | 145.154 | −25.515 | 69.200 | inf | inf |
| ATOM | 24 | O | H2O | 24 | 142.936 | −24.965 | 69.009 | inf | inf |
| ATOM | 25 | O | H2O | 25 | 142.683 | −24.618 | 69.149 | inf | inf |
| ATOM | 26 | O | H2O | 26 | 142.673 | −24.225 | 69.139 | inf | inf |
| ATOM | 27 | O | H2O | 27 | 146.037 | −24.225 | 69.239 | inf | inf |
| ATOM | 28 | O | H2O | 28 | 146.042 | −23.856 | 69.233 | inf | inf |
| ATOM | 29 | O | H2O | 29 | 145.586 | −23.456 | 68.921 | inf | inf |
| ATOM | 30 | O | H2O | 30 | 143.152 | −23.144 | 69.225 | inf | inf |
| ATOM | 31 | O | H2O | 31 | 145.515 | −23.125 | 69.025 | inf | inf |
| ATOM | 32 | O | H2O | 32 | 143.661 | −22.890 | 69.155 | inf | inf |
| ATOM | 33 | O | H2O | 33 | 144.786 | −22.742 | 69.007 | inf | inf |
| ATOM | 34 | O | H2O | 34 | 144.063 | −22.602 | 69.236 | inf | inf |
| ATOM | 35 | O | H2O | 35 | 144.048 | −26.097 | 69.620 | inf | inf |
| ATOM | 36 | O | H2O | 36 | 144.417 | −25.997 | 69.413 | inf | inf |
| ATOM | 37 | O | H2O | 37 | 143.287 | −25.730 | 69.365 | inf | inf |
| ATOM | 38 | O | H2O | 38 | 145.148 | −25.868 | 69.584 | inf | inf |
| ATOM | 39 | O | H2O | 39 | 142.892 | −25.364 | 69.350 | inf | inf |
| ATOM | 40 | O | H2O | 40 | 142.606 | −25.130 | 69.584 | inf | inf |
| ATOM | 41 | O | H2O | 41 | 145.857 | −25.125 | 69.596 | inf | inf |
| ATOM | 42 | O | H2O | 42 | 145.964 | −24.629 | 69.323 | inf | inf |
| ATOM | 43 | O | H2O | 43 | 146.208 | −24.258 | 69.503 | inf | inf |
| ATOM | 44 | O | H2O | 44 | 142.554 | −23.662 | 69.558 | inf | inf |
| ATOM | 45 | O | H2O | 45 | 142.828 | −23.175 | 69.610 | inf | inf |
| ATOM | 46 | O | H2O | 46 | 143.260 | −22.858 | 69.517 | inf | inf |
| ATOM | 47 | O | H2O | 47 | 145.718 | −22.739 | 69.559 | inf | inf |
| ATOM | 48 | O | H2O | 48 | 143.886 | −22.425 | 69.590 | inf | inf |
| ATOM | 49 | O | H2O | 49 | 144.975 | −22.345 | 69.548 | inf | inf |
| ATOM | 50 | O | H2O | 50 | 144.786 | −22.277 | 69.595 | inf | inf |
| ATOM | 51 | O | H2O | 51 | 144.048 | −26.251 | 69.938 | inf | inf |
| ATOM | 52 | O | H2O | 52 | 144.994 | −26.125 | 69.920 | inf | inf |
| ATOM | 53 | O | H2O | 53 | 145.525 | −25.701 | 69.751 | inf | inf |
| ATOM | 54 | O | H2O | 54 | 142.858 | −25.603 | 69.941 | inf | inf |
| ATOM | 55 | O | H2O | 55 | 142.410 | −24.956 | 69.939 | inf | inf |
| ATOM | 56 | O | H2O | 56 | 146.247 | −24.586 | 69.759 | inf | inf |
| ATOM | 57 | O | H2O | 57 | 146.322 | −24.242 | 69.726 | inf | inf |
| ATOM | 58 | O | H2O | 58 | 146.447 | −23.856 | 69.936 | inf | inf |
| ATOM | 59 | O | H2O | 59 | 146.368 | −23.509 | 69.971 | inf | inf |
| ATOM | 60 | O | H2O | 60 | 146.277 | −23.296 | 69.932 | inf | inf |
| ATOM | 61 | O | H2O | 61 | 145.876 | −22.762 | 69.762 | inf | inf |
| ATOM | 62 | O | H2Q | 62 | 143.833 | −22.310 | 69.916 | inf | inf |
| ATOM | 63 | O | H2O | 63 | 145.829 | −22.628 | 69.962 | inf | inf |
| ATOM | 64 | O | H2O | 64 | 145.143 | −22.230 | 69.948 | inf | inf |
| ATOM | 65 | O | H2O | 65 | 144.048 | −26.591 | 70.339 | inf | inf |
| ATOM | 66 | O | H2O | 66 | 144.605 | −26.461 | 70.287 | inf | inf |
| ATOM | 67 | O | H2O | 67 | 144.849 | −26.350 | 70.242 | inf | inf |
| ATOM | 68 | O | H2O | 68 | 143.010 | −25.838 | 70.326 | inf | inf |
| ATOM | 69 | O | H2O | 69 | 145.844 | −25.653 | 70.169 | inf | inf |
| ATOM | 70 | O | H2O | 70 | 142.505 | −25.253 | 70.305 | inf | inf |
| ATOM | 71 | O | H2O | 71 | 146.408 | −25.313 | 70.366 | inf | inf |
| ATOM | 72 | O | H2O | 72 | 142.287 | −24.619 | 70.305 | inf | inf |
| ATOM | 73 | O | H2O | 73 | 142.270 | −24.225 | 70.305 | inf | inf |
| ATOM | 74 | O | H2O | 74 | 146.581 | −23.856 | 70.155 | inf | inf |
| ATOM | 75 | O | H2O | 75 | 146.640 | −23.667 | 70.298 | inf | inf |
| ATOM | 76 | O | H2O | 76 | 146.387 | −23.165 | 70.341 | inf | inf |
| ATOM | 77 | O | H2O | 77 | 146.235 | −22.946 | 70.319 | inf | inf |
| ATOM | 78 | O | H2O | 78 | 145.533 | −22.364 | 70.118 | inf | inf |
| ATOM | 79 | O | H2O | 79 | 144.038 | −22.156 | 70.305 | inf | inf |
| ATOM | 80 | O | H2O | 80 | 145.471 | −22.274 | 70.333 | inf | inf |
| ATOM | 81 | O | H2O | 81 | 144.048 | −27.016 | 70.623 | inf | inf |
| ATOM | 82 | O | H2O | 82 | 144.634 | −26.841 | 70.626 | inf | inf |
| ATOM | 83 | O | H2O | 83 | 144.819 | −26.507 | 70.435 | inf | inf |
| ATOM | 84 | O | H2O | 84 | 145.332 | −26.427 | 70.685 | inf | inf |
| ATOM | 85 | O | H2O | 85 | 145.880 | −26.228 | 70.717 | inf | inf |
| ATOM | 86 | O | H2O | 86 | 142.907 | −25.909 | 70.653 | inf | inf |
| ATOM | 87 | O | H2O | 87 | 146.588 | −25.657 | 70.623 | inf | inf |
| ATOM | 88 | O | H2O | 88 | 147.374 | −25.700 | 70.660 | inf | inf |
| ATOM | 89 | O | H2O | 89 | 148.108 | −25.686 | 70.594 | inf | inf |
| ATOM | 90 | O | H2O | 90 | 142.531 | −25.283 | 70.673 | inf | inf |
| ATOM | 91 | O | H2O | 91 | 147.001 | −25.530 | 70.644 | inf | inf |
| ATOM | 92 | O | H2O | 92 | 148.427 | −25.333 | 70.643 | inf | inf |
| ATOM | 93 | O | H2O | 93 | 146.982 | −24.943 | 70.558 | inf | inf |
| ATOM | 94 | O | H2O | 94 | 148.109 | −25.140 | 70.625 | inf | inf |
| ATOM | 95 | O | H2O | 95 | 147.195 | −24.587 | 70.651 | inf | inf |
| ATOM | 96 | O | H2O | 96 | 147.177 | −24.225 | 70.696 | inf | inf |
| ATOM | 97 | O | H2O | 97 | 142.471 | −23.515 | 70.647 | inf | inf |
| ATOM | 98 | O | H2O | 98 | 142.595 | −23.318 | 70.666 | inf | inf |
| ATOM | 99 | O | H2O | 99 | 142.934 | −22.926 | 70.677 | inf | inf |
| ATOM | 100 | O | H2O | 100 | 146.583 | −22.969 | 70.735 | inf | inf |
| ATOM | 101 | O | H2O | 101 | 146.022 | −22.436 | 70.730 | inf | inf |
| ATOM | 102 | O | H2O | 102 | 144.417 | −22.087 | 70.674 | inf | inf |
| ATOM | 103 | O | H2O | 103 | 145.844 | −22.277 | 70.742 | inf | inf |
| ATOM | 104 | O | H2O | 104 | 144.233 | −27.553 | 71.039 | inf | inf |
| ATOM | 105 | O | H2O | 105 | 143.655 | −27.432 | 70.974 | inf | inf |
| ATOM | 106 | O | H2O | 106 | 144.442 | −27.438 | 70.968 | inf | inf |
| ATOM | 107 | O | H2O | 107 | 142.971 | −26.975 | 71.068 | inf | inf |
| ATOM | 108 | O | H2O | 108 | 144.850 | −26.872 | 70.763 | inf | inf |
| ATOM | 109 | O | H2O | 109 | 142.790 | −26.440 | 71.066 | inf | inf |
| ATOM | 110 | O | H2O | 110 | 145.888 | −26.614 | 71.059 | inf | inf |
| ATOM | 111 | O | H2O | 111 | 147.185 | −26.441 | 71.041 | inf | inf |
| ATOM | 112 | O | H2O | 112 | 148.109 | −26.648 | 71.020 | inf | inf |
| ATOM | 113 | O | H2O | 113 | 148.669 | −26.449 | 71.032 | inf | inf |
| ATOM | 114 | O | H2O | 114 | 146.285 | −26.324 | 70.974 | inf | inf |
| ATOM | 115 | O | H2O | 115 | 147.001 | −26.084 | 70.828 | inf | inf |
| ATOM | 116 | O | H2O | 116 | 148.503 | −26.108 | 70.772 | inf | inf |
| ATOM | 117 | O | H2O | 117 | 142.649 | −25.772 | 70.972 | inf | inf |
| ATOM | 118 | O | H2O | 118 | 142.535 | −25.326 | 71.039 | inf | inf |
| ATOM | 119 | O | H2O | 119 | 142.463 | −24.937 | 71.041 | inf | inf |
| ATOM | 120 | O | H2O | 120 | 148.837 | −24.973 | 70.888 | inf | inf |
| ATOM | 121 | O | H2O | 121 | 147.762 | −24.573 | 70.772 | inf | inf |
| ATOM | 122 | O | H2O | 122 | 149.033 | −24.594 | 71.039 | inf | inf |
| ATOM | 123 | O | H2O | 123 | 148.108 | −24.225 | 70.852 | inf | inf |
| ATOM | 124 | O | H2O | 124 | 142.459 | −23.880 | 71.019 | inf | inf |
| ATOM | 125 | O | H2O | 125 | 148.477 | −23.866 | 70.928 | inf | inf |
| ATOM | 126 | O | H2O | 126 | 142.550 | −23.661 | 71.054 | inf | inf |
| ATOM | 127 | O | H2O | 127 | 147.710 | −23.518 | 70.952 | inf | inf |
| ATOM | 128 | O | H2O | 128 | 148.845 | −23.672 | 71.048 | inf | inf |
| ATOM | 129 | O | H2O | 129 | 147.390 | −23.272 | 70.974 | inf | inf |
| ATOM | 130 | O | H2O | 130 | 143.004 | −22.992 | 71.018 | inf | inf |
| ATOM | 131 | O | H2O | 131 | 147.021 | −22.918 | 71.009 | inf | inf |
| ATOM | 132 | O | H2O | 132 | 143.843 | −22.331 | 71.057 | inf | inf |
| ATOM | 133 | O | H2O | 133 | 144.057 | −22.209 | 71.039 | inf | inf |
| ATOM | 134 | O | H2O | 134 | 145.155 | −22.003 | 70.856 | inf | inf |
| ATOM | 135 | O | H2O | 135 | 146.253 | −22.218 | 71.067 | inf | inf |
| ATOM | 136 | O | H2O | 136 | 145.894 | −21.890 | 71.108 | inf | inf |
| ATOM | 137 | O | H2O | 137 | 143.673 | −27.752 | 71.404 | inf | inf |
| ATOM | 138 | O | H2O | 138 | 144.425 | −27.759 | 71.401 | inf | inf |
| ATOM | 139 | O | H2O | 139 | 142.960 | −27.339 | 71.427 | inf | inf |
| ATOM | 140 | O | H2O | 140 | 145.148 | −27.353 | 71.418 | inf | inf |
| ATOM | 141 | O | H2O | 141 | 145.550 | −27.062 | 71.366 | inf | inf |
| ATOM | 142 | O | H2O | 142 | 146.233 | −26.749 | 71.320 | inf | inf |
| ATOM | 143 | O | H2O | 143 | 147.403 | −26.893 | 71.480 | inf | inf |
| ATOM | 144 | O | H2O | 144 | 147.735 | −26.822 | 71.219 | inf | inf |
| ATOM | 145 | O | H2O | 145 | 148.468 | −26.781 | 71.247 | inf | inf |
| ATOM | 146 | O | H2O | 146 | 142.643 | −26.440 | 71.276 | inf | inf |
| ATOM | 147 | O | H2O | 147 | 147.003 | −26.730 | 71.337 | inf | inf |
| ATOM | 148 | O | H2O | 148 | 142.446 | −26.051 | 71.452 | inf | inf |
| ATOM | 149 | O | H2O | 149 | 149.369 | −26.060 | 71.434 | inf | inf |
| ATOM | 150 | O | H2O | 150 | 149.447 | −25.719 | 71.367 | inf | inf |
| ATOM | 151 | O | H2O | 151 | 142.424 | −24.951 | 71.422 | inf | inf |
| ATOM | 152 | O | H2O | 152 | 149.685 | −24.933 | 71.469 | inf | inf |
| ATOM | 153 | O | H2O | 153 | 149.734 | −24.594 | 71.448 | inf | inf |
| ATOM | 154 | O | H2O | 154 | 149.268 | −24.225 | 71.124 | inf | inf |
| ATOM | 155 | O | H2O | 155 | 142.731 | −23.841 | 71.448 | inf | inf |
| ATOM | 156 | O | H2O | 156 | 142.812 | −23.520 | 71.368 | inf | inf |
| ATOM | 157 | O | H2O | 157 | 149.748 | −23.478 | 71.434 | inf | inf |
| ATOM | 158 | O | H2O | 158 | 147.423 | −23.050 | 71.114 | inf | inf |
| ATOM | 159 | O | H2O | 159 | 148.867 | −23.117 | 71.149 | inf | inf |
| ATOM | 160 | O | H2O | 160 | 143.329 | −22.764 | 71.216 | inf | inf |
| ATOM | 161 | O | H2O | 161 | 147.365 | −22.759 | 71.245 | inf | inf |
| ATOM | 162 | O | H2O | 162 | 148.847 | −22.748 | 71.181 | inf | inf |
| ATOM | 163 | O | H2O | 163 | 143.692 | −22.585 | 71.396 | inf | inf |
| ATOM | 164 | O | H2O | 164 | 147.183 | −22.382 | 71.418 | inf | inf |
| ATOM | 165 | O | H2O | 165 | 148.288 | −22.374 | 71.403 | inf | inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| ATOM | 166 | O | H2O | 166 | 149.548 | −22.416 | 71.339 | inf | inf |
|---|---|---|---|---|---|---|---|---|---|
| ATOM | 167 | O | H2O | 167 | 144.299 | −22.076 | 71.413 | inf | inf |
| ATOM | 168 | O | H2O | 168 | 146.991 | −22.215 | 71.443 | inf | inf |
| ATOM | 169 | O | H2O | 169 | 149.576 | −22.203 | 71.431 | inf | inf |
| ATOM | 170 | O | H2O | 170 | 145.001 | −21.694 | 71.453 | inf | inf |
| ATOM | 171 | O | H2O | 171 | 146.443 | −21.649 | 71.443 | inf | inf |
| ATOM | 172 | O | H2O | 172 | 145.894 | −21.452 | 71.403 | inf | inf |
| ATOM | 173 | O | H2O | 173 | 143.692 | −27.877 | 71.623 | inf | inf |
| ATOM | 174 | O | H2O | 174 | 144.406 | −27.883 | 71.619 | inf | inf |
| ATOM | 175 | O | H2O | 175 | 144.818 | −27.779 | 71.750 | inf | inf |
| ATOM | 176 | O | H2O | 176 | 142.717 | −27.204 | 71.769 | inf | inf |
| ATOM | 177 | O | H2O | 177 | 145.720 | −27.202 | 71.768 | inf | inf |
| ATOM | 178 | O | H2O | 178 | 145.935 | −27.086 | 71.728 | inf | inf |
| ATOM | 179 | O | H2O | 179 | 147.001 | −26.972 | 71.791 | inf | inf |
| ATOM | 180 | O | H2O | 180 | 148.495 | −27.054 | 71.756 | inf | inf |
| ATOM | 181 | O | H2O | 181 | 142.384 | −26.441 | 71.781 | inf | inf |
| ATOM | 182 | O | H2O | 182 | 142.297 | −26.096 | 71.743 | inf | inf |
| ATOM | 183 | O | H2O | 183 | 149.650 | −25.913 | 71.745 | inf | inf |
| ATOM | 184 | O | H2O | 184 | 149.804 | −25.332 | 71.759 | inf | inf |
| ATOM | 185 | O | H2O | 185 | 142.522 | −24.758 | 71.783 | inf | inf |
| ATOM | 186 | O | H2O | 186 | 150.044 | −24.594 | 71.845 | inf | inf |
| ATOM | 187 | O | H2O | 187 | 142.920 | −23.846 | 71.616 | inf | inf |
| ATOM | 188 | O | H2O | 188 | 150.094 | −23.840 | 71.811 | inf | inf |
| ATOM | 189 | O | H2O | 189 | 150.140 | −23.487 | 71.781 | inf | inf |
| ATOM | 190 | O | H2O | 190 | 149.996 | −23.128 | 71.524 | inf | inf |
| ATOM | 191 | O | H2O | 191 | 143.870 | −22.754 | 71.775 | inf | inf |
| ATOM | 192 | O | H2O | 192 | 144.036 | −22.552 | 71.787 | inf | inf |
| ATOM | 193 | O | H2O | 193 | 148.080 | −22.338 | 71.501 | inf | inf |
| ATOM | 194 | O | H2O | 194 | 147.010 | −21.997 | 71.566 | inf | inf |
| ATOM | 195 | O | H2O | 195 | 148.458 | −21.971 | 71.538 | inf | inf |
| ATOM | 196 | O | H2O | 196 | 149.817 | −21.962 | 71.710 | inf | inf |
| ATOM | 197 | O | H2O | 197 | 144.643 | −21.670 | 71.794 | inf | inf |
| ATOM | 198 | O | H2O | 198 | 147.377 | −21.815 | 71.758 | inf | inf |
| ATOM | 199 | O | H2O | 199 | 148.660 | −21.627 | 71.771 | inf | inf |
| ATOM | 200 | O | H2O | 200 | 149.604 | −21.778 | 71.734 | inf | inf |
| ATOM | 201 | O | H2O | 201 | 145.510 | −21.250 | 71.547 | inf | inf |
| ATOM | 202 | O | H2O | 202 | 146.868 | −21.251 | 71.710 | inf | inf |
| ATOM | 203 | O | H2O | 203 | 145.161 | −21.090 | 71.791 | inf | inf |
| ATOM | 204 | O | H2O | 204 | 146.261 | −20.905 | 71.603 | inf | inf |
| ATOM | 205 | O | H2O | 205 | 145.710 | −20.536 | 71.791 | inf | inf |
| ATOM | 206 | O | H2O | 206 | 146.621 | −20.740 | 71.815 | inf | inf |
| ATOM | 207 | O | H2O | 207 | 143.707 | −28.248 | 72.013 | inf | inf |
| ATOM | 208 | O | H2O | 208 | 144.405 | −28.256 | 71.996 | inf | inf |
| ATOM | 209 | O | H2O | 209 | 143.294 | −27.935 | 71.947 | inf | inf |
| ATOM | 210 | O | H2O | 210 | 142.946 | −27.729 | 72.153 | inf | inf |
| ATOM | 211 | O | H2O | 211 | 145.390 | −27.597 | 72.111 | inf | inf |
| ATOM | 212 | O | H2O | 212 | 145.884 | −27.333 | 72.171 | inf | inf |
| ATOM | 213 | O | H2O | 213 | 147.742 | −27.170 | 71.967 | inf | inf |
| ATOM | 214 | O | H2O | 214 | 142.440 | −26.773 | 72.151 | inf | inf |
| ATOM | 215 | O | H2O | 215 | 147.002 | −27.056 | 72.135 | inf | inf |
| ATOM | 216 | O | H2O | 216 | 149.074 | −26.861 | 72.124 | inf | inf |
| ATOM | 217 | O | H2O | 217 | 149.521 | −26.560 | 72.216 | inf | inf |
| ATOM | 218 | O | H2O | 218 | 142.208 | −26.069 | 71.967 | inf | inf |
| ATOM | 219 | O | H2O | 219 | 142.199 | −25.701 | 71.966 | inf | inf |
| ATOM | 220 | O | H2O | 220 | 142.187 | −25.515 | 72.147 | inf | inf |
| ATOM | 221 | O | H2O | 221 | 142.397 | −24.970 | 72.151 | inf | inf |
| ATOM | 222 | O | H2O | 222 | 142.720 | −24.572 | 72.153 | inf | inf |
| ATOM | 223 | O | H2O | 223 | 143.061 | −24.180 | 72.171 | inf | inf |
| ATOM | 224 | O | H2O | 224 | 143.358 | −23.534 | 71.918 | inf | inf |
| ATOM | 225 | O | H2O | 225 | 150.315 | −23.667 | 72.155 | inf | inf |
| ATOM | 226 | O | H2O | 226 | 143.910 | −23.165 | 72.103 | inf | inf |
| ATOM | 227 | O | H2O | 227 | 144.088 | −22.957 | 72.119 | inf | inf |
| ATOM | 228 | O | H2O | 228 | 144.267 | −22.388 | 72.138 | inf | inf |
| ATOM | 229 | O | H2O | 229 | 144.380 | −22.178 | 72.162 | inf | inf |
| ATOM | 230 | O | H2O | 230 | 150.348 | −22.182 | 72.139 | inf | inf |
| ATOM | 231 | O | H2O | 231 | 148.108 | −21.617 | 71.951 | inf | inf |
| ATOM | 232 | O | H2O | 232 | 150.013 | −21.767 | 72.104 | inf | inf |
| ATOM | 233 | O | H2O | 233 | 147.340 | −21.307 | 72.000 | inf | inf |
| ATOM | 234 | O | H2O | 234 | 148.473 | −21.440 | 72.140 | inf | inf |
| ATOM | 235 | O | H2O | 235 | 144.704 | −20.904 | 72.218 | inf | inf |
| ATOM | 236 | O | H2O | 236 | 147.177 | −20.908 | 72.158 | inf | inf |
| ATOM | 237 | O | H2O | 237 | 145.147 | −20.533 | 71.955 | inf | inf |
| ATOM | 238 | O | H2O | 238 | 146.825 | −20.525 | 72.144 | inf | inf |
| ATOM | 239 | O | H2O | 239 | 144.833 | −20.164 | 72.106 | inf | inf |
| ATOM | 240 | O | H2O | 240 | 146.241 | −20.189 | 72.032 | inf | inf |
| ATOM | 241 | O | H2O | 241 | 144.952 | −19.783 | 72.107 | inf | inf |
| ATOM | 242 | O | H2O | 242 | 146.216 | −19.842 | 72.107 | inf | inf |
| ATOM | 243 | O | H2O | 243 | 145.525 | −19.468 | 72.091 | inf | inf |
| ATOM | 244 | O | H2O | 244 | 145.524 | −19.285 | 72.215 | inf | inf |
| ATOM | 245 | O | H2O | 245 | 144.048 | −28.821 | 72.532 | inf | inf |
| ATOM | 246 | O | H2O | 246 | 144.620 | −28.691 | 72.489 | inf | inf |
| ATOM | 247 | O | H2O | 247 | 144.840 | −28.339 | 72.255 | inf | inf |
| ATOM | 248 | O | H2O | 248 | 145.273 | −28.245 | 72.573 | inf | inf |
| ATOM | 249 | O | H2O | 249 | 145.206 | −27.957 | 72.285 | inf | inf |
| ATOM | 250 | O | H2O | 250 | 145.561 | −27.779 | 72.473 | inf | inf |
| ATOM | 251 | O | H2O | 251 | 142.595 | −27.218 | 72.480 | inf | inf |
| ATOM | 252 | O | H2O | 252 | 146.633 | −27.181 | 72.334 | inf | inf |
| ATOM | 253 | O | H2O | 253 | 147.370 | −27.155 | 72.339 | inf | inf |
| ATOM | 254 | O | H2O | 254 | 142.416 | −26.796 | 72.520 | inf | inf |
| ATOM | 255 | O | H2O | 255 | 149.241 | −26.847 | 72.309 | inf | inf |
| ATOM | 256 | O | H2O | 256 | 149.756 | −26.795 | 72.547 | inf | inf |
| ATOM | 257 | O | H2O | 257 | 150.146 | −26.445 | 72.502 | inf | inf |
| ATOM | 258 | O | H2O | 258 | 150.259 | −26.038 | 72.429 | inf | inf |
| ATOM | 259 | O | H2O | 259 | 150.293 | −25.686 | 72.382 | inf | inf |
| ATOM | 260 | O | H2O | 260 | 150.311 | −25.332 | 72.353 | inf | inf |
| ATOM | 261 | O | H2O | 261 | 150.496 | −24.963 | 72.533 | inf | inf |
| ATOM | 262 | O | H2O | 262 | 150.406 | −24.631 | 72.557 | inf | inf |
| ATOM | 263 | O | H2O | 263 | 150.332 | −24.408 | 72.517 | inf | inf |
| ATOM | 264 | O | H2O | 264 | 150.307 | −23.852 | 72.338 | inf | inf |
| ATOM | 265 | O | H2O | 265 | 143.671 | −23.664 | 72.523 | inf | inf |
| ATOM | 266 | O | H2O | 266 | 144.054 | −23.308 | 72.517 | inf | inf |
| ATOM | 267 | O | H2O | 267 | 150.636 | −22.748 | 72.488 | inf | inf |
| ATOM | 268 | O | H2O | 268 | 150.564 | −22.365 | 72.506 | inf | inf |
| ATOM | 269 | O | H2O | 269 | 144.546 | −21.640 | 72.520 | inf | inf |
| ATOM | 270 | O | H2O | 270 | 144.506 | −21.295 | 72.521 | inf | inf |
| ATOM | 271 | O | H2O | 271 | 148.847 | −21.270 | 72.335 | inf | inf |
| ATOM | 272 | O | H2O | 272 | 149.923 | −21.503 | 72.536 | inf | inf |
| ATOM | 273 | O | H2O | 273 | 147.750 | −21.063 | 72.513 | inf | inf |
| ATOM | 274 | O | H2O | 274 | 149.215 | −21.213 | 72.561 | inf | inf |
| ATOM | 275 | O | H2O | 275 | 144.701 | −20.533 | 72.216 | inf | inf |
| ATOM | 276 | O | H2O | 276 | 144.291 | −20.164 | 72.559 | inf | inf |
| ATOM | 277 | O | H2O | 277 | 147.001 | −20.349 | 72.520 | inf | inf |
| ATOM | 278 | O | H2O | 278 | 146.596 | −19.809 | 72.371 | inf | inf |
| ATOM | 279 | O | H2O | 279 | 144.782 | −19.424 | 72.329 | inf | inf |
| ATOM | 280 | O | H2O | 280 | 146.486 | −19.395 | 72.481 | inf | inf |
| ATOM | 281 | O | H2O | 281 | 145.159 | −19.062 | 72.347 | inf | inf |
| ATOM | 282 | O | H2O | 282 | 146.294 | −19.210 | 72.473 | inf | inf |
| ATOM | 283 | O | H2O | 283 | 145.525 | −18.765 | 72.451 | inf | inf |
| ATOM | 284 | O | H2O | 284 | 145.524 | −18.548 | 72.587 | inf | inf |
| ATOM | 285 | O | H2O | 285 | 143.655 | −28.924 | 72.853 | inf | inf |
| ATOM | 286 | O | H2O | 286 | 144.789 | −28.850 | 72.884 | inf | inf |
| ATOM | 287 | O | H2O | 287 | 142.895 | −28.315 | 72.675 | inf | inf |
| ATOM | 288 | O | H2O | 288 | 145.572 | −27.954 | 72.657 | inf | inf |
| ATOM | 289 | O | H2O | 289 | 142.485 | −27.547 | 72.922 | inf | inf |
| ATOM | 290 | O | H2O | 290 | 146.244 | −27.683 | 72.938 | inf | inf |
| ATOM | 291 | O | H2O | 291 | 146.672 | −27.456 | 72.863 | inf | inf |
| ATOM | 292 | O | H2O | 292 | 147.551 | −27.151 | 72.889 | inf | inf |
| ATOM | 293 | O | H2O | 293 | 148.476 | −27.172 | 72.705 | inf | inf |
| ATOM | 294 | O | H2O | 294 | 149.218 | −27.105 | 72.738 | inf | inf |
| ATOM | 295 | O | H2O | 295 | 148.109 | −27.148 | 72.891 | inf | inf |
| ATOM | 296 | O | H2O | 296 | 149.954 | −27.067 | 72.816 | inf | inf |
| ATOM | 297 | O | H2O | 297 | 142.307 | −26.459 | 72.889 | inf | inf |
| ATOM | 298 | O | H2O | 298 | 150.882 | −26.444 | 72.884 | inf | inf |
| ATOM | 299 | O | H2O | 299 | 151.038 | −26.047 | 72.773 | inf | inf |
| ATOM | 300 | O | H2O | 300 | 142.238 | −25.701 | 72.926 | inf | inf |
| ATOM | 301 | O | H2O | 301 | 142.319 | −25.313 | 72.918 | inf | inf |
| ATOM | 302 | O | H2O | 302 | 142.449 | −25.005 | 72.868 | inf | inf |
| ATOM | 303 | O | H2O | 303 | 142.596 | −24.804 | 72.879 | inf | inf |
| ATOM | 304 | O | H2O | 304 | 142.983 | −24.473 | 72.868 | inf | inf |
| ATOM | 305 | O | H2O | 305 | 150.375 | −24.223 | 72.681 | inf | inf |
| ATOM | 306 | O | H2O | 306 | 143.829 | −23.829 | 72.923 | inf | inf |
| ATOM | 307 | O | H2O | 307 | 144.187 | −23.457 | 72.919 | inf | inf |
| ATOM | 308 | O | H2O | 308 | 144.433 | −22.753 | 72.702 | inf | inf |
| ATOM | 309 | O | H2O | 309 | 144.507 | −22.378 | 72.891 | inf | inf |
| ATOM | 310 | O | H2O | 310 | 144.506 | −21.640 | 72.865 | inf | inf |
| ATOM | 311 | O | H2O | 311 | 149.407 | −21.230 | 72.889 | inf | inf |
| ATOM | 312 | O | H2O | 312 | 144.269 | −20.878 | 72.901 | inf | inf |
| ATOM | 313 | O | H2O | 313 | 148.093 | −21.141 | 72.906 | inf | inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| ATOM | 314 | O | H2O | 314 | 144.164 | −20.553 | 72.860 | inf | inf |
|---|---|---|---|---|---|---|---|---|---|
| ATOM | 315 | O | H2O | 315 | 147.019 | −20.158 | 72.693 | inf | inf |
| ATOM | 316 | O | H2O | 316 | 147.029 | −19.967 | 72.873 | inf | inf |
| ATOM | 317 | O | H2O | 317 | 146.823 | −19.421 | 72.885 | inf | inf |
| ATOM | 318 | O | H2O | 318 | 146.568 | −19.105 | 72.785 | inf | inf |
| ATOM | 319 | O | H2O | 319 | 144.769 | −18.654 | 72.654 | inf | inf |
| ATOM | 320 | O | H2O | 320 | 146.585 | −18.900 | 72.927 | inf | inf |
| ATOM | 321 | O | H2O | 321 | 144.967 | −18.297 | 72.871 | inf | inf |
| ATOM | 322 | O | H2O | 322 | 146.251 | −18.515 | 72.901 | inf | inf |
| ATOM | 323 | O | H2O | 323 | 143.679 | −29.093 | 73.301 | inf | inf |
| ATOM | 324 | O | H2O | 324 | 144.048 | −29.055 | 73.069 | inf | inf |
| ATOM | 325 | O | H2O | 325 | 144.770 | −28.976 | 73.106 | inf | inf |
| ATOM | 326 | O | H2O | 326 | 142.958 | −28.633 | 73.087 | inf | inf |
| ATOM | 327 | O | H2O | 327 | 145.380 | −28.694 | 73.227 | inf | inf |
| ATOM | 328 | O | H2O | 328 | 145.577 | −28.329 | 73.048 | inf | inf |
| ATOM | 329 | O | H2O | 329 | 142.521 | −27.931 | 73.052 | inf | inf |
| ATOM | 330 | O | H2O | 330 | 142.378 | −27.547 | 73.255 | inf | inf |
| ATOM | 331 | O | H2O | 331 | 146.704 | −27.506 | 73.258 | inf | inf |
| ATOM | 332 | O | H2O | 332 | 148.291 | −27.190 | 73.258 | inf | inf |
| ATOM | 333 | O | H2O | 333 | 149.222 | −27.345 | 73.264 | inf | inf |
| ATOM | 334 | O | H2O | 334 | 149.954 | −27.252 | 72.999 | inf | inf |
| ATOM | 335 | O | H2O | 335 | 142.337 | −26.809 | 73.259 | inf | inf |
| ATOM | 336 | O | H2O | 336 | 150.742 | −26.848 | 73.025 | inf | inf |
| ATOM | 337 | O | H2O | 337 | 151.074 | −26.450 | 73.061 | inf | inf |
| ATOM | 338 | O | H2O | 338 | 151.404 | −26.061 | 73.092 | inf | inf |
| ATOM | 339 | O | H2O | 339 | 151.452 | −25.701 | 73.059 | inf | inf |
| ATOM | 340 | O | H2O | 340 | 151.507 | −25.368 | 73.295 | inf | inf |
| ATOM | 341 | O | H2O | 341 | 151.051 | −24.974 | 73.084 | inf | inf |
| ATOM | 342 | O | H2O | 342 | 142.913 | −24.761 | 73.277 | inf | inf |
| ATOM | 343 | O | H2O | 343 | 151.019 | −24.821 | 73.275 | inf | inf |
| ATOM | 344 | O | H2O | 344 | 143.838 | −24.201 | 73.278 | inf | inf |
| ATOM | 345 | O | H2O | 345 | 144.025 | −24.018 | 73.276 | inf | inf |
| ATOM | 346 | O | H2O | 346 | 150.577 | −23.486 | 73.276 | inf | inf |
| ATOM | 347 | O | H2O | 347 | 150.615 | −23.144 | 73.285 | inf | inf |
| ATOM | 348 | O | H2O | 348 | 150.557 | −22.367 | 73.271 | inf | inf |
| ATOM | 349 | O | H2O | 349 | 150.114 | −21.665 | 73.249 | inf | inf |
| ATOM | 350 | O | H2O | 350 | 144.393 | −21.278 | 73.063 | inf | inf |
| ATOM | 351 | O | H2O | 351 | 144.186 | −20.933 | 73.243 | inf | inf |
| ATOM | 352 | O | H2O | 352 | 148.455 | −21.162 | 73.234 | inf | inf |
| ATOM | 353 | O | H2O | 353 | 143.997 | −20.489 | 73.302 | inf | inf |
| ATOM | 354 | O | H2O | 354 | 147.700 | −20.766 | 73.287 | inf | inf |
| ATOM | 355 | O | H2O | 355 | 147.358 | −20.355 | 73.264 | inf | inf |
| ATOM | 356 | O | H2O | 356 | 147.111 | −19.822 | 73.284 | inf | inf |
| ATOM | 357 | O | H2O | 357 | 147.031 | −19.598 | 73.250 | inf | inf |
| ATOM | 358 | O | H2O | 358 | 144.017 | −18.857 | 73.243 | inf | inf |
| ATOM | 359 | O | H2O | 359 | 144.347 | −18.433 | 73.203 | inf | inf |
| ATOM | 360 | O | H2O | 360 | 146.418 | −18.342 | 73.276 | inf | inf |
| ATOM | 361 | O | H2O | 361 | 145.524 | −18.014 | 73.198 | inf | inf |
| ATOM | 362 | O | H2O | 362 | 143.104 | −29.065 | 73.593 | inf | inf |
| ATOM | 363 | O | H2O | 363 | 144.417 | −29.211 | 73.626 | inf | inf |
| ATOM | 364 | O | H2O | 364 | 145.333 | −29.010 | 73.634 | inf | inf |
| ATOM | 365 | O | H2O | 365 | 142.896 | −28.894 | 73.572 | inf | inf |
| ATOM | 366 | O | H2O | 366 | 142.329 | −28.332 | 73.570 | inf | inf |
| ATOM | 367 | O | H2O | 367 | 142.209 | −28.100 | 73.633 | inf | inf |
| ATOM | 368 | O | H2O | 368 | 142.135 | −27.587 | 73.705 | inf | inf |
| ATOM | 369 | O | H2O | 369 | 146.556 | −27.657 | 73.627 | inf | inf |
| ATOM | 370 | O | H2O | 370 | 149.585 | −27.526 | 73.452 | inf | inf |
| ATOM | 371 | O | H2O | 371 | 142.225 | −27.366 | 73.640 | inf | inf |
| ATOM | 372 | O | H2O | 372 | 147.329 | −27.239 | 73.631 | inf | inf |
| ATOM | 373 | O | H2O | 373 | 148.110 | −27.171 | 73.444 | inf | inf |
| ATOM | 374 | O | H2O | 374 | 150.381 | −27.477 | 73.599 | inf | inf |
| ATOM | 375 | O | H2O | 375 | 142.298 | −26.809 | 73.606 | inf | inf |
| ATOM | 376 | O | H2O | 376 | 151.190 | −26.771 | 73.646 | inf | inf |
| ATOM | 377 | O | H2O | 377 | 151.474 | −26.274 | 73.627 | inf | inf |
| ATOM | 378 | O | H2O | 378 | 142.560 | −25.327 | 73.448 | inf | inf |
| ATOM | 379 | O | H2O | 379 | 142.899 | −24.929 | 73.464 | inf | inf |
| ATOM | 380 | O | H2O | 380 | 151.445 | −25.138 | 73.627 | inf | inf |
| ATOM | 381 | O | H2O | 381 | 143.651 | −24.539 | 73.491 | inf | inf |
| ATOM | 382 | O | H2O | 382 | 144.023 | −24.206 | 73.468 | inf | inf |
| ATOM | 383 | O | H2O | 383 | 150.752 | −24.370 | 73.668 | inf | inf |
| ATOM | 384 | O | H2O | 384 | 144.417 | −23.671 | 73.628 | inf | inf |
| ATOM | 385 | O | H2O | 385 | 150.501 | −23.117 | 73.625 | inf | inf |
| ATOM | 386 | O | H2O | 386 | 150.448 | −22.399 | 73.607 | inf | inf |
| ATOM | 387 | O | H2O | 387 | 150.328 | −22.007 | 73.445 | inf | inf |
| ATOM | 388 | O | H2O | 388 | 149.971 | −21.620 | 73.455 | inf | inf |
| ATOM | 389 | O | H2O | 389 | 148.882 | −21.317 | 73.662 | inf | inf |
| ATOM | 390 | O | H2O | 390 | 149.581 | −21.467 | 73.620 | inf | inf |
| ATOM | 391 | O | H2O | 391 | 148.436 | −21.223 | 73.625 | inf | inf |
| ATOM | 392 | O | H2O | 392 | 147.726 | −20.728 | 73.627 | inf | inf |
| ATOM | 393 | O | H2O | 393 | 143.766 | −19.820 | 73.603 | inf | inf |
| ATOM | 394 | O | H2O | 394 | 147.031 | −19.417 | 73.430 | inf | inf |
| ATOM | 395 | O | H2O | 395 | 147.037 | −19.236 | 73.617 | inf | inf |
| ATOM | 396 | O | H2O | 396 | 144.068 | −18.517 | 73.634 | inf | inf |
| ATOM | 397 | O | H2O | 397 | 146.682 | −18.461 | 73.619 | inf | inf |
| ATOM | 398 | O | H2O | 398 | 144.965 | −17.912 | 73.617 | inf | inf |
| ATOM | 399 | O | H2O | 399 | 146.060 | −17.991 | 73.640 | inf | inf |
| ATOM | 400 | O | H2O | 400 | 146.632 | −33.227 | 74.059 | inf | inf |
| ATOM | 401 | O | H2O | 401 | 145.905 | −32.888 | 74.020 | inf | inf |
| ATOM | 402 | O | H2O | 402 | 146.279 | −32.707 | 73.869 | inf | inf |
| ATOM | 403 | O | H2O | 403 | 147.184 | −32.714 | 73.999 | inf | inf |
| ATOM | 404 | O | H2O | 404 | 146.632 | −32.346 | 73.829 | inf | inf |
| ATOM | 405 | O | H2O | 405 | 146.053 | −31.960 | 73.939 | inf | inf |
| ATOM | 406 | O | H2O | 406 | 147.180 | −31.981 | 74.010 | inf | inf |
| ATOM | 407 | O | H2O | 407 | 143.310 | −29.504 | 74.022 | inf | inf |
| ATOM | 408 | O | H2O | 408 | 143.679 | −29.392 | 73.812 | inf | inf |
| ATOM | 409 | O | H2O | 409 | 144.417 | −29.333 | 73.852 | inf | inf |
| ATOM | 410 | O | H2O | 410 | 145.100 | −29.337 | 73.867 | inf | inf |
| ATOM | 411 | O | H2O | 411 | 142.614 | −28.981 | 73.855 | inf | inf |
| ATOM | 412 | O | H2O | 412 | 145.487 | −29.185 | 74.026 | inf | inf |
| ATOM | 413 | O | H2O | 413 | 142.255 | −28.613 | 73.844 | inf | inf |
| ATOM | 414 | O | H2O | 414 | 145.933 | −28.503 | 73.976 | inf | inf |
| ATOM | 415 | O | H2O | 415 | 146.257 | −28.094 | 74.002 | inf | inf |
| ATOM | 416 | O | H2O | 416 | 146.799 | −27.521 | 74.005 | inf | inf |
| ATOM | 417 | O | H2O | 417 | 149.597 | −27.646 | 73.997 | inf | inf |
| ATOM | 418 | O | H2O | 418 | 150.489 | −27.502 | 73.997 | inf | inf |
| ATOM | 419 | O | H2O | 419 | 147.350 | −27.300 | 74.017 | inf | inf |
| ATOM | 420 | O | H2O | 420 | 147.920 | −27.149 | 73.996 | inf | inf |
| ATOM | 421 | O | H2O | 421 | 150.704 | −27.380 | 73.997 | inf | inf |
| ATOM | 422 | O | H2O | 422 | 148.107 | −27.138 | 73.998 | inf | inf |
| ATOM | 423 | O | H2O | 423 | 151.377 | −26.473 | 73.997 | inf | inf |
| ATOM | 424 | O | H2O | 424 | 142.586 | −25.709 | 73.804 | inf | inf |
| ATOM | 425 | O | H2O | 425 | 142.889 | −25.291 | 73.864 | inf | inf |
| ATOM | 426 | O | H2O | 426 | 143.287 | −24.929 | 73.835 | inf | inf |
| ATOM | 427 | O | H2O | 427 | 151.393 | −25.172 | 73.984 | inf | inf |
| ATOM | 428 | O | H2O | 428 | 151.028 | −24.829 | 73.979 | inf | inf |
| ATOM | 429 | O | H2O | 429 | 150.643 | −24.442 | 73.980 | inf | inf |
| ATOM | 430 | O | H2O | 430 | 150.377 | −23.898 | 73.952 | inf | inf |
| ATOM | 431 | O | H2O | 431 | 150.360 | −23.487 | 73.828 | inf | inf |
| ATOM | 432 | O | H2O | 432 | 144.583 | −22.748 | 73.997 | inf | inf |
| ATOM | 433 | O | H2O | 433 | 150.148 | −22.375 | 74.006 | inf | inf |
| ATOM | 434 | O | H2O | 434 | 150.009 | −22.167 | 74.042 | inf | inf |
| ATOM | 435 | O | H2O | 435 | 149.638 | −21.773 | 74.039 | inf | inf |
| ATOM | 436 | O | H2O | 436 | 148.639 | −21.306 | 73.985 | inf | inf |
| ATOM | 437 | O | H2O | 437 | 147.933 | −20.892 | 73 993 | inf | inf |
| ATOM | 438 | O | H2O | 438 | 144.104 | −20.681 | 73.977 | inf | inf |
| ATOM | 439 | O | H2O | 439 | 147.510 | −20.183 | 73.997 | inf | inf |
| ATOM | 440 | O | H2O | 440 | 143.701 | −19.426 | 73.997 | inf | inf |
| ATOM | 441 | O | H2O | 441 | 147.048 | −19.102 | 73.997 | inf | inf |
| ATOM | 442 | O | H2O | 442 | 144.040 | −18.498 | 73.997 | inf | inf |
| ATOM | 443 | O | H2O | 443 | 144.417 | −18.134 | 73.997 | inf | inf |
| ATOM | 444 | O | H2O | 444 | 146.313 | −18.058 | 73.973 | inf | inf |
| ATOM | 445 | O | H2O | 445 | 145.525 | −17.795 | 74.005 | inf | inf |
| ATOM | 446 | O | H2O | 446 | 145.950 | −33.378 | 74.276 | inf | inf |
| ATOM | 447 | O | H2O | 447 | 146.632 | −33.439 | 74.203 | inf | inf |
| ATOM | 448 | O | H2O | 448 | 145.564 | −33.239 | 74.415 | inf | inf |
| ATOM | 449 | O | H2O | 449 | 146.228 | −33.152 | 74.044 | inf | inf |
| ATOM | 450 | O | H2O | 450 | 147.550 | −33.080 | 74.370 | inf | inf |
| ATOM | 451 | O | H2O | 451 | 147.629 | −32.760 | 74.292 | inf | inf |
| ATOM | 452 | O | H2O | 452 | 147.657 | −32.346 | 74.263 | inf | inf |
| ATOM | 453 | O | H2O | 453 | 145.534 | −31.982 | 74.195 | inf | inf |
| ATOM | 454 | O | H2O | 454 | 147.742 | −32.161 | 74.363 | inf | inf |
| ATOM | 455 | O | H2O | 455 | 146.233 | −31.549 | 74.064 | inf | inf |
| ATOM | 456 | O | H2O | 456 | 147.537 | −31.618 | 74.380 | inf | inf |
| ATOM | 457 | O | H2O | 457 | 146.263 | −31.252 | 74.213 | inf | inf |
| ATOM | 458 | O | H2O | 458 | 147.360 | −31.433 | 74.376 | inf | inf |
| ATOM | 459 | O | H2O | 459 | 146.079 | −30.868 | 74.361 | inf | inf |
| ATOM | 460 | O | H2O | 460 | 145.894 | −30.688 | 74.389 | inf | inf |
| ATOM | 461 | O | H2O | 461 | 144.803 | −29.908 | 74.419 | inf | inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| | | | | | | | | |
|---|---|---|---|---|---|---|---|---|
| ATOM | 462 | O | H2O | 462 | 145.517 | −29.942 | 74.392 | inf inf |
| ATOM | 463 | O | H2O | 463 | 142.742 | −29.414 | 74.359 | inf inf |
| ATOM | 464 | O | H2O | 464 | 144.038 | −29.641 | 74.329 | inf inf |
| ATOM | 465 | O | H2O | 465 | 142.522 | −29.258 | 74.346 | inf inf |
| ATOM | 466 | O | H2O | 466 | 142.029 | −28.647 | 74.369 | inf inf |
| ATOM | 467 | O | H2O | 467 | 141.888 | −28.318 | 74.333 | inf inf |
| ATOM | 468 | O | H2O | 468 | 141.828 | −28.102 | 74.364 | inf inf |
| ATOM | 469 | O | H2O | 469 | 141.799 | −27.597 | 74.416 | inf inf |
| ATOM | 470 | O | H2O | 470 | 146.939 | −27.655 | 74.412 | inf inf |
| ATOM | 471 | O | H2O | 471 | 149.393 | −27.598 | 74.366 | inf inf |
| ATOM | 472 | O | H2O | 472 | 141.868 | −27.378 | 74.376 | inf inf |
| ATOM | 473 | O | H2O | 473 | 148.109 | −27.149 | 74.185 | inf inf |
| ATOM | 474 | O | H2O | 474 | 149.148 | −27.501 | 74.404 | inf inf |
| ATOM | 475 | O | H2O | 475 | 142.122 | −26.878 | 74.401 | inf inf |
| ATOM | 476 | O | H2O | 476 | 142.357 | −26.423 | 74.362 | inf inf |
| ATOM | 477 | O | H2O | 477 | 151.408 | −26.071 | 74.406 | inf inf |
| ATOM | 478 | O | H2O | 478 | 1S1.467 | −25.701 | 74.197 | inf inf |
| ATOM | 479 | O | H2O | 479 | 151.398 | −25.349 | 74.165 | inf inf |
| ATOM | 480 | O | H2O | 480 | 151.142 | −25.091 | 74.387 | inf inf |
| ATOM | 481 | O | H2O | 481 | 143.987 | −24.717 | 74.415 | inf inf |
| ATOM | 482 | O | H2O | 482 | 150.699 | −24.589 | 74.182 | inf inf |
| ATOM | 483 | O | H2O | 483 | 150.364 | −24.199 | 74.209 | inf inf |
| ATOM | 484 | O | H2O | 484 | 150.263 | −23.873 | 74.140 | inf inf |
| ATOM | 485 | O | H2O | 485 | 150.049 | −23.117 | 74.307 | inf inf |
| ATOM | 486 | O | H2O | 486 | 149.850 | −22.354 | 74.410 | inf inf |
| ATOM | 487 | O | H2O | 487 | 149.741 | −22.038 | 74.354 | inf inf |
| ATOM | 488 | O | H2O | 488 | 144.429 | −21.268 | 74.180 | inf inf |
| ATOM | 489 | O | H2O | 489 | 148.486 | −21.257 | 74.184 | inf inf |
| ATOM | 490 | O | H2O | 490 | 144.383 | −21.102 | 74.366 | inf inf |
| ATOM | 491 | O | H2O | 491 | 144.122 | −20.597 | 74.382 | inf inf |
| ATOM | 492 | O | H2O | 492 | 143.992 | −20.386 | 74.384 | inf inf |
| ATOM | 493 | O | H2O | 493 | 147.400 | −19.967 | 74.366 | inf inf |
| ATOM | 494 | O | H2O | 494 | 147.102 | −19.084 | 74.392 | inf inf |
| ATOM | 495 | O | H2O | 495 | 144.063 | −18.513 | 74.361 | inf inf |
| ATOM | 496 | O | H2O | 496 | 144.606 | −17.960 | 74.369 | inf inf |
| ATOM | 497 | O | H2O | 497 | 144.816 | −17.851 | 74.396 | inf inf |
| ATOM | 498 | O | H2O | 498 | 146.240 | −17.802 | 74.395 | inf inf |
| ATOM | 499 | O | H2O | 499 | 146.631 | −33.922 | 74.791 | inf inf |
| ATOM | 500 | O | H2O | 500 | 147.185 | −33.821 | 74.737 | inf inf |
| ATOM | 501 | O | H2O | 501 | 145.852 | −33.700 | 74.693 | inf inf |
| ATOM | 502 | O | H2O | 502 | 145.259 | −33.138 | 74.681 | inf inf |
| ATOM | 503 | O | H2O | 503 | 145.124 | −32.910 | 74.714 | inf inf |
| ATOM | 504 | O | H2O | 504 | 147.981 | −32.716 | 74.697 | inf inf |
| ATOM | 505 | O | H2O | 505 | 144.951 | −31.984 | 74.721 | inf inf |
| ATOM | 506 | O | H2O | 506 | 144.918 | −31.629 | 74.662 | inf inf |
| ATOM | 507 | O | H2O | 507 | 144.780 | −31.424 | 74.728 | inf inf |
| ATOM | 508 | O | H2O | 508 | 147.361 | −31.248 | 74.560 | inf inf |
| ATOM | 509 | O | H2O | 509 | 144.868 | −30.868 | 74.673 | inf inf |
| ATOM | 510 | O | H2O | 510 | 146.643 | −30.853 | 74.512 | inf inf |
| ATOM | 511 | O | H2O | 511 | 144.618 | −30.492 | 74.760 | inf inf |
| ATOM | 512 | O | H2O | 512 | 145.919 | −30.476 | 74.452 | inf inf |
| ATOM | 513 | O | H2O | 513 | 146.961 | −30.715 | 74.785 | inf inf |
| ATOM | 514 | O | H2O | 514 | 144.787 | −30.130 | 74.553 | inf inf |
| ATOM | 515 | O | H2O | 515 | 146.222 | −30.173 | 74.672 | inf inf |
| ATOM | 516 | O | H2O | 516 | 143.514 | −29.717 | 74.735 | inf inf |
| ATOM | 517 | O | H2O | 517 | 145.875 | −29.762 | 74.579 | inf inf |
| ATOM | 518 | O | H2O | 518 | 142.953 | −29.549 | 74.735 | inf inf |
| ATOM | 519 | O | H2O | 519 | 142.311 | −29.099 | 74.735 | inf inf |
| ATOM | 520 | O | H2O | 520 | 142.149 | −28.876 | 74.735 | inf inf |
| ATOM | 521 | O | H2O | 521 | 141.846 | −28.328 | 74.735 | inf inf |
| ATOM | 522 | O | H2O | 522 | 146.679 | −27.955 | 74.528 | inf inf |
| ATOM | 523 | O | H2O | 523 | 147.020 | −27.761 | 74.716 | inf inf |
| ATOM | 524 | O | H2O | 524 | 149.954 | −27.692 | 74.735 | inf inf |
| ATOM | 525 | O | H2O | 525 | 141.934 | −27.136 | 74.735 | inf inf |
| ATOM | 526 | O | H2O | 526 | 148.475 | −27.324 | 74.735 | inf inf |
| ATOM | 527 | O | H2O | 527 | 150.829 | −27.130 | 74.716 | inf inf |
| ATOM | 528 | O | H2O | 528 | 142.224 | −26.634 | 74.735 | inf inf |
| ATOM | 529 | O | H2O | 529 | 151.295 | −26.071 | 74.756 | inf inf |
| ATOM | 530 | O | H2O | 530 | 143.022 | −25.598 | 74.735 | inf inf |
| ATOM | 531 | O | H2O | 531 | 151.176 | −25.356 | 74.711 | inf inf |
| ATOM | 532 | O | H2O | 532 | 150.884 | −24.956 | 74.740 | inf inf |
| ATOM | 533 | O | H2O | 533 | 150.481 | −24.647 | 74.708 | inf inf |
| ATOM | 534 | O | H2O | 534 | 144.506 | −24.172 | 74.736 | inf inf |
| ATOM | 535 | O | H2O | 535 | 149.803 | −23.846 | 74.749 | inf inf |
| ATOM | 536 | O | H2O | 536 | 149.764 | −23.486 | 74.733 | inf inf |
| ATOM | 537 | O | H2O | 537 | 149.926 | −23.117 | 74.538 | inf inf |
| ATOM | 538 | O | H2O | 538 | 144.566 | −22.379 | 74.735 | inf inf |
| ATOM | 539 | O | H2O | 539 | 144.466 | −21.675 | 74.701 | inf inf |
| ATOM | 540 | O | H2O | 540 | 144.375 | −21.264 | 74.735 | inf inf |
| ATOM | 541 | O | H2O | 541 | 148.644 | −21.314 | 74.746 | inf inf |
| ATOM | 542 | O | H2O | 542 | 148.162 | −21.002 | 74.708 | inf inf |
| ATOM | 543 | O | H2O | 543 | 147.801 | −20.671 | 74.714 | inf inf |
| ATOM | 544 | O | H2O | 544 | 143.884 | −19.795 | 74.726 | inf inf |
| ATOM | 545 | O | H2O | 545 | 147.264 | −19.407 | 74.735 | inf inf |
| ATOM | 546 | O | H2O | 546 | 147.020 | −18.682 | 74.542 | inf inf |
| ATOM | 547 | O | H2O | 547 | 146.925 | −18.257 | 74.689 | inf inf |
| ATOM | 548 | O | H2O | 548 | 146.626 | −17.957 | 74.555 | inf inf |
| ATOM | 549 | O | H2O | 549 | 144.985 | −17.608 | 74.749 | inf inf |
| ATOM | 550 | O | H2O | 550 | 146.094 | −17.544 | 74.714 | inf inf |
| ATOM | 551 | O | H2O | 551 | 145.870 | −17.469 | 74.759 | inf inf |
| ATOM | 552 | O | H2O | 552 | 147.370 | −34.334 | 75.146 | inf inf |
| ATOM | 553 | O | H2O | 553 | 145.716 | −33.812 | 75.107 | inf inf |
| ATOM | 554 | O | H2O | 554 | 147.399 | −33.881 | 74.831 | inf inf |
| ATOM | 555 | O | H2O | 555 | 148.040 | −33.789 | 75.022 | inf inf |
| ATOM | 556 | O | H2O | 556 | 147.806 | −33.504 | 74.803 | inf inf |
| ATOM | 557 | O | H2O | 557 | 145.017 | −33.068 | 75.119 | inf inf |
| ATOM | 558 | O | H2O | 558 | 144.915 | −32.729 | 75.090 | inf inf |
| ATOM | 559 | O | H2O | 559 | 148.122 | −32.346 | 74.911 | inf inf |
| ATOM | 560 | O | H2O | 560 | 144.785 | −31.977 | 74.919 | inf inf |
| ATOM | 561 | O | H2O | 561 | 144.709 | −31.633 | 74.842 | inf inf |
| ATOM | 562 | O | H2O | 562 | 147.630 | −31.163 | 75.079 | inf inf |
| ATOM | 563 | O | H2O | 563 | 144.478 | −30.848 | 74.960 | inf inf |
| ATOM | 564 | O | H2O | 564 | 144.415 | −30.501 | 74.916 | inf inf |
| ATOM | 565 | O | H2O | 565 | 144.093 | −30.287 | 75.119 | inf inf |
| ATOM | 566 | O | H2O | 566 | 146.818 | −30.130 | 75.103 | inf inf |
| ATOM | 567 | O | H2O | 567 | 146.272 | −29.759 | 74.910 | inf inf |
| ATOM | 568 | O | H2O | 568 | 142.960 | −29.518 | 75.103 | inf inf |
| ATOM | 569 | O | H2O | 569 | 142.310 | −29.100 | 75.105 | inf inf |
| ATOM | 570 | O | H2O | 570 | 142.004 | −28.660 | 75.104 | inf inf |
| ATOM | 571 | O | H2O | 571 | 146.664 | −28.310 | 74.901 | inf inf |
| ATOM | 572 | O | H2O | 572 | 141.822 | −28.102 | 75.104 | inf inf |
| ATOM | 573 | O | H2O | 573 | 141.816 | −27.549 | 75.102 | inf inf |
| ATOM | 574 | O | H2O | 574 | 149.400 | −27.548 | 75.104 | inf inf |
| ATOM | 575 | O | H2O | 575 | 150.158 | −27.593 | 75.117 | inf inf |
| ATOM | 576 | O | H2O | 576 | 148.118 | −27.407 | 75.105 | inf inf |
| ATOM | 577 | O | H2O | 577 | 150.390 | −27.463 | 75.138 | inf inf |
| ATOM | 578 | O | H2O | 578 | 1S0.738 | −27.013 | 75.131 | inf inf |
| ATOM | 579 | O | H2O | 579 | 142.365 | −26.431 | 75.110 | inf inf |
| ATOM | 580 | O | H2O | 580 | 142.493 | −26.199 | 75.126 | inf inf |
| ATOM | 581 | O | H2O | 581 | 142.936 | −25.693 | 74.921 | inf inf |
| ATOM | 582 | O | H2O | 582 | 151.072 | −25.884 | 75.113 | inf inf |
| ATOM | 583 | O | H2O | 583 | 143.613 | −25.401 | 75.153 | inf inf |
| ATOM | 584 | O | H2O | 584 | 144.049 | −24.964 | 74.919 | inf inf |
| ATOM | 585 | O | H2O | 585 | 150.713 | −25.122 | 75.129 | inf inf |
| ATOM | 586 | O | H2O | 586 | 150.310 | −24.801 | 75.086 | inf inf |
| ATOM | 587 | O | H2O | 587 | 149.795 | −24.215 | 75.122 | inf inf |
| ATOM | 588 | O | H2O | 588 | 149.704 | −23.873 | 75.086 | inf inf |
| ATOM | 589 | O | H2O | 589 | 149.724 | −23.104 | 75.098 | inf inf |
| ATOM | 590 | O | H2O | 590 | 149.695 | −22.390 | 75.104 | inf inf |
| ATOM | 591 | O | H2O | 591 | 144.395 | −21.639 | 75.104 | inf inf |
| ATOM | 592 | O | H2O | 592 | 144.381 | −21.272 | 75.104 | inf inf |
| ATOM | 593 | O | H2O | 593 | 144.325 | −20.875 | 75.104 | inf inf |
| ATOM | 594 | O | H2O | 594 | 148.815 | −21.186 | 75.170 | inf inf |
| ATOM | 595 | O | H2O | 595 | 148.056 | −20.769 | 75.125 | inf inf |
| ATOM | 596 | O | H2O | 596 | 147.678 | −20.390 | 75.125 | inf inf |
| ATOM | 597 | O | H2O | 597 | 147.404 | −19.965 | 75.104 | inf inf |
| ATOM | 598 | O | H2O | 598 | 144.005 | −19.056 | 75.085 | inf inf |
| ATOM | 599 | O | H2O | 599 | 144.069 | −18.647 | 75.104 | inf inf |
| ATOM | 600 | O | H2O | 600 | 147.102 | −18.347 | 75.105 | inf inf |
| ATOM | 601 | O | H2O | 601 | 146.996 | −18.137 | 75.104 | inf inf |
| ATOM | 602 | O | H2O | 602 | 146.281 | −17.548 | 74.905 | inf inf |
| ATOM | 603 | O | H2O | 603 | 145.524 | −17.371 | 75.098 | inf inf |
| ATOM | 604 | O | H2O | 604 | 146.818 | −34.566 | 75.477 | inf inf |
| ATOM | 605 | O | H2O | 605 | 147.558 | −34.572 | 75.466 | inf inf |
| ATOM | 606 | O | H2O | 606 | 146.609 | −34.445 | 75.427 | inf inf |
| ATOM | 607 | O | H2O | 607 | 148.090 | −34.346 | 75.497 | inf inf |
| ATOM | 608 | O | H2O | 608 | 145.900 | −33.998 | 75.476 | inf inf |
| ATOM | 609 | O | H2O | 609 | 145.269 | −33.524 | 75.473 | inf inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| | | | | | | | | |
|---|---|---|---|---|---|---|---|---|
| ATOM | 610 | O | H2O | 610 | 144.975 | −33.082 | 75.473 | inf inf |
| ATOM | 611 | O | H2O | 611 | 144.848 | −32.746 | 75.442 | inf inf |
| ATOM | 612 | O | H2O | 612 | 144.643 | −32.317 | 75.487 | inf inf |
| ATOM | 613 | O | H2O | 613 | 144.495 | −32.038 | 75.427 | inf inf |
| ATOM | 614 | O | H2O | 614 | 144.393 | −31.614 | 75.278 | inf inf |
| ATOM | 615 | O | H2O | 615 | 144.358 | −31.238 | 75.263 | inf inf |
| ATOM | 616 | O | H2O | 616 | 147.519 | −30.893 | 75.485 | inf inf |
| ATOM | 617 | O | H2O | 617 | 147.394 | −30.674 | 75.466 | inf inf |
| ATOM | 618 | O | H2O | 618 | 147.112 | −30.179 | 75.497 | inf inf |
| ATOM | 619 | O | H2O | 619 | 146.848 | −29.751 | 75.452 | inf inf |
| ATOM | 620 | O | H2O | 620 | 143.269 | −29.654 | 75.474 | inf inf |
| ATOM | 621 | O | H2O | 621 | 142.126 | −28.951 | 75.473 | inf inf |
| ATOM | 622 | O | H2O | 622 | 146.785 | −29.022 | 75.504 | inf inf |
| ATOM | 623 | O | H2O | 623 | 141.848 | −28.328 | 75.473 | inf inf |
| ATOM | 624 | O | H2O | 624 | 141.817 | −27.917 | 75.474 | inf inf |
| ATOM | 625 | O | H2O | 625 | 141.838 | −27.732 | 75.473 | inf inf |
| ATOM | 626 | O | H2O | 626 | 147.681 | −27.640 | 75.504 | inf inf |
| ATOM | 627 | O | H2O | 627 | 142.037 | −27.191 | 75.473 | inf inf |
| ATOM | 628 | O | H2O | 628 | 149.223 | −27.409 | 75.500 | inf inf |
| ATOM | 629 | O | H2O | 629 | 150.467 | −27.153 | 75.440 | inf inf |
| ATOM | 630 | O | H2O | 630 | 150.709 | −26.814 | 75.300 | inf inf |
| ATOM | 631 | O | H2O | 631 | 150.755 | −26.460 | 75.350 | inf inf |
| ATOM | 632 | O | H2O | 632 | 150.774 | −26.070 | 75.404 | inf inf |
| ATOM | 633 | O | H2O | 633 | 150.529 | −25.687 | 75.523 | inf inf |
| ATOM | 634 | O | H2O | 634 | 143.895 | −25.381 | 75.457 | inf inf |
| ATOM | 635 | O | H2O | 635 | 144.281 | −24.995 | 75.457 | inf inf |
| ATOM | 636 | O | H2O | 636 | 150.304 | −25.186 | 75.416 | inf inf |
| ATOM | 637 | O | H2O | 637 | 144.572 | −24.581 | 75.482 | inf inf |
| ATOM | 638 | O | H2O | 638 | 149.655 | −24.267 | 75.432 | inf inf |
| ATOM | 639 | O | H2O | 639 | 149.624 | −23.854 | 75.306 | inf inf |
| ATOM | 640 | O | H2O | 640 | 144.748 | −23.121 | 75.471 | inf inf |
| ATOM | 641 | O | H2O | 641 | 144.627 | −22.368 | 75.472 | inf inf |
| ATOM | 642 | O | H2O | 642 | 144.408 | −21.643 | 75.290 | inf inf |
| ATOM | 643 | O | H2O | 643 | 144.410 | −21.271 | 75.448 | inf inf |
| ATOM | 644 | O | H2O | 644 | 144.365 | −20.899 | 75.428 | inf inf |
| ATOM | 645 | O | H2O | 645 | 144.304 | −20.510 | 75.449 | inf inf |
| ATOM | 646 | O | H2O | 646 | 147.562 | −20.160 | 75.471 | inf inf |
| ATOM | 647 | O | H2O | 647 | 147.421 | −19.839 | 75.516 | inf inf |
| ATOM | 648 | O | H2O | 648 | 147.357 | −19.612 | 75.477 | inf inf |
| ATOM | 649 | O | H2O | 649 | 144.035 | −18.870 | 75.473 | inf inf |
| ATOM | 650 | O | H2O | 650 | 147.106 | −18.345 | 75.473 | inf inf |
| ATOM | 651 | O | H2O | 651 | 144.492 | −17.840 | 75.473 | inf inf |
| ATOM | 652 | O | H2O | 652 | 146.662 | −17.735 | 75.473 | inf inf |
| ATOM | 653 | O | H2O | 653 | 146.234 | −17.479 | 75.473 | inf inf |
| ATOM | 654 | O | H2O | 654 | 146.992 | −34.777 | 75.829 | inf inf |
| ATOM | 655 | O | H2O | 655 | 147.949 | −34.619 | 75.826 | inf inf |
| ATOM | 656 | O | H2O | 656 | 148.430 | −34.154 | 75.686 | inf inf |
| ATOM | 657 | O | H2O | 657 | 145.844 | −34.055 | 75.825 | inf inf |
| ATOM | 658 | O | H2O | 658 | 148.787 | −33.485 | 75.779 | inf inf |
| ATOM | 659 | O | H2O | 659 | 144.868 | −32.773 | 75.857 | inf inf |
| ATOM | 660 | O | H2O | 660 | 148.497 | −32.331 | 75.646 | inf inf |
| ATOM | 661 | O | H2O | 661 | 144.392 | −31.991 | 75.654 | inf inf |
| ATOM | 662 | O | H2O | 662 | 147.996 | −31.560 | 75.843 | inf inf |
| ATOM | 663 | O | H2O | 663 | 144.148 | −30.891 | 75.842 | inf inf |
| ATOM | 664 | O | H2O | 664 | 143.945 | −30.444 | 75.842 | inf inf |
| ATOM | 665 | O | H2O | 665 | 143.776 | −30.184 | 75.817 | inf inf |
| ATOM | 666 | O | H2O | 666 | 143.630 | −29.990 | 75.826 | inf inf |
| ATOM | 667 | O | H2O | 667 | 142.958 | −29.536 | 75.842 | inf inf |
| ATOM | 668 | O | H2O | 668 | 142.129 | −28.950 | 75.843 | inf inf |
| ATOM | 669 | O | H2O | 669 | 141.970 | −28.675 | 75.856 | inf inf |
| ATOM | 670 | O | H2O | 670 | 147.153 | −28.263 | 75.853 | inf inf |
| ATOM | 671 | O | H2O | 671 | 147.325 | −28.056 | 75.861 | inf inf |
| ATOM | 672 | O | H2O | 672 | 147.712 | −27.691 | 75.856 | inf inf |
| ATOM | 673 | O | H2O | 673 | 148.476 | −27.460 | 75.818 | inf inf |
| ATOM | 674 | O | H2O | 674 | 149.961 | −27.191 | 75.678 | inf inf |
| ATOM | 675 | O | H2O | 675 | 142.372 | −26.794 | 75.848 | inf inf |
| ATOM | 676 | O | H2O | 676 | 142.584 | −26.450 | 75.650 | inf inf |
| ATOM | 677 | O | H2O | 677 | 1S0.311 | −26.440 | 75.639 | inf inf |
| ATOM | 678 | O | H2O | 678 | 150.090 | −26.071 | 75.769 | inf inf |
| ATOM | 679 | O | H2O | 679 | 143.513 | −25.730 | 75.833 | inf inf |
| ATOM | 680 | O | H2O | 680 | 150.312 | −25.707 | 75.618 | inf inf |
| ATOM | 681 | O | H2O | 681 | 144.146 | −25.246 | 75.842 | inf inf |
| ATOM | 682 | O | H2O | 682 | 144.326 | −25.024 | 75.842 | inf inf |
| ATOM | 683 | O | H2O | 683 | 144.491 | −24.830 | 75.841 | inf inf |
| ATOM | 684 | O | H2O | 684 | 144.722 | −24.243 | 75.841 | inf inf |
| ATOM | 685 | O | H2O | 685 | 149.443 | −23.868 | 75.861 | inf inf |
| ATOM | 686 | O | H2O | 686 | 144.697 | −23.119 | 75.869 | inf inf |
| ATOM | 687 | O | H2O | 687 | 149.811 | −22.759 | 75.842 | inf inf |
| ATOM | 688 | O | H2O | 688 | 149.741 | −22.018 | 75.846 | inf inf |
| ATOM | 689 | O | H2O | 689 | 149.513 | −21.561 | 75.842 | inf inf |
| ATOM | 690 | O | H2O | 690 | 149.330 | −21.342 | 75.842 | inf inf |
| ATOM | 691 | O | H2O | 691 | 148.497 | −20.868 | 75.653 | inf inf |
| ATOM | 692 | O | H2O | 692 | 144.367 | −20.488 | 75.838 | inf inf |
| ATOM | 693 | O | H2O | 693 | 148.425 | −20.796 | 75.842 | inf inf |
| ATOM | 694 | O | H2O | 694 | 144.320 | −19.765 | 75.813 | inf inf |
| ATOM | 695 | O | H2O | 695 | 147.417 | −19.590 | 75.829 | inf inf |
| ATOM | 696 | O | H2O | 696 | 144.156 | −18.666 | 75.875 | inf inf |
| ATOM | 697 | O | H2O | 697 | 144.426 | −17.957 | 75.656 | inf inf |
| ATOM | 698 | O | H2O | 698 | 146.936 | −18.177 | 75.821 | inf inf |
| ATOM | 699 | O | H2O | 699 | 146.605 | −17.792 | 75.832 | inf inf |
| ATOM | 700 | O | H2O | 700 | 146.213 | −17.543 | 75.793 | inf inf |
| ATOM | 701 | O | H2O | 701 | 146.623 | −34.767 | 76.211 | inf inf |
| ATOM | 702 | O | H2O | 702 | 148.122 | −34.581 | 76.020 | inf inf |
| ATOM | 703 | O | H2O | 703 | 145.815 | −34.121 | 76.211 | inf inf |
| ATOM | 704 | O | H2O | 704 | 145.659 | −33.855 | 76.211 | inf inf |
| ATOM | 705 | O | H2O | 705 | 148.870 | −33.460 | 76.023 | inf inf |
| ATOM | 706 | O | H2O | 706 | 145.207 | −33.235 | 76.194 | inf inf |
| ATOM | 707 | O | H2O | 707 | 148.825 | −32.721 | 76.030 | inf inf |
| ATOM | 708 | O | H2O | 708 | 148.691 | −32.327 | 76.211 | inf inf |
| ATOM | 709 | O | H2O | 709 | 148.344 | −31.915 | 76.201 | inf inf |
| ATOM | 710 | O | H2O | 710 | 148.157 | −31.744 | 76.212 | inf inf |
| ATOM | 711 | O | H2O | 711 | 147.595 | −30.852 | 76.200 | inf inf |
| ATOM | 712 | O | H2O | 712 | 147.486 | −30.524 | 76.233 | inf inf |
| ATOM | 713 | O | H2O | 713 | 147.243 | −30.093 | 76.189 | inf inf |
| ATOM | 714 | O | H2O | 714 | 143.305 | −29.767 | 76.026 | inf inf |
| ATOM | 715 | O | H2O | 715 | 146.980 | −29.393 | 76.031 | inf inf |
| ATOM | 716 | O | H2O | 716 | 142.388 | −29.022 | 76.210 | inf inf |
| ATOM | 717 | O | H2O | 717 | 142.182 | −28.852 | 76.218 | inf inf |
| ATOM | 718 | O | H2O | 718 | 147.259 | −28.334 | 76.162 | inf inf |
| ATOM | 719 | O | H2O | 719 | 147.597 | −27.958 | 76.177 | inf inf |
| ATOM | 720 | O | H2O | 720 | 148.097 | −27.696 | 76.236 | inf inf |
| ATOM | 721 | O | H2O | 721 | 148.836 | −27.339 | 76.212 | inf inf |
| ATOM | 722 | O | H2O | 722 | 142.252 | −27.043 | 76.192 | inf inf |
| ATOM | 723 | O | H2O | 723 | 149.900 | −26.768 | 75.960 | inf inf |
| ATOM | 724 | O | H2O | 724 | 143.063 | −26.364 | 76.249 | inf inf |
| ATOM | 725 | O | H2O | 725 | 143.278 | −26.032 | 76.046 | inf inf |
| ATOM | 726 | O | H2O | 726 | 149.874 | −26.071 | 75.948 | inf inf |
| ATOM | 727 | O | H2O | 727 | 149.486 | −25.674 | 76.261 | inf inf |
| ATOM | 728 | O | H2O | 728 | 144.192 | −25.304 | 76.225 | inf inf |
| ATOM | 729 | O | H2O | 729 | 149.320 | −24.989 | 76.152 | inf inf |
| ATOM | 730 | O | H2O | 730 | 144.672 | −24.235 | 76.231 | inf inf |
| ATOM | 731 | O | H2O | 731 | 144.647 | −23.480 | 76.225 | inf inf |
| ATOM | 732 | O | H2O | 732 | 149.710 | −23.100 | 76.203 | inf inf |
| ATOM | 733 | O | H2O | 733 | 149.803 | −22.379 | 76.220 | inf inf |
| ATOM | 734 | O | H2O | 734 | 149.725 | −22.023 | 76.205 | inf inf |
| ATOM | 735 | O | H2O | 735 | 144.340 | −21.302 | 76.241 | inf inf |
| ATOM | 736 | O | H2O | 736 | 148.651 | −20.928 | 76.211 | inf inf |
| ATOM | 737 | O | H2O | 737 | 148.114 | −20.525 | 76.023 | inf inf |
| ATOM | 738 | O | H2O | 738 | 144.448 | −20.352 | 76.211 | inf inf |
| ATOM | 739 | O | H2O | 739 | 148.028 | −20.401 | 76.212 | inf inf |
| ATOM | 740 | O | H2O | 740 | 147.745 | −19.977 | 76.210 | inf inf |
| ATOM | 741 | O | H2O | 741 | 147.478 | −19.503 | 76.211 | inf inf |
| ATOM | 742 | O | H2O | 742 | 144.293 | −18.708 | 76.171 | inf inf |
| ATOM | 743 | O | H2O | 743 | 144.374 | −18.290 | 76.056 | inf inf |
| ATOM | 744 | O | H2O | 744 | 146.945 | −18.347 | 75.999 | inf inf |
| ATOM | 745 | O | H2O | 745 | 146.641 | −17.938 | 76.034 | inf inf |
| ATOM | 746 | O | H2O | 746 | 145.525 | −17.677 | 76.274 | inf inf |
| ATOM | 747 | O | H2O | 747 | 146.255 | −17.777 | 76.201 | inf inf |
| ATOM | 748 | O | H2O | 748 | 146.623 | −34.767 | 76.581 | inf inf |
| ATOM | 749 | O | H2O | 749 | 148.054 | −34.664 | 76.581 | inf inf |
| ATOM | 750 | O | H2O | 750 | 148.453 | −34.352 | 76.580 | inf inf |
| ATOM | 751 | O | H2O | 751 | 145.414 | −33.406 | 76.555 | inf inf |
| ATOM | 752 | O | H2O | 752 | 145.148 | −33.088 | 76.397 | inf inf |
| ATOM | 753 | O | H2O | 753 | 145.079 | −32.953 | 76.581 | inf inf |
| ATOM | 754 | O | H2O | 754 | 148.690 | −32.327 | 76.581 | inf inf |
| ATOM | 755 | O | H2O | 755 | 148.383 | −31.887 | 76.549 | inf inf |
| ATOM | 756 | O | H2O | 756 | 148.034 | −31.532 | 76.548 | inf inf |
| ATOM | 757 | O | H2O | 757 | 144.168 | −30.897 | 76.599 | inf inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| | | | | | | | | |
|---|---|---|---|---|---|---|---|---|
| ATOM | 758 | O | H2O | 758 | 144.049 | −30.684 | 76.580 | inf inf |
| ATOM | 759 | O | H2O | 759 | 143.736 | −30.259 | 76.581 | inf inf |
| ATOM | 760 | O | H2O | 760 | 143.396 | −29.833 | 76.580 | inf inf |
| ATOM | 761 | O | H2O | 761 | 143.023 | −29.443 | 76.611 | inf inf |
| ATOM | 762 | O | H2O | 762 | 142.727 | −29.055 | 76.593 | inf inf |
| ATOM | 763 | O | H2O | 763 | 142.348 | −28.686 | 76.620 | inf inf |
| ATOM | 764 | O | H2O | 764 | 142.222 | −28.465 | 76.553 | inf inf |
| ATOM | 765 | O | H2O | 765 | 142.089 | −27.916 | 76.533 | inf inf |
| ATOM | 766 | O | H2O | 766 | 142.120 | −27.524 | 76.455 | inf inf |
| ATOM | 767 | O | H2O | 767 | 148.489 | −27.567 | 76.393 | inf inf |
| ATOM | 768 | O | H2O | 768 | 142.397 | −27.188 | 76.570 | inf inf |
| ATOM | 769 | O | H2O | 769 | 142.597 | −26.841 | 76.377 | inf inf |
| ATOM | 770 | O | H2O | 770 | 149.369 | −26.777 | 76.568 | inf inf |
| ATOM | 771 | O | H2O | 771 | 149.440 | −26.451 | 76.598 | inf inf |
| ATOM | 772 | O | H2O | 772 | 149.554 | −26.086 | 76.381 | inf inf |
| ATOM | 773 | O | H2O | 773 | 144.090 | −25.559 | 76.564 | inf inf |
| ATOM | 774 | O | H2O | 774 | 144.383 | −25.134 | 76.590 | inf inf |
| ATOM | 775 | O | H2O | 775 | 149.180 | −24.973 | 76.379 | inf inf |
| ATOM | 776 | O | H2O | 776 | 144.553 | −24.225 | 76.581 | inf inf |
| ATOM | 777 | O | H2O | 777 | 149.187 | −24.036 | 76.572 | inf inf |
| ATOM | 778 | O | H2O | 778 | 144.436 | −23.296 | 76.593 | inf inf |
| ATOM | 779 | O | H2O | 779 | 149.632 | −23.071 | 76.534 | inf inf |
| ATOM | 780 | O | H2O | 780 | 144.180 | −22.411 | 76.518 | inf inf |
| ATOM | 781 | O | H2O | 781 | 143.935 | −22.010 | 76.652 | inf inf |
| ATOM | 782 | O | H2O | 782 | 144.132 | −21.640 | 76.451 | inf inf |
| ATOM | 783 | O | H2O | 783 | 144.211 | −21.266 | 76.568 | inf inf |
| ATOM | 784 | O | H2O | 784 | 144.246 | −20.902 | 76.588 | inf inf |
| ATOM | 785 | O | H2O | 785 | 148.035 | −20.455 | 76.585 | inf inf |
| ATOM | 786 | O | H2O | 786 | 144.447 | −20.164 | 76.400 | inf inf |
| ATOM | 787 | O | H2O | 787 | 144.455 | −19.789 | 76.575 | inf inf |
| ATOM | 788 | O | H2O | 788 | 144.498 | −19.380 | 76.639 | inf inf |
| ATOM | 789 | O | H2O | 789 | 147.127 | −19.114 | 76.557 | inf inf |
| ATOM | 790 | O | H2O | 790 | 146.773 | −18.731 | 76.537 | inf inf |
| ATOM | 791 | O | H2O | 791 | 144.956 | −18.299 | 76.615 | inf inf |
| ATOM | 792 | O | H2O | 792 | 144.842 | −18.005 | 76.340 | inf inf |
| ATOM | 793 | O | H2O | 793 | 145.525 | −17.862 | 76.483 | inf inf |
| ATOM | 794 | O | H2O | 794 | 146.263 | −17.949 | 76.396 | inf inf |
| ATOM | 795 | O | H2O | 795 | 146.992 | −34.775 | 76.962 | inf inf |
| ATOM | 796 | O | H2O | 796 | 147.948 | −34.617 | 76.966 | inf inf |
| ATOM | 797 | O | H2O | 797 | 148.172 | −34.471 | 76.982 | inf inf |
| ATOM | 798 | O | H2O | 798 | 145.862 | −34.028 | 76.960 | inf inf |
| ATOM | 799 | O | H2O | 799 | 148.818 | −33.634 | 76.949 | inf inf |
| ATOM | 800 | O | H2O | 800 | 144.899 | −32.766 | 76.950 | inf inf |
| ATOM | 801 | O | H2O | 801 | 144.756 | −32.543 | 76.950 | inf inf |
| ATOM | 802 | O | H2O | 802 | 148.483 | −31.972 | 76.764 | inf inf |
| ATOM | 803 | O | H2O | 803 | 148.146 | −31.577 | 76.745 | inf inf |
| ATOM | 804 | O | H2O | 804 | 148.013 | −31.204 | 76.896 | inf inf |
| ATOM | 805 | O | H2O | 805 | 143.937 | −30.451 | 76.950 | inf inf |
| ATOM | 806 | O | H2O | 806 | 143.595 | −30.064 | 76.950 | inf inf |
| ATOM | 807 | O | H2O | 807 | 143.414 | −29.843 | 76.949 | inf inf |
| ATOM | 808 | O | H2O | 808 | 143.066 | −29.422 | 76.951 | inf inf |
| ATOM | 809 | O | H2O | 809 | 142.766 | −29.017 | 76.946 | inf inf |
| ATOM | 810 | O | H2O | 810 | 142.511 | −28.654 | 76.813 | inf inf |
| ATOM | 811 | O | H2O | 811 | 142.289 | −28.246 | 76.666 | inf inf |
| ATOM | 812 | O | H2O | 812 | 147.796 | −28.495 | 76.933 | inf inf |
| ATOM | 813 | O | H2O | 813 | 148.135 | −27.948 | 76.749 | inf inf |
| ATOM | 814 | O | H2O | 814 | 142.551 | −27.735 | 76.967 | inf inf |
| ATOM | 815 | O | H2O | 815 | 142.588 | −27.190 | 76.744 | inf inf |
| ATOM | 816 | O | H2O | 816 | 142.974 | −26.850 | 76.740 | inf inf |
| ATOM | 817 | O | H2O | 817 | 149.258 | −26.769 | 76.927 | inf inf |
| ATOM | 818 | O | H2O | 818 | 149.350 | −26.425 | 76.942 | inf inf |
| ATOM | 819 | O | H2O | 819 | 143.912 | −25.774 | 76.950 | inf inf |
| ATOM | 820 | O | H2O | 820 | 149.159 | −25.268 | 76.950 | inf inf |
| ATOM | 821 | O | H2O | 821 | 144.495 | −24.937 | 76.949 | inf inf |
| ATOM | 822 | O | H2O | 822 | 144.511 | −24.224 | 76.927 | inf inf |
| ATOM | 823 | O | H2O | 823 | 149.125 | −23.880 | 76.977 | inf inf |
| ATOM | 824 | O | H2O | 824 | 149.208 | −23.668 | 76.947 | inf inf |
| ATOM | 825 | O | H2O | 825 | 149.409 | −23.120 | 76.953 | inf inf |
| ATOM | 826 | O | H2O | 826 | 149.465 | −22.749 | 76.993 | inf inf |
| ATOM | 827 | O | H2O | 827 | 149.468 | −22.379 | 76.995 | inf inf |
| ATOM | 828 | O | H2O | 828 | 143.746 | −22.010 | 76.832 | inf inf |
| ATOM | 829 | O | H2O | 829 | 143.784 | −21.615 | 76.871 | inf inf |
| ATOM | 830 | O | H2O | 830 | 149.018 | −21.285 | 76.949 | inf inf |
| ATOM | 831 | O | H2O | 831 | 148.659 | −20.910 | 76.952 | inf inf |
| ATOM | 832 | O | H2O | 832 | 148.105 | −20.536 | 76.766 | inf inf |
| ATOM | 833 | O | H2O | 833 | 147.919 | −20.166 | 76.951 | inf inf |
| ATOM | 834 | O | H2O | 834 | 147.639 | −19.735 | 76.949 | inf inf |
| ATOM | 835 | O | H2O | 835 | 147.450 | −19.497 | 76.982 | inf inf |
| ATOM | 836 | O | H2O | 836 | 144.898 | −19.008 | 76.998 | inf inf |
| ATOM | 837 | O | H2O | 837 | 144.832 | −18.706 | 76.719 | inf inf |
| ATOM | 838 | O | H2O | 838 | 146.438 | −18.704 | 76.938 | inf inf |
| ATOM | 839 | O | H2O | 839 | 145.525 | −18.298 | 76.793 | inf inf |
| ATOM | 840 | O | H2O | 840 | 146.228 | −18.561 | 76.903 | inf inf |
| ATOM | 841 | O | H2O | 841 | 146.812 | −34.588 | 77.327 | inf inf |
| ATOM | 842 | O | H2O | 842 | 146.108 | −34.161 | 77.307 | inf inf |
| ATOM | 843 | O | H2O | 843 | 148.454 | −34.172 | 77.131 | inf inf |
| ATOM | 844 | O | H2O | 844 | 148.536 | −34.049 | 77.317 | inf inf |
| ATOM | 845 | O | H2O | 845 | 148.792 | −33.615 | 77.318 | inf inf |
| ATOM | 846 | O | H2O | 846 | 148.941 | −33.083 | 77.348 | inf inf |
| ATOM | 847 | O | H2O | 847 | 144.635 | −32.323 | 77.319 | inf inf |
| ATOM | 848 | O | H2O | 848 | 144.518 | −32.012 | 77.296 | inf inf |
| ATOM | 849 | O | H2O | 849 | 144.401 | −31.803 | 77.314 | inf inf |
| ATOM | 850 | O | H2O | 850 | 148.131 | −31.232 | 77.124 | inf inf |
| ATOM | 851 | O | H2O | 851 | 148.136 | −30.877 | 77.372 | inf inf |
| ATOM | 852 | O | H2O | 852 | 148.155 | −30.500 | 77.365 | inf inf |
| ATOM | 853 | O | H2O | 853 | 148.121 | −30.314 | 77.312 | inf inf |
| ATOM | 854 | O | H2O | 854 | 147.792 | −29.736 | 77.090 | inf inf |
| ATOM | 855 | O | H2O | 855 | 147.791 | −29.427 | 77.362 | inf inf |
| ATOM | 856 | O | H2O | 856 | 147.740 | −29.208 | 77.319 | inf inf |
| ATOM | 857 | O | H2O | 857 | 147.829 | −28.619 | 77.350 | inf inf |
| ATOM | 858 | O | H2O | 858 | 142.653 | −27.916 | 77.079 | inf inf |
| ATOM | 859 | O | H2O | 859 | 142.874 | −27.514 | 77.192 | inf inf |
| ATOM | 860 | O | H2O | 860 | 148.676 | −27.561 | 77.319 | inf inf |
| ATOM | 861 | O | H2O | 861 | 149.025 | −27.174 | 77.319 | inf inf |
| ATOM | 862 | O | H2O | 862 | 143.372 | −26.652 | 77.299 | inf inf |
| ATOM | 863 | O | H2O | 863 | 143.592 | −26.217 | 77.322 | inf inf |
| ATOM | 864 | O | H2O | 864 | 143.956 | −25.794 | 77.319 | inf inf |
| ATOM | 865 | O | H2O | 865 | 149.164 | −25.266 | 77.318 | inf inf |
| ATOM | 866 | O | H2O | 866 | 149.053 | −24.958 | 77.319 | inf inf |
| ATOM | 867 | O | H2O | 867 | 149.028 | −24.225 | 77.319 | inf inf |
| ATOM | 868 | O | H2O | 868 | 149.073 | −23.866 | 77.320 | inf inf |
| ATOM | 869 | O | H2O | 869 | 144.044 | −23.306 | 77.317 | inf inf |
| ATOM | 870 | O | H2O | 870 | 149.268 | −23.115 | 77.271 | inf inf |
| ATOM | 871 | O | H2O | 871 | 149.314 | −22.747 | 77.287 | inf inf |
| ATOM | 872 | O | H2O | 872 | 143.435 | −22.010 | 77.293 | inf inf |
| ATOM | 873 | O | H2O | 873 | 149.246 | −21.694 | 77.314 | inf inf |
| ATOM | 874 | O | H2O | 874 | 149.163 | −21.479 | 77.317 | inf inf |
| ATOM | 875 | O | H2O | 875 | 148.883 | −21.062 | 77.308 | inf inf |
| ATOM | 876 | O | H2O | 876 | 148.311 | −20.516 | 77.305 | inf inf |
| ATOM | 877 | O | H2O | 877 | 147.989 | −20.101 | 77.300 | inf inf |
| ATOM | 878 | O | H2O | 878 | 147.718 | −19.813 | 77.138 | inf inf |
| ATOM | 879 | O | H2O | 879 | 147.243 | −19.369 | 77.318 | inf inf |
| ATOM | 880 | O | H2O | 880 | 144.989 | −19.094 | 77.300 | inf inf |
| ATOM | 881 | O | H2O | 881 | 145.521 | −18.664 | 77.155 | inf inf |
| ATOM | 882 | O | H2O | 882 | 146.278 | −18.820 | 77.341 | inf inf |
| ATOM | 883 | O | H2O | 883 | 147.002 | −34.566 | 77.680 | inf inf |
| ATOM | 884 | O | H2O | 884 | 146.146 | −34.124 | 77.688 | inf inf |
| ATOM | 885 | O | H2O | 885 | 148.103 | −34.368 | 77.688 | inf inf |
| ATOM | 886 | O | H2O | 886 | 148.519 | −34.048 | 77.688 | inf inf |
| ATOM | 887 | O | H2O | 887 | 148.905 | −33.411 | 77.688 | inf inf |
| ATOM | 888 | O | H2O | 888 | 144.969 | −32.717 | 77.688 | inf inf |
| ATOM | 889 | O | H2O | 889 | 144.771 | −32.543 | 77.686 | inf inf |
| ATOM | 890 | O | H2O | 890 | 144.422 | −31.974 | 77.506 | inf inf |
| ATOM | 891 | O | H2O | 891 | 148.460 | −31.619 | 77.509 | inf inf |
| ATOM | 892 | O | H2O | 892 | 148.409 | −31.451 | 77.688 | inf inf |
| ATOM | 893 | O | H2O | 893 | 148.290 | −30.869 | 77.690 | inf inf |
| ATOM | 894 | O | H2O | 894 | 143.726 | −30.284 | 77.688 | inf inf |
| ATOM | 895 | O | H2O | 895 | 143.405 | −29.851 | 77.688 | inf inf |
| ATOM | 896 | O | H2O | 896 | 143.230 | −29.658 | 77.715 | inf inf |
| ATOM | 897 | O | H2O | 897 | 142.944 | −29.207 | 77.687 | inf inf |
| ATOM | 898 | O | H2O | 898 | 147.962 | −28.665 | 77.672 | inf inf |
| ATOM | 899 | O | H2O | 899 | 148.180 | −28.214 | 77.729 | inf inf |
| ATOM | 900 | O | H2O | 900 | 143.141 | −27.558 | 77.683 | inf inf |
| ATOM | 901 | O | H2O | 901 | 143.263 | −27.343 | 77.701 | inf inf |
| ATOM | 902 | O | H2O | 902 | 143.331 | −26.822 | 77.5OO | inf inf |
| ATOM | 903 | O | H2O | 903 | 143.505 | −26.444 | 77.688 | inf inf |
| ATOM | 904 | O | H2O | 904 | 143.757 | −25.995 | 77.688 | inf inf |
| ATOM | 905 | O | H2O | 905 | 149.278 | −25.703 | 77.648 | inf inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| | | | | | | | | |
|---|---|---|---|---|---|---|---|---|
| ATOM | 906 | O | H2O | 906 | 144.447 | −25.160 | 77.688 | inf inf |
| ATOM | 907 | O | H2O | 907 | 149.065 | −24.595 | 77.679 | inf inf |
| ATOM | 908 | O | H2O | 908 | 144.422 | −24.038 | 77.688 | inf inf |
| ATOM | 909 | O | H2O | 909 | 143.781 | −23.200 | 77.660 | inf inf |
| ATOM | 910 | O | H2O | 910 | 143.469 | −22.759 | 77.681 | inf inf |
| ATOM | 911 | O | H2O | 911 | 143.357 | −22.413 | 77.654 | inf inf |
| ATOM | 912 | O | H2O | 912 | 143.290 | −22.010 | 77.742 | inf inf |
| ATOM | 913 | O | H2O | 913 | 143.320 | −21.827 | 77.691 | inf inf |
| ATOM | 914 | O | H2O | 914 | 143.394 | −21.246 | 77.663 | inf inf |
| ATOM | 915 | O | H2O | 915 | 148.996 | −20.025 | 77.714 | inf inf |
| ATOM | 916 | O | H2O | 916 | 148.691 | −20.510 | 77.659 | inf inf |
| ATOM | 917 | O | H2O | 917 | 148.121 | −20.150 | 77.497 | inf inf |
| ATOM | 918 | O | H2O | 918 | 144.358 | −19.894 | 77.688 | inf inf |
| ATOM | 919 | O | H2O | 919 | 144.793 | −19.431 | 77.502 | inf inf |
| ATOM | 920 | O | H2O | 920 | 147.430 | −19.491 | 77.688 | inf inf |
| ATOM | 921 | O | H2O | 921 | 145.329 | −19.031 | 77.695 | inf inf |
| ATOM | 922 | O | H2O | 922 | 145.894 | −18.883 | 77.685 | inf inf |
| ATOM | 923 | O | H2O | 923 | 147.370 | −34.566 | 77.873 | inf inf |
| ATOM | 924 | O | H2O | 924 | 146.969 | −34.505 | 78.089 | inf inf |
| ATOM | 925 | O | H2O | 925 | 148.303 | −34.206 | 78.062 | inf inf |
| ATOM | 926 | O | H2O | 926 | 148.500 | −34.029 | 78.066 | inf inf |
| ATOM | 927 | O | H2O | 927 | 148.797 | −33.617 | 78.043 | inf inf |
| ATOM | 928 | O | H2O | 928 | 148.960 | −33.084 | 78.047 | inf inf |
| ATOM | 929 | O | H2O | 929 | 144.545 | −32.402 | 78.057 | inf inf |
| ATOM | 930 | O | H2O | 930 | 144.375 | −32.191 | 78.057 | inf inf |
| ATOM | 931 | O | H2O | 931 | 148.552 | −31.689 | 78.057 | inf inf |
| ATOM | 932 | O | H2O | 932 | 144.010 | −30.818 | 78.056 | inf inf |
| ATOM | 933 | O | H2O | 933 | 148.304 | −30.500 | 78.057 | inf inf |
| ATOM | 934 | O | H2O | 934 | 143.461 | −29.784 | 78.068 | inf inf |
| ATOM | 935 | O | H2O | 935 | 148.000 | −29.374 | 78.057 | inf inf |
| ATOM | 936 | O | H2O | 936 | 147.960 | −29.024 | 78.057 | inf inf |
| ATOM | 937 | O | H2O | 937 | 142.914 | −28.286 | 78.004 | inf inf |
| ATOM | 938 | O | H2O | 938 | 142.972 | −28.105 | 78.048 | inf inf |
| ATOM | 939 | O | H2O | 939 | 143.219 | −27.069 | 78.026 | inf inf |
| ATOM | 940 | O | H2O | 940 | 143.423 | −27.162 | 78.074 | inf inf |
| ATOM | 941 | O | H2O | 941 | 148.874 | −27.010 | 78.079 | inf inf |
| ATOM | 942 | O | H2O | 942 | 149.092 | −26.460 | 78.097 | inf inf |
| ATOM | 943 | O | H2O | 943 | 149.229 | −26.070 | 77.878 | inf inf |
| ATOM | 944 | O | H2O | 944 | 149.223 | −25.761 | 77.874 | inf inf |
| ATOM | 945 | O | H2O | 945 | 149.226 | −25.330 | 77.871 | inf inf |
| ATOM | 946 | O | H2O | 946 | 149.183 | −24.972 | 77.888 | inf inf |
| ATOM | 947 | O | H2O | 947 | 149.286 | −24.589 | 78.141 | inf inf |
| ATOM | 948 | O | H2O | 948 | 144.333 | −23.791 | 78.057 | inf inf |
| ATOM | 949 | O | H2O | 949 | 149.262 | −23.856 | 78.104 | inf inf |
| ATOM | 950 | O | H2O | 950 | 143.757 | −23.223 | 78.057 | inf inf |
| ATOM | 951 | O | H2O | 951 | 149.141 | −23.090 | 78.057 | inf inf |
| ATOM | 952 | O | H2O | 952 | 143.314 | −22.422 | 78.057 | inf inf |
| ATOM | 953 | O | H2O | 953 | 149.200 | −22.010 | 77.874 | inf inf |
| ATOM | 954 | O | H2O | 954 | 143.308 | −21.640 | 78.058 | inf inf |
| ATOM | 955 | O | H2O | 955 | 143.323 | −21.229 | 78.057 | inf inf |
| ATOM | 956 | O | H2O | 956 | 149.141 | −20.856 | 77.994 | inf inf |
| ATOM | 957 | O | H2O | 957 | 148.869 | −20.515 | 77.859 | inf inf |
| ATOM | 958 | O | H2O | 958 | 143.903 | −20.204 | 78.057 | inf inf |
| ATOM | 959 | O | H2O | 959 | 144.102 | −20.061 | 78.057 | inf inf |
| ATOM | 960 | O | H2O | 960 | 148.140 | −19.906 | 78.036 | inf inf |
| ATOM | 961 | O | H2O | 961 | 147.217 | −19.379 | 78.073 | inf inf |
| ATOM | 962 | O | H2O | 962 | 145.351 | −19.082 | 78.050 | inf inf |
| ATOM | 963 | O | H2O | 963 | 145.894 | −18.942 | 78.047 | inf inf |
| ATOM | 964 | O | H2O | 964 | 146.655 | −34.309 | 78.403 | inf inf |
| ATOM | 965 | O | H2O | 965 | 148.036 | −34.269 | 78.391 | inf inf |
| ATOM | 966 | O | H2O | 966 | 148.429 | −33.959 | 78.407 | inf inf |
| ATOM | 967 | O | H2O | 967 | 148.825 | −33.447 | 78.232 | inf inf |
| ATOM | 968 | O | H2O | 968 | 148.820 | −33.265 | 78.411 | inf inf |
| ATOM | 969 | O | H2O | 969 | 148.872 | −32.715 | 78.373 | inf inf |
| ATOM | 970 | O | H2O | 970 | 148.828 | −32.533 | 78.416 | inf inf |
| ATOM | 971 | O | H2O | 971 | 148.613 | −32.015 | 78.397 | inf inf |
| ATOM | 972 | O | H2O | 972 | 148.486 | −31.605 | 78.247 | inf inf |
| ATOM | 973 | O | H2O | 973 | 144.070 | −31.051 | 87.426 | inf inf |
| ATOM | 974 | O | H2O | 974 | 143.705 | −30.118 | 78.229 | inf inf |
| ATOM | 975 | O | H2O | 975 | 143.713 | −29.935 | 78.403 | inf inf |
| ATOM | 976 | O | H2O | 976 | 147.955 | −29.384 | 78.440 | inf inf |
| ATOM | 977 | O | H2O | 977 | 147.914 | −29.024 | 78.422 | inf inf |
| ATOM | 978 | O | H2O | 978 | 143.007 | −28.305 | 78.213 | inf inf |
| ATOM | 979 | O | H2O | 979 | 148.068 | −28.084 | 78.427 | inf inf |
| ATOM | 980 | O | H2O | 980 | 143.495 | −27.547 | 78.425 | inf inf |
| ATOM | 981 | O | H2O | 981 | 148.482 | −27.365 | 78.428 | inf inf |
| ATOM | 982 | O | H2O | 982 | 148.704 | −26.823 | 78.455 | inf inf |
| ATOM | 983 | O | H2O | 983 | 148.825 | −26.617 | 78.412 | inf inf |
| ATOM | 984 | O | H2O | 984 | 144.087 | −25.935 | 78.397 | inf inf |
| ATOM | 985 | O | H2O | 985 | 144.723 | −25.275 | 78.337 | inf inf |
| ATOM | 986 | O | H2O | 986 | 149.296 | −25.296 | 78.429 | inf inf |
| ATOM | 987 | O | H2O | 987 | 144.803 | −24.593 | 78.216 | inf inf |
| ATOM | 988 | O | H2O | 988 | 144.966 | −24.227 | 78.431 | inf inf |
| ATOM | 989 | O | H2O | 989 | 144.615 | −23.837 | 78.404 | inf inf |
| ATOM | 990 | O | H2O | 990 | 144.418 | −23.670 | 78.426 | inf inf |
| ATOM | 991 | O | H2O | 991 | 143.799 | −23.182 | 78.448 | inf inf |
| ATOM | 992 | O | H2O | 992 | 143.625 | −22.969 | 78.444 | inf inf |
| ATOM | 993 | O | H2O | 993 | 143.299 | −22.010 | 78.243 | inf inf |
| ATOM | 994 | O | H2O | 994 | 143.304 | −21.641 | 78.243 | inf inf |
| ATOM | 995 | O | H2O | 995 | 149.378 | −21.275 | 78.433 | inf inf |
| ATOM | 996 | O | H2O | 996 | 143.577 | −20.589 | 78.398 | inf inf |
| ATOM | 997 | O | H2O | 997 | 143.908 | −20.209 | 78.408 | inf inf |
| ATOM | 998 | O | H2O | 998 | 144.390 | −19.918 | 78.444 | inf inf |
| ATOM | 999 | O | H2O | 999 | 148.275 | −19.838 | 78.439 | inf inf |
| ATOM | 1000 | O | H2O | 1000 | 147.386 | −19.574 | 78.437 | inf inf |
| ATOM | 1001 | O | H2O | 1001 | 145.525 | −19.060 | 78.240 | inf inf |
| ATOM | 1002 | O | H2O | 1002 | 146.298 | −19.104 | 78.495 | inf inf |
| ATOM | 1003 | O | H2O | 1003 | 146.946 | −19.324 | 78.399 | inf inf |
| ATOM | 1004 | O | H2O | 1004 | 147.370 | −34.263 | 78.720 | inf inf |
| ATOM | 1005 | O | H2O | 1005 | 148.079 | −34.133 | 78.582 | inf inf |
| ATOM | 1006 | O | H2O | 1006 | 146.972 | −34.095 | 78.883 | inf inf |
| ATOM | 1007 | O | H2O | 1007 | 148.274 | −33.804 | 78.776 | inf inf |
| ATOM | 1008 | O | H2O | 1008 | 148.437 | −33.614 | 78.763 | inf inf |
| ATOM | 1009 | O | H2O | 1009 | 145.901 | −33.261 | 78.790 | inf inf |
| ATOM | 1010 | O | H2O | 1010 | 145.204 | −32.755 | 78.747 | inf inf |
| ATOM | 1011 | O | H2O | 1011 | 144.613 | −32.334 | 78.791 | inf inf |
| ATOM | 1012 | O | H2O | 1012 | 144.452 | −32.138 | 78.784 | inf inf |
| ATOM | 1013 | O | H2O | 1013 | 144.224 | −31.610 | 78.799 | inf inf |
| ATOM | 1014 | O | H2O | 1014 | 144.082 | −30.869 | 78.588 | inf inf |
| ATOM | 1015 | O | H2O | 1015 | 144.159 | −30.522 | 78.827 | inf inf |
| ATOM | 1016 | O | H2O | 1016 | 148.062 | −30.097 | 78.864 | inf inf |
| ATOM | 1017 | O | H2O | 1017 | 143.889 | −29.753 | 78.778 | inf inf |
| ATOM | 1018 | O | H2O | 1018 | 143.845 | −29.401 | 78.815 | inf inf |
| ATOM | 1019 | O | H2O | 1019 | 143.691 | −29.202 | 78.777 | inf inf |
| ATOM | 1020 | O | H2O | 1020 | 147.810 | −28.622 | 78.757 | inf inf |
| ATOM | 1021 | O | H2O | 1021 | 143.377 | −27.943 | 78.544 | inf inf |
| ATOM | 1022 | O | H2O | 1022 | 148.024 | −28.046 | 78.767 | inf inf |
| ATOM | 1023 | O | H2O | 1023 | 148.327 | −27.562 | 78.805 | inf inf |
| ATOM | 1024 | O | H2O | 1024 | 148.431 | −27.213 | 78.830 | inf inf |
| ATOM | 1025 | O | H2O | 1025 | 148.565 | −26.776 | 78.761 | inf inf |
| ATOM | 1026 | O | H2O | 1026 | 148.805 | −26.419 | 78.590 | inf inf |
| ATOM | 1027 | O | H2O | 1027 | 148.782 | −26.223 | 78.763 | inf inf |
| ATOM | 1028 | O | H2O | 1028 | 144.785 | −25.884 | 78.797 | inf inf |
| ATOM | 1029 | O | H2O | 1029 | 145.144 | −25.326 | 78.628 | inf inf |
| ATOM | 1030 | O | H2O | 1030 | 149.355 | −25.316 | 78.810 | inf inf |
| ATOM | 1031 | O | H2O | 1031 | 145.194 | −24.592 | 78.573 | inf inf |
| ATOM | 1032 | O | H2O | 1032 | 145.314 | −24.234 | 78.813 | inf inf |
| ATOM | 1033 | O | H2O | 1033 | 145.184 | −24.023 | 78.773 | inf inf |
| ATOM | 1034 | O | H2O | 1034 | 144.804 | −23.642 | 78.773 | inf inf |
| ATOM | 1035 | O | H2O | 1035 | 144.387 | −23.391 | 78.855 | inf inf |
| ATOM | 1036 | O | H2O | 1036 | 143.727 | −22.909 | 78.771 | inf inf |
| ATOM | 1037 | O | H2O | 1037 | 149.224 | −22.381 | 78.610 | inf inf |
| ATOM | 1038 | O | H2O | 1038 | 149.312 | −21.997 | 78.795 | inf inf |
| ATOM | 1039 | O | H2O | 1039 | 149.393 | −21.272 | 78.795 | inf inf |
| ATOM | 1040 | O | H2O | 1040 | 143.642 | −20.694 | 78.808 | inf inf |
| ATOM | 1041 | O | H2O | 1041 | 144.048 | −20.165 | 78.611 | inf inf |
| ATOM | 1042 | O | H2O | 1042 | 148.936 | −20.259 | 78.795 | inf inf |
| ATOM | 1043 | O | H2O | 1043 | 144.950 | −19.764 | 78.816 | inf inf |
| ATOM | 1044 | O | H2O | 1044 | 145.150 | −19.604 | 78.802 | inf inf |
| ATOM | 1045 | O | H2O | 1045 | 146.986 | −19.456 | 78.596 | inf inf |
| ATOM | 1046 | O | H2O | 1046 | 145.549 | −19.317 | 78.745 | inf inf |
| ATOM | 1047 | O | H2O | 1047 | 146.600 | −19.338 | 78.732 | inf inf |
| ATOM | 1048 | O | H2O | 1048 | 147.370 | −33.905 | 79.095 | inf inf |
| ATOM | 1049 | O | H2O | 1049 | 146.466 | −33.434 | 79.126 | inf inf |
| ATOM | 1050 | O | H2O | 1050 | 149.747 | −33.654 | 79.189 | inf inf |
| ATOM | 1051 | O | H2O | 1051 | 145.890 | −33.089 | 78.985 | inf inf |
| ATOM | 1052 | O | H2O | 1052 | 148.270 | −33.084 | 79.130 | inf inf |
| ATOM | 1053 | O | H2O | 1053 | 145.678 | −32.761 | 79.195 | inf inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| ATOM | 1054 | O | H2O | 1054 | 144.772 | −32.364 | 78.991 | inf | inf |
|---|---|---|---|---|---|---|---|---|---|
| ATOM | 1055 | O | H2O | 1055 | 148.224 | −32.373 | 79.096 | inf | inf |
| ATOM | 1056 | O | H2O | 1056 | 144.758 | −32.190 | 79.187 | inf | inf |
| ATOM | 1057 | O | H2O | 1057 | 144.352 | −31.567 | 79.085 | inf | inf |
| ATOM | 1058 | O | H2O | 1058 | 144.326 | −31.238 | 79.102 | inf | inf |
| ATOM | 1059 | O | H2O | 1059 | 147.917 | −30.869 | 79.160 | inf | inf |
| ATOM | 1060 | O | H2O | 1060 | 144.523 | −30.499 | 79.242 | inf | inf |
| ATOM | 1061 | O | H2O | 1061 | 144.285 | −30.110 | 79.112 | inf | inf |
| ATOM | 1062 | O | H2O | 1062 | 144.244 | −29.762 | 79.153 | inf | inf |
| ATOM | 1063 | O | H2O | 1063 | 144.049 | −29.393 | 78.978 | inf | inf |
| ATOM | 1064 | O | H2O | 1064 | 143.743 | −28.992 | 78.885 | inf | inf |
| ATOM | 1065 | O | H2O | 1065 | 147.666 | −29.023 | 78.907 | inf | inf |
| ATOM | 1066 | O | H2O | 1066 | 144.421 | −28.841 | 79.149 | inf | inf |
| ATOM | 1067 | O | H2O | 1067 | 143.719 | −28.306 | 78.920 | inf | inf |
| ATOM | 1068 | O | H2O | 1068 | 147.613 | −28.333 | 79.223 | inf | inf |
| ATOM | 1069 | O | H2O | 1069 | 144.614 | −27.916 | 79.137 | inf | inf |
| ATOM | 1070 | O | H2O | 1070 | 144.082 | −27.547 | 78.929 | inf | inf |
| ATOM | 1071 | O | H2O | 1071 | 148.239 | −27.529 | 79.146 | inf | inf |
| ATOM | 1072 | O | H2O | 1072 | 148.329 | −27.188 | 79.180 | inf | inf |
| ATOM | 1073 | O | H2O | 1073 | 148.470 | −26.807 | 78.977 | inf | inf |
| ATOM | 1074 | O | H2O | 1074 | 144.784 | −26.628 | 79.192 | inf | inf |
| ATOM | 1075 | O | H2O | 1075 | 144.471 | −26.142 | 78.891 | inf | inf |
| ATOM | 1076 | O | H2O | 1076 | 145.349 | −26.076 | 79.143 | inf | inf |
| ATOM | 1077 | O | H2O | 1077 | 145.462 | −25.625 | 79.042 | inf | inf |
| ATOM | 1078 | O | H2O | 1078 | 149.042 | −25.714 | 79.167 | inf | inf |
| ATOM | 1079 | O | H2O | 1079 | 149.378 | −25.317 | 79.165 | inf | inf |
| ATOM | 1080 | O | H2O | 1080 | 145.551 | −24.583 | 78.954 | inf | inf |
| ATOM | 1081 | O | H2O | 1081 | 149.589 | −24.593 | 79.164 | inf | inf |
| ATOM | 1082 | O | H2O | 1082 | 149.592 | −24.408 | 79.165 | inf | inf |
| ATOM | 1083 | O | H2O | 1083 | 149.471 | −23.838 | 79.165 | inf | inf |
| ATOM | 1084 | O | H2O | 1084 | 149.364 | −23.497 | 79.159 | inf | inf |
| ATOM | 1085 | O | H2O | 1085 | 144.762 | −23.337 | 79.188 | inf | inf |
| ATOM | 1086 | O | H2O | 1086 | 144.067 | −22.919 | 79.141 | inf | inf |
| ATOM | 1087 | O | H2O | 1087 | 143.827 | −22.939 | 79.201 | inf | inf |
| ATOM | 1088 | O | H2O | 1088 | 143.786 | −22.037 | 79.242 | inf | inf |
| ATOM | 1089 | O | H2O | 1089 | 149.331 | −21.640 | 79.142 | inf | inf |
| ATOM | 1090 | O | H2O | 1090 | 143.684 | −21.089 | 79.161 | inf | inf |
| ATOM | 1091 | O | H2O | 1091 | 149.056 | −20.517 | 79.173 | inf | inf |
| ATOM | 1092 | O | H2O | 1092 | 144.397 | −20.299 | 79.214 | inf | inf |
| ATOM | 1093 | O | H2O | 1093 | 144.814 | −20.072 | 79.106 | inf | inf |
| ATOM | 1094 | O | H2O | 1094 | 145.474 | −19.728 | 79.097 | inf | inf |
| ATOM | 1095 | O | H2O | 1095 | 147.024 | −19.709 | 79.016 | inf | inf |
| ATOM | 1096 | O | H2O | 1096 | 147.923 | −19.802 | 79.162 | inf | inf |
| ATOM | 1097 | O | H2O | 1097 | 145.546 | −19.480 | 78.926 | inf | inf |
| ATOM | 1098 | O | H2O | 1098 | 146.263 | −19.436 | 78.970 | inf | inf |
| ATOM | 1099 | O | H2O | 1099 | 146.670 | −33.415 | 79.234 | inf | inf |
| ATOM | 1100 | O | H2O | 1100 | 146.290 | −33.048 | 79.304 | inf | inf |
| ATOM | 1101 | O | H2O | 1101 | 147.746 | −33.091 | 79.376 | inf | inf |
| ATOM | 1102 | O | H2O | 1102 | 146.287 | −32.839 | 79.474 | inf | inf |
| ATOM | 1103 | O | H2O | 1103 | 147.405 | −32.750 | 79.489 | inf | inf |
| ATOM | 1104 | O | H2O | 1104 | 145.497 | −32.403 | 79.433 | inf | inf |
| ATOM | 1105 | O | H2O | 1105 | 147.562 | −32.349 | 79.544 | inf | inf |
| ATOM | 1106 | O | H2O | 1106 | 144.977 | −31.971 | 79.521 | inf | inf |
| ATOM | 1107 | O | H2O | 1107 | 147.830 | −31.977 | 79.440 | inf | inf |
| ATOM | 1108 | O | H2O | 1108 | 147.618 | −31.608 | 79.623 | inf | inf |
| ATOM | 1109 | O | H2O | 1109 | 147.574 | −31.229 | 79.563 | inf | inf |
| ATOM | 1110 | O | H2O | 1110 | 147.546 | −30.870 | 79.520 | inf | inf |
| ATOM | 1111 | O | H2O | 1111 | 144.944 | −30.499 | 79.596 | inf | inf |
| ATOM | 1112 | O | H2O | 1112 | 144.703 | −30.131 | 79.432 | inf | inf |
| ATOM | 1113 | O | H2O | 1113 | 144.467 | −29.762 | 79.274 | inf | inf |
| ATOM | 1114 | O | H2O | 1114 | 147.355 | −29.954 | 79.512 | inf | inf |
| ATOM | 1115 | O | H2O | 1115 | 144.932 | −29.374 | 79.592 | inf | inf |
| ATOM | 1116 | O | H2O | 1116 | 147.343 | −29.420 | 79.270 | inf | inf |
| ATOM | 1117 | O | H2O | 1117 | 146.780 | −29.024 | 79.478 | inf | inf |
| ATOM | 1118 | O | H2O | 1118 | 145.106 | −28.633 | 79.423 | inf | inf |
| ATOM | 1119 | O | H2O | 1119 | 146.632 | −28.840 | 79.528 | inf | inf |
| ATOM | 1120 | O | H2O | 1120 | 144.827 | −28.284 | 79.236 | inf | inf |
| ATOM | 1121 | O | H2O | 1121 | 146.984 | −28.453 | 79.499 | inf | inf |
| ATOM | 1122 | O | H2O | 1122 | 145.147 | −27.904 | 79.390 | inf | inf |
| ATOM | 1123 | O | H2O | 1123 | 147.366 | −28.093 | 79.525 | inf | inf |
| ATOM | 1124 | O | H2O | 1124 | 145.158 | −27.547 | 79.336 | inf | inf |
| ATOM | 1125 | O | H2O | 1125 | 148.115 | −27.551 | 79.353 | inf | inf |
| ATOM | 1126 | O | H2O | 1126 | 145.449 | −27.145 | 79.458 | inf | inf |
| ATOM | 1127 | O | H2O | 1127 | 144.802 | −26.808 | 79.181 | inf | inf |
| ATOM | 1128 | O | H2O | 1128 | 148.288 | −26.786 | 79.490 | inf | inf |
| ATOM | 1129 | O | H2O | 1129 | 148.431 | −26.417 | 79.326 | inf | inf |
| ATOM | 1130 | O | H2O | 1130 | 148.451 | −26.238 | 79.525 | inf | inf |
| ATOM | 1131 | O | H2O | 1131 | 146.015 | −25.703 | 79.596 | inf | inf |
| ATOM | 1132 | O | H2O | 1132 | 145.967 | −25.331 | 79.614 | inf | inf |
| ATOM | 1133 | O | H2O | 1133 | 145.954 | −24.963 | 79.565 | inf | inf |
| ATOM | 1134 | O | H2O | 1134 | 149.578 | −24.594 | 79.348 | inf | inf |
| ATOM | 1135 | O | H2O | 1135 | 149.516 | −24.196 | 79.563 | inf | inf |
| ATOM | 1136 | O | H2O | 1136 | 145.102 | −23.522 | 79.385 | inf | inf |
| ATOM | 1137 | O | H2O | 1137 | 144.750 | −23.173 | 79.386 | inf | inf |
| ATOM | 1138 | O | H2O | 1138 | 149.221 | −23.301 | 79.535 | inf | inf |
| ATOM | 1139 | O | H2O | 1139 | 144.604 | −22.746 | 79.531 | inf | inf |
| ATOM | 1140 | O | H2O | 1140 | 144.246 | −22.370 | 79.501 | inf | inf |
| ATOM | 1141 | O | H2O | 1141 | 143.933 | −22.038 | 79.431 | inf | inf |
| ATOM | 1142 | O | H2O | 1142 | 143.732 | −21.641 | 79.296 | inf | inf |
| ATOM | 1143 | O | H2O | 1143 | 149.254 | −21.641 | 79.365 | inf | inf |
| ATOM | 1144 | O | H2O | 1144 | 149.257 | −21.272 | 79.367 | inf | inf |
| ATOM | 1145 | O | H2O | 1145 | 149.066 | −20.891 | 79.557 | inf | inf |
| ATOM | 1146 | O | H2O | 1146 | 144.408 | −20.708 | 79.553 | inf | inf |
| ATOM | 1147 | O | H2O | 1147 | 145.524 | −20.457 | 79.457 | inf | inf |
| ATOM | 1148 | O | H2O | 1148 | 144.786 | −20.414 | 79.469 | inf | inf |
| ATOM | 1149 | O | H2O | 1149 | 145.893 | −20.163 | 79.352 | inf | inf |
| ATOM | 1150 | O | H2O | 1150 | 146.630 | −20.338 | 79.547 | inf | inf |
| ATOM | 1151 | O | H2O | 1151 | 148.803 | −20.392 | 79.491 | inf | inf |
| ATOM | 1152 | O | H2O | 1152 | 147.022 | −20.033 | 79.480 | inf | inf |
| ATOM | 1153 | O | H2O | 1153 | 148.104 | −19.992 | 79.525 | inf | inf |
| ATOM | 1154 | O | H2O | 1154 | 147.001 | −32.658 | 79.633 | inf | inf |
| ATOM | 1155 | O | H2O | 1155 | 147.015 | −32.336 | 79.766 | inf | inf |
| ATOM | 1156 | O | H2O | 1156 | 145.879 | −31.999 | 79.770 | inf | inf |
| ATOM | 1157 | O | H2O | 1157 | 146.817 | −31.979 | 79.910 | inf | inf |
| ATOM | 1158 | O | H2O | 1158 | 145.145 | −31.615 | 79.743 | inf | inf |
| ATOM | 1159 | O | H2O | 1159 | 146.446 | −31.608 | 79.913 | inf | inf |
| ATOM | 1160 | O | H2O | 1160 | 144.843 | −31.238 | 79.633 | inf | inf |
| ATOM | 1161 | O | H2O | 1161 | 145.894 | −31.422 | 79.898 | inf | inf |
| ATOM | 1162 | O | H2O | 1162 | 146.632 | −31.424 | 79.899 | inf | inf |
| ATOM | 1163 | O | H2O | 1163 | 145.144 | −30.861 | 79.746 | inf | inf |
| ATOM | 1164 | O | H2O | 1164 | 146.263 | −30.842 | 79.826 | inf | inf |
| ATOM | 1165 | O | H2O | 1165 | 145.162 | −30.500 | 79.703 | inf | inf |
| ATOM | 1166 | O | H2O | 1166 | 146.632 | −30.500 | 79.769 | inf | inf |
| ATOM | 1167 | O | H2O | 1167 | 145.502 | −30.131 | 79.810 | inf | inf |
| ATOM | 1168 | O | H2O | 1168 | 146.994 | −30.135 | 79.693 | inf | inf |
| ATOM | 1169 | O | H2O | 1169 | 145.894 | −29.762 | 79.860 | inf | inf |
| ATOM | 1170 | O | H2O | 1170 | 145.159 | −29.395 | 79.710 | inf | inf |
| ATOM | 1171 | O | H2O | 1171 | 146.584 | −29.417 | 79.648 | inf | inf |
| ATOM | 1172 | O | H2O | 1172 | 146.232 | −29.048 | 79.617 | inf | inf |
| ATOM | 1173 | O | H2O | 1173 | 146.223 | −28.646 | 79.584 | inf | inf |
| ATOM | 1174 | O | H2O | 1174 | 146.633 | −28.245 | 79.609 | inf | inf |
| ATOM | 1175 | O | H2O | 1175 | 146.631 | −27.946 | 79.762 | inf | inf |
| ATOM | 1176 | O | H2O | 1176 | 146.231 | −27.613 | 79.851 | inf | inf |
| ATOM | 1177 | O | H2O | 1177 | 147.356 | −27.702 | 79.859 | inf | inf |
| ATOM | 1178 | O | H2O | 1178 | 146.074 | −27.180 | 79.909 | inf | inf |
| ATOM | 1179 | O | H2O | 1179 | 148.034 | −27.148 | 79.643 | inf | inf |
| ATOM | 1180 | O | H2O | 1180 | 147.887 | −26.790 | 79.848 | inf | inf |
| ATOM | 1181 | O | H2O | 1181 | 147.927 | −26.441 | 79.908 | inf | inf |
| ATOM | 1182 | O | H2O | 1182 | 146.261 | −26.254 | 79.908 | inf | inf |
| ATOM | 1183 | O | H2O | 1183 | 148.287 | −26.063 | 79.894 | inf | inf |
| ATOM | 1184 | O | H2O | 1184 | 148.880 | −25.742 | 79.739 | inf | inf |
| ATOM | 1185 | O | H2O | 1185 | 148.914 | −25.584 | 79.957 | inf | inf |
| ATOM | 1186 | O | H2O | 1186 | 149.250 | −25.162 | 79.923 | inf | inf |
| ATOM | 1187 | O | H2O | 1187 | 145.774 | −24.206 | 79.894 | inf | inf |
| ATOM | 1188 | O | H2O | 1188 | 145.644 | −23.893 | 79.912 | inf | inf |
| ATOM | 1189 | O | H2O | 1189 | 149.162 | −23.453 | 79.936 | inf | inf |
| ATOM | 1190 | O | H2O | 1190 | 145.150 | −23.307 | 79.904 | inf | inf |
| ATOM | 1191 | O | H2O | 1191 | 149.120 | −22.748 | 79.903 | inf | inf |
| ATOM | 1192 | O | H2O | 1192 | 149.115 | −22.379 | 79.903 | inf | inf |
| ATOM | 1193 | O | H2O | 1193 | 149.050 | −22.004 | 79.911 | inf | inf |
| ATOM | 1194 | O | H2O | 1194 | 144.786 | −21.825 | 79.903 | inf | inf |
| ATOM | 1195 | O | H2O | 1195 | 144.404 | −21.263 | 79.748 | inf | inf |
| ATOM | 1196 | O | H2O | 1196 | 144.435 | −20.921 | 79.663 | inf | inf |
| ATOM | 1197 | O | H2O | 1197 | 145.508 | −21.056 | 79.948 | inf | inf |
| ATOM | 1198 | O | H2O | 1198 | 148.851 | −21.086 | 79.908 | inf | inf |
| ATOM | 1199 | O | H2O | 1199 | 145.921 | −20.597 | 79.655 | inf | inf |
| ATOM | 1200 | O | H2O | 1200 | 146.624 | −20.663 | 79.934 | inf | inf |
| ATOM | 1201 | O | H2O | 1201 | 148.805 | −20.575 | 79.677 | inf | inf |

TABLE 9-continued

Coordinates of Composite Binding Pocket
These coordinates can be entered into a molecular graphics program to generate a molecular surface representation of the composite binding pocket, which then can be used to design and evaluate inhibitors of RT.

| ATOM | 1202 | O | H2O | 1202 | 147.364 | −20.127 | 79.749 | inf | inf |
|---|---|---|---|---|---|---|---|---|---|
| ATOM | 1203 | O | H2O | 1203 | 148.117 | −20.139 | 79.735 | inf | inf |
| ATOM | 1204 | O | H2O | 1204 | 146.632 | −31.608 | 79.925 | inf | inf |
| ATOM | 1205 | O | H2O | 1205 | 147.330 | −27.507 | 79.967 | inf | inf |
| ATOM | 1206 | O | H2O | 1206 | 147.360 | −27.173 | 80.053 | inf | inf |
| ATOM | 1207 | O | H2O | 1207 | 147.366 | −26.809 | 80.072 | inf | inf |
| ATOM | 1208 | O | H2O | 1208 | 147.001 | −26.440 | 80.108 | inf | inf |
| ATOM | 1209 | O | H2O | 1209 | 147.001 | −26.089 | 80.155 | inf | inf |
| ATOM | 1210 | O | H2O | 1210 | 146.620 | −25.707 | 80.106 | inf | inf |
| ATOM | 1211 | O | H2O | 1211 | 147.736 | −25.880 | 80.263 | inf | inf |
| ATOM | 1212 | O | H2O | 1212 | 146.311 | −25.313 | 80.039 | inf | inf |
| ATOM | 1213 | O | H2O | 1213 | 148.793 | −25.463 | 80.218 | inf | inf |
| ATOM | 1214 | O | H2O | 1214 | 149.225 | −24.966 | 80.093 | inf | inf |
| ATOM | 1215 | O | H2O | 1215 | 149.102 | −24.594 | 80.343 | inf | inf |
| ATOM | 1216 | O | H2O | 1216 | 149.096 | −24.225 | 80.337 | inf | inf |
| ATOM | 1217 | O | H2O | 1217 | 149.196 | −23.862 | 80.074 | inf | inf |
| ATOM | 1218 | O | H2O | 1218 | 145.135 | −23.127 | 80.098 | inf | inf |
| ATOM | 1219 | O | H2O | 1219 | 145.162 | −22.931 | 80.268 | inf | inf |
| ATOM | 1220 | O | H2O | 1220 | 144.849 | −22.043 | 79.987 | inf | inf |
| ATOM | 1221 | O | H2O | 1221 | 148.947 | −22.038 | 80.215 | inf | inf |
| ATOM | 1222 | O | H2O | 1222 | 148.825 | −21.839 | 80.254 | inf | inf |
| ATOM | 1223 | O | H2O | 1223 | 145.522 | −21.455 | 80.275 | inf | inf |
| ATOM | 1224 | O | H2O | 1224 | 148.543 | −21.223 | 80.202 | inf | inf |
| ATOM | 1225 | O | H2O | 1225 | 146.236 | −21.008 | 80.324 | inf | inf |
| ATOM | 1226 | O | H2O | 1226 | 148.492 | −20.896 | 80.108 | inf | inf |
| ATOM | 1227 | O | H2O | 1227 | 147.370 | −20.747 | 80.228 | inf | inf |
| ATOM | 1228 | O | H2O | 1228 | 148.090 | −20.746 | 80.207 | inf | inf |
| ATOM | 1229 | O | H2O | 1229 | 147.369 | −25.639 | 80.362 | inf | inf |
| ATOM | 1230 | O | H2O | 1230 | 146.992 | −25.350 | 80.483 | inf | inf |
| ATOM | 1231 | O | H2O | 1231 | 148.489 | −25.355 | 80.491 | inf | inf |
| ATOM | 1232 | O | H2O | 1232 | 146.999 | −25.152 | 80.645 | inf | inf |
| ATOM | 1233 | O | H2O | 1233 | 148.467 | −25.137 | 80.619 | inf | inf |
| ATOM | 1234 | O | H2O | 1234 | 146.318 | −24.710 | 80.600 | inf | inf |
| ATOM | 1235 | O | H2O | 1235 | 145.894 | −24.225 | 80.456 | inf | inf |
| ATOM | 1236 | O | H2O | 1236 | 145.821 | −23.819 | 80.604 | inf | inf |
| ATOM | 1237 | O | H2O | 1237 | 145.558 | −23.461 | 80.437 | inf | inf |
| ATOM | 1238 | O | H2O | 1238 | 145.673 | −23.136 | 80.695 | inf | inf |
| ATOM | 1239 | O | H2O | 1239 | 145.213 | −22.748 | 80.418 | inf | inf |
| ATOM | 1240 | O | H2O | 1240 | 148.880 | −22.748 | 80.480 | inf | inf |
| ATOM | 1241 | O | H2O | 1241 | 148.877 | −22.379 | 80.477 | inf | inf |
| ATOM | 1242 | O | H2O | 1242 | 148.632 | −22.022 | 80.611 | inf | inf |
| ATOM | 1243 | O | H2O | 1243 | 148.288 | −21.647 | 80.633 | inf | inf |
| ATOM | 1244 | O | H2O | 1244 | 145.907 | −21.466 | 80.624 | inf | inf |
| ATOM | 1245 | O | H2O | 1245 | 147.398 | −21.200 | 80.559 | inf | inf |
| ATOM | 1246 | O | H2O | 1246 | 148.109 | −21.271 | 80.458 | inf | inf |
| ATOM | 1247 | O | H2O | 1247 | 147.001 | −21.124 | 80.604 | inf | inf |
| ATOM | 1248 | O | H2O | 1248 | 148.062 | −20.949 | 80.316 | inf | inf |
| ATOM | 1249 | O | H2O | 1249 | 148.108 | −24.957 | 80.817 | inf | inf |
| ATOM | 1250 | O | H2O | 1250 | 146.487 | −24.554 | 80.971 | inf | inf |
| ATOM | 1251 | O | H2O | 1251 | 148.087 | −24.736 | 80.946 | inf | inf |
| ATOM | 1252 | O | H2O | 1252 | 146.304 | −24.378 | 80.959 | inf | inf |
| ATOM | 1253 | O | H2O | 1253 | 146.090 | −23.851 | 80.999 | inf | inf |
| ATOM | 1254 | O | H2O | 1254 | 146.076 | −23.487 | 81.102 | inf | inf |
| ATOM | 1255 | O | H2O | 1255 | 146.081 | −23.117 | 81.006 | inf | inf |
| ATOM | 1256 | O | H2O | 1256 | 146.081 | −22.748 | 81.003 | inf | inf |
| ATOM | 1257 | O | H2O | 1257 | 145.568 | −22.379 | 80.760 | inf | inf |
| ATOM | 1258 | O | H2O | 1258 | 148.489 | −22.379 | 80.843 | inf | inf |
| ATOM | 1259 | O | H2O | 1259 | 148.106 | −22.196 | 81.002 | inf | inf |
| ATOM | 1260 | O | H2O | 1260 | 146.242 | −21.599 | 80.888 | inf | inf |
| ATOM | 1261 | O | H2O | 1261 | 147.014 | −21.806 | 81.056 | inf | inf |
| ATOM | 1262 | O | H2O | 1262 | 147.739 | −21.845 | 80.946 | inf | inf |
| ATOM | 1263 | O | H2O | 1263 | 146.632 | −21.300 | 80.783 | inf | inf |
| ATOM | 1264 | O | H2O | 1264 | 147.370 | −24.619 | 81.232 | inf | inf |
| ATOM | 1265 | O | H2O | 1265 | 146.595 | −24.262 | 81.250 | inf | inf |
| ATOM | 1266 | O | H2O | 1266 | 147.727 | −24.385 | 81.343 | inf | inf |
| ATOM | 1267 | O | H2O | 1267 | 146.275 | −23.851 | 81.183 | inf | inf |
| ATOM | 1268 | O | H2O | 1268 | 148.255 | −23.836 | 81.322 | inf | inf |
| ATOM | 1269 | O | H2O | 1269 | 148.264 | −23.487 | 81.336 | inf | inf |
| ATOM | 1270 | O | H2O | 1270 | 146.617 | −23.298 | 81.405 | inf | inf |
| ATOM | 1271 | O | H2O | 1271 | 148.173 | −23.069 | 81.308 | inf | inf |
| ATOM | 1272 | O | H2O | 1272 | 147.002 | −22.681 | 81.331 | inf | inf |
| ATOM | 1273 | O | H2O | 1273 | 147.751 | −22.915 | 81.420 | inf | inf |
| ATOM | 1274 | O | H2O | 1274 | 146.632 | −22.380 | 81.191 | inf | inf |
| ATOM | 1275 | O | H2O | 1275 | 147.728 | −22.392 | 81.160 | inf | inf |
| ATOM | 1276 | O | H2O | 1276 | 147.001 | −22.202 | 81.123 | inf | inf |
| ATOM | 1277 | O | H2O | 1277 | 147.370 | −24.195 | 81.476 | inf | inf |
| ATOM | 1278 | O | H2O | 1278 | 147.370 | −23.858 | 81.573 | inf | inf |
| ATOM | 1279 | O | H2O | 1279 | 147.002 | −23.487 | 81.559 | inf | inf |
| ATOM | 1280 | O | H2O | 1280 | 147.009 | −23.134 | 81.506 | inf | inf |
| TER | | | | | | | | | |

We claim:

1. A compound comprising the formula:

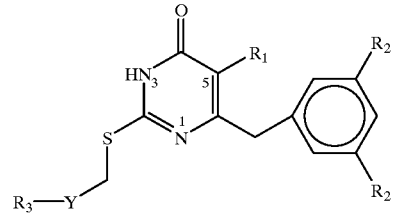

wherein Y is S or O;

$R_1$ and $R_2$ are hydrogen, halo, alkyl, alkenyl, hydroxy, alkoxy, thioalkyl, thiol, phosphino, ROH, or $RNH_2$ group, where R is alkyl; and $R_3$ is alkyl, alkenyl, aryl, aralkyl, ROH, or $RNH_2$ group, where R is alkyl; or a pharmaceutically acceptable salt thereof.

2. The compound of claim 1, wherein $R_1$ is alkyl, alkenyl, ROH, or $RNH_2$.

3. The compound of claim 1, wherein $R_1$ is methyl, ethyl, or isopropyl.

4. The compound of claim 1, wherein $R_2$ is halo, alkyl, or C1–C3 alkoxy.

5. The compound of claim 1, wherein Y is S.

6. The compound of claim 1, wherein $R_3$ is C1–C3 alkyl.

7. A compound of claim 1 which is 5-isopropyl-2-[(methylthiomethyl)thio]-6-(benzyl)-pyrimidin-4-(1H)-one or a pharmaceutically acceptable salt thereof.

8. The compound of claim 1, selected from the group consisting of:
5-methyl-2-[(methylthiomethyl)thio]-6-benzyl-pyrimidin-4-(1H)-one;
5-ethyl-2-[(methylthiomethyl)thio]-6-benzyl-pyrimidin-4-(1H)-one;
5-isopropyl-2-[(methylthiomethyl)thio]-6-(3,5-dimethylbenzyl)pyrimidin-4-(1H)-one; and
pharmaceutically acceptable salts of.

9. A method for inhibiting reverse transcriptase activity of a retrovirus comprising contacting the retrovirus with a compound of claim 1.

10. A method for inhibiting replication of a retrovirus comprising contacting the retrovirus with a compound of claim 1.

11. The method of claim 9 wherein the retrovirus is human immunodeficiency virus-1 (HIV-1).

* * * * *